(12) United States Patent
Takeuchi et al.

(10) Patent No.: US 8,569,504 B2
(45) Date of Patent: Oct. 29, 2013

(54) IMIDAZOPYRIDINE COMPOUND

(75) Inventors: Jun Takeuchi, Osaka (JP); Takayuki Inukai, Osaka (JP); Masaru Sakai, Osaka (JP)

(73) Assignee: Ono Pharmaceutical Co., Ltd., Osaka-Shi (JP)

( * ) Notice: Subject to any disclaimer, the term of this patent is extended or adjusted under 35 U.S.C. 154(b) by 0 days.

(21) Appl. No.: 13/378,550

(22) PCT Filed: Jun. 16, 2010

(86) PCT No.: PCT/JP2010/060172
§ 371 (c)(1),
(2), (4) Date: Dec. 15, 2011

(87) PCT Pub. No.: WO2010/147133
PCT Pub. Date: Dec. 23, 2010

(65) Prior Publication Data
US 2012/0094944 A1    Apr. 19, 2012

(30) Foreign Application Priority Data
Jun. 17, 2009    (JP) .................... 2009-143840

(51) Int. Cl.
A61K 31/437    (2006.01)
A61K 31/5377    (2006.01)
A61K 31/496    (2006.01)
C07D 487/04    (2006.01)
C07D 487/14    (2006.01)
C07D 471/04    (2006.01)

(52) U.S. Cl.
USPC ............ 546/121; 540/597; 544/58.6; 544/61; 544/127; 544/362; 514/300; 514/234.5; 514/254.06; 514/228.2; 514/217.09

(58) Field of Classification Search
USPC ....................................... 546/121
See application file for complete search history.

(56) References Cited

U.S. PATENT DOCUMENTS

| | | | |
|---|---|---|---|
| 2003/0083315 A1 | 5/2003 | Tsuchiya et al. | |
| 2010/0029637 A1 | 2/2010 | De Lombaert et al. | |

FOREIGN PATENT DOCUMENTS

| | | | |
|---|---|---|---|
| GB | 1473819 A | 5/1977 | |
| JP | 52-116494 A | 9/1977 | |
| JP | 06-184149 A | 7/1994 | |
| JP | 2001-199983 A | 7/2001 | |
| WO | WO-2001/053272 A1 | 7/2001 | |
| WO | WO-2008/045688 A1 | 4/2008 | |
| WO | WO-2008/153129 A1 | 12/2008 | |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Maki Terakawa et al. "Oral chymase inhibitor SUN13834 ameliorates skin inflammation as well as pruritus in mouse model for atopic dermatitis," Eur. J. Pharmacol., 2008, vol. 601, pp. 186-191.
Kumi Ishida et al., "Role of Chymase-Dependent Matrix Metalloproteinase-9 Activation in Mice with Dextran Sodium Sulfate-Induced Colitis," J. Pharmacol. Exp. Ther., 2008, vol. 324, pp. 422-426.
Denan Jin et al., "Impact of chymase inhibitor on cardiac function and survival after myocardial infarction," Cardiovascular Research, 2003, vol. 60, pp. 413-420.
Yoshiaki Tomimori et al., "Involvement of mast cell chymase in bleomycin-induced pulmonary fibrosis in mice," Eur. J. Pharmacol., 2003, vol. 478, pp. 179-185.
Hidenori Urata et al., "Angiotensin II-Forming Pathways in Normal and Failing Human Hearts," Circulation Research, vol. 66, No. 4, Apr. 1990, pp. 883-890.
International Search Report dated Aug. 3, 2010, issued for PCT/JP2010/060172.
Extended European Search Report issued in corresponding European Patent Application No. EP 10789507.0, dated Oct. 5, 2012.

* cited by examiner

Primary Examiner — Laura L. Stockton
(74) Attorney, Agent, or Firm — Edwards Wildman Palmer LLP; James E. Armstrong, IV; Nicholas J. DiCeglie, Jr.

(57) ABSTRACT

For the prevention and/or treatment of chymase-mediated diseases such as skin diseases, circulatory diseases, digestive system diseases, respiratory diseases, liver diseases, ocular diseases or the like, a drug is provided having as an active ingredient a compound having extremely strong chymase inhibitory activity, high safety, and high metabolic stability. The compound represented by the formula (I):

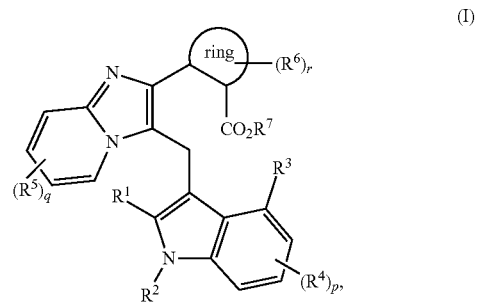

(I)

wherein all symbols have the same meanings as in the description,
a salt thereof, an N-oxide thereof or a solvate thereof, or a prodrug thereof, is useful as a pharmaceutical ingredient having chymase inhibitory activity for preventing and/or treating of chymase-mediated disease, such as skin diseases, circulatory diseases, digestive system diseases, respiratory diseases, liver diseases, ocular diseases or the like.

10 Claims, No Drawings

IMIDAZOPYRIDINE COMPOUND

TECHNICAL FIELD

The present invention relates to an imidazopyridine compound, a salt thereof, an N-oxide thereof or a solvate thereof, or a prodrug thereof, and a pharmaceutical containing as an active ingredient the same. Specifically, the present invention relates to the imidazopyridine compound represented by the formula (I):

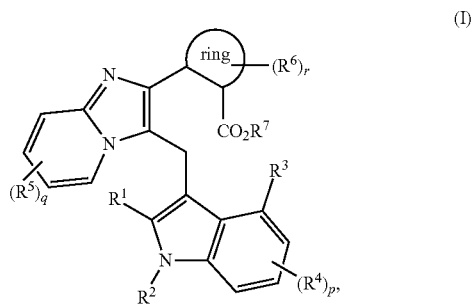

wherein all symbols have the same meaning as below,
a salt thereof, an N-oxide thereof or a solvate thereof, or a prodrug thereof (hereinafter referred to comprehensively as the compound of the present invention), and a pharmaceutical containing as an active ingredient the same.

BACKGROUND ART

Human chymase is a neutral serine protease isolated in 1990 that exhibits specificity for chymotrypsin-like substrates, and has a molecular weight of about 30,000. Chymase exists principally in granules within mast cells, and is excreted when the mast cells are degranulated. The excreted chymase escapes inhibition by inhibitors in the body by binding to the extracellular matrix such as heparan sulfate proteoglycans, and is known to produce enzymatic activity over a long period of time in the heart, the blood vessels, the skin and the other tissues.

Angiotensin converting enzyme (ACE) has previously been known as the principal enzyme involved in conversion of angiotensin I into angiotensin II, but recently it has been reported that chymase is deeply involved in converting angiotensin I into angiotensin II in the heart, blood vessels and other tissues (Non-patent Document 5). In particular, in the human heart, it has been found that ACE is involved in about 10 to 15% of angiotensin II production, while chymase is involved in most of the remainder.

Moreover, chymase has been found to exhibit the following actions in addition to angiotensin II production: promotion of mast cell degranulation, conversion of interleukin-1β and interleukin-18 from their precursor forms to their active forms, activation of matrix metalloproteinase (hereunder abbreviated as MMP) such as MMP-2 and MMP-9, activation of transforming growth factor beta (TGF-β), release of stem cell factors (SCF) expressed in the cell membrane from the cell membrane, conversion of big endothelin 1 into endothelin 1 (1-31) consisting of 31 amino acid residues, and the like. Animal experiments have also suggested that in addition to being closely associated with these various biological reaction, chymase is also involved in many diseases including atopic dermatitis, ulcerative colitis, heart failure, pulmonary fibrosis, post-surgical organ adhesion, and the like (Non-patent Documents Nos. 1, 2, 3 and 4).

Thus, if a drug that strongly inhibits chymase could be created, this chymase inhibitor would have the potential to be a novel type of cardiovascular agent, anti-inflammatory agent and anti-allergy drug.

Chymase inhibitors have already been disclosed in Patent Documents 1, 2 and 3, and the like.

According to Patent Document 1, the compound represented by the formula (Ia):

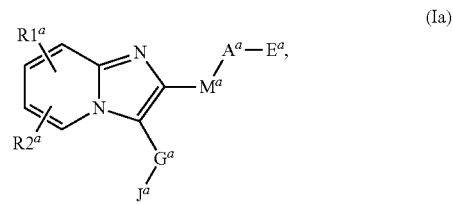

wherein $R1^a$ and $R2^a$ are each independently a hydrogen atom, halogen, trihaloalkyl, $C_{1-4}$ alkyl or the like; $A^a$ is $C_{1-7}$ linear, branched or cyclic alkyl optionally interrupted by one or more of —O—, —S—, —SO—, —SO$_2$— and —NRa$^a$— optionally substituted with 1 to 3 substituents selected from the halogens, $C_{1-6}$ linear or branched alkyl, $C_{1-6}$ linear or branched alkoxy, $C_{1-6}$ linear or branched alkylthio, $C_{1-6}$ linear or branched alkylsulfonyl, phenyl and oxo groups; $E^a$ is —COORe$^a$ or the like; each Re$^a$ is independently a hydrogen atom or $C_{1-4}$ alkyl or aryl; $G^a$ is a $C_{1-6}$ linear or branched alkyl optionally interrupted by one or more of —O—, —S—, —SO$_2$— and —NRa$^a$—; $M^a$ is a methylene group, oxygen atom, —N(Rb$^a$)— or —S(O)$_m{}^a$—; $J^a$ is a carbocyclic aromatic compound having 4 to 10 carbon atoms and optionally having one or more substituents, or a heterocyclic aromatic compound containing one or more hetero atoms selected from an oxygen atom, a nitrogen atom and a sulfur atom in a ring; and the necessary parts have been excerpted in explaining the groups, or its pharmaceutically acceptable salt, is a chymase inhibitor.

According to Patent Document 2, the benzimidazole derivative represented by the formula (Ib):

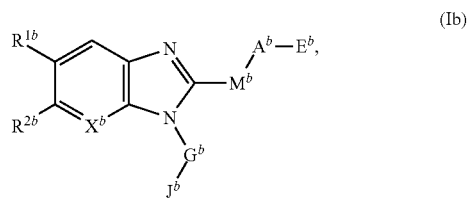

wherein $R^{1b}$ and $R^{2b}$ simultaneously or independently represent a hydrogen atom, halogen atom, trihalomethyl group, $C_{1-4}$ alkyl group or the like; $A^b$ is a substituted or unsubstituted $C_{6-11}$ arylene group or a substituted or unsubstituted $C_{4-10}$ heteroarylene group optionally having one or more oxygen, nitrogen or sulfur atoms on a ring; $E^b$ is —COOR$^{3b}$ or the like; $R^{3b}$ is a hydrogen atom or $C_{1-6}$ linear or branched alkyl group; $G^b$ is a substituted or unsubstituted $C_{1-6}$ linear or branched alkylene group; $M^b$ is a single bond or S(O)$_m{}^b$; $m^b$ is an integer of 0 to 2; $J^b$ is a substituted or unsubstituted $C_{6-11}$ aryl group or a substituted or unsubstituted $C_{4-40}$ heteroaryl group optionally having one or more oxygen, nitrogen or sulfur atoms on a ring; $X^b$ is CH or a nitrogen atom; and the necessary parts have been excerpted in explaining the groups, or its pharmaceutically acceptable salt, is a chymase inhibitor.

According to Patent Document 3, the nitrogen-containing aromatic ring derivative represented by the formula (Ic):

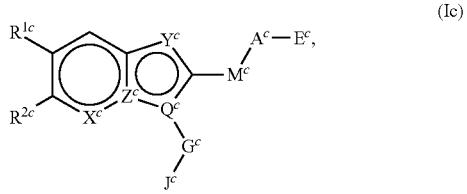

wherein $R^{1c}$ and $R^{2c}$ simultaneously or independently represent a hydrogen atom, halogen atom, trihalomethyl group, $C_{1-4}$ alkyl group or the like; $A^c$ is a substituted or unsubstituted $C_{6-11}$ arylene group or a substituted or unsubstituted $C_{4-10}$ heteroarylene group having one or more hetero atoms selected from the group consisting of oxygen atom, nitrogen atom and sulfur atom on a ring or the like; $E^c$ is —$COOR^{3c}$ or the like; $R^{3c}$ is a hydrogen atom or $C_{1-6}$ linear or branched alkyl group; $G^c$ is a substituted or unsubstituted $C_{1-6}$ linear or branched alkylene group or the like; $M^c$ is a single bond or —$S(O)_m{}^c$— (in which $_m{}^c$ is an integer of 0 to 2); when $M^c$ is a single bond, $J^c$ is a substituted or unsubstituted $C_{6-11}$ aryl group or a substituted or unsubstituted $C_{4-10}$ heteroaryl group having one or more hetero atoms selected from a group consisting of oxygen atom, nitrogen atom and sulfur atom on a ring or the like; $X^c$ is —CH= or nitrogen atom; $Y^c$ is —$CB^c$= or nitrogen atom; $Z^c$ is carbon atom or nitrogen atom; $Q^c$ is carbon atom or nitrogen atom; and the necessary parts have been excerpted in explaining the groups,
or its salt, is a URAT1 inhibitor, and this invention compound has chymase inhibitory activity.

The chymase inhibitors disclosed hitherto have not been satisfactory in terms of enzyme inhibitory activity, safety and metabolic stability. Moreover, in addition to its effectiveness for the disease, in the case the gap (ratio) between the dosage at which the drug is effective and the dosage at which side-effects appear is greater, a drug is superior in terms of safety.

Patent Document 1: WO 2008/045688
Patent Document 2: JP 2001-199983
Patent Document 3: WO 2008/153129
Non-Patent Document 1: Eur. J. Pharmacol., 2008, Vol. 601, p. 186-191
Non-Patent Document 2: J. Pharmacol. Exp. Ther., 2008, Vol. 324, 422-426
Non-Patent Document 3: Cardiovascular Research, 2003, Vol. 60, 413-420
Non-Patent Document 4: Eur. J. Pharmacol., 2003, Vol. 478, p. 179-185
Non-Patent Document 5: Circulation Research 66, 883, 1990

DISCLOSURE OF THE INVENTION

Problem to be Solved by the Invention

In the field of chymase inhibitors that are effective against chymase-mediated diseases including skin diseases, circulatory diseases, digestive system diseases, respiratory diseases, liver diseases, ocular diseases and the like, there is demand for drugs that have extremely strong chymase inhibitory activity, that have a large gap (ratio) between chymase inhibitory activity and toxicity (in other words that are highly safer), and that are metabolically stable.

Means for Solving the Problem

As a result of exhaustive research aimed at solving this problem, the inventors in this case discovered that the compound of the present invention can achieve this object.

That is, the present invention relates to:
[1] a compound represented by the formula (I)

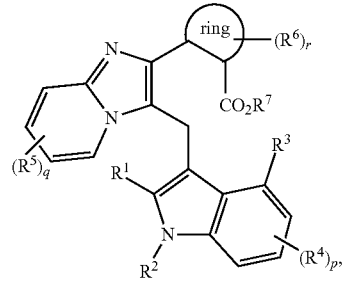

wherein

represents a benzene ring or a naphthalene ring or a 6- to 10-membered monocyclic or bicyclic aromatic heterocycle;

$R^1$ represents a hydrogen atom, methyl group, trifluoromethyl group, difluoromethyl group, fluorine atom or chlorine atom;

$R^2$ represents a hydrogen atom, $C_{1-10}$ alkyl group optionally substituted with 1 to 6 of $R^{11}$, $C_{2-10}$ alkenyl optionally substituted with 1 to 6 of $R^{11}$, or $C_{2-10}$ alkynyl optionally substituted with 1 to 6 of $R^{11}$;

$R^{11}$ represents
(i) a halogen atom,
(ii) $OR^8$,
where $R^8$ is (1) a hydrogen atom, (2) $C_{1-3}$ alkyl group, (3) $C_{1-3}$ haloalkyl group, (4) a $C_{5-6}$ carbocycle, (5) a 5- to 6-membered heterocycle containing 1 to 2 nitrogen atoms, 1 oxygen atom and/or 1 optionally oxidized sulfur atom, or (6) $C_{1-3}$ alkyl group substituted with a hydroxyl group, $C_{1-3}$ alkoxy group or $NR^9R^{10}$, where $R^9$ and $R^{10}$ each independently represent a hydrogen atom, $C_{1-3}$ alkyl group or phenyl group,
(iii) $NR^9R^{10}$, where $R^9$ and $R^{10}$ each independently represent a hydrogen atom, $C_{1-3}$ alkyl group or phenyl group,
(iv) a $C_{5-6}$ carbocycle optionally substituted with at least one selected from a halogen atom, oxo group and methyl group, or
(v) a 3- to 10-membered heterocycle containing 1 to 4 nitrogen atoms, 1 to 2 oxygen atoms and/or 1 to 2 optionally oxidized sulfur atoms, optionally substituted with at least one group selected from a halogen atom, an oxo group and a methyl group;

$R^3$ represents a hydrogen atom, methyl group, or fluorine atom;

$R^4$ represents a hydrogen atom, $C_{1-2}$ alkyl group, $C_{1-2}$ haloalkyl group, or halogen atom;

$R^5$ represents a hydrogen atom, $C_{1-3}$ alkyl group, $C_{1-3}$ haloalkyl group, or halogen atom;

$R^6$ represents a hydrogen atom, $C_{1-3}$ alkyl group, $C_{1-3}$ haloalkyl group or halogen atom;

$R^7$ represents a hydrogen atom, $C_{1-4}$ alkyl group, allyl group, trichloroethyl group, benzyl group, phenacyl group, p-methoxybenzyl group, trityl group, or 2-chlorotrityl group;

p is an integer of 1 to 3;

q is an integer of 1 to 4; and r is an integer of 1 to 6;

but when each p, q and r represent integers of 2 or more, $R^4$, $R^5$ and $R^6$ may each independently be the same or different, a salt thereof, an N-oxide thereof or a solvate thereof, or a prodrug thereof;

[2] the compound according to [1] above, represented by the formula (I-a)

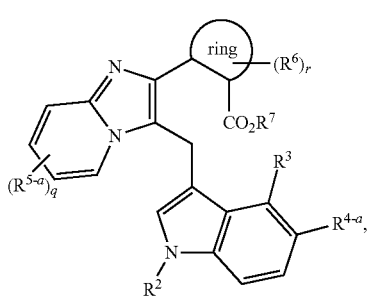

(I-a)

wherein $R^{4-a}$ represents a hydrogen atom, methyl group, fluorine atom or chlorine atom, $R^{5-a}$ represents a hydrogen atom, methyl group or fluorine atom, and the other symbols have the same meaning as in [1] above;

[3] the compound according to [2] above,

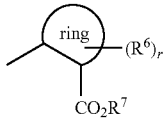

is

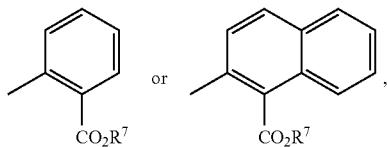

or wherein all symbols have the same meaning as in [1] above;

[4] the compound according to [3] above, wherein $R^2$ represents a hydrogen atom, $C_{1-10}$ alkyl group optionally substituted with 1 to 6 of $R^{12}$, $C_{2-10}$ alkenyl optionally substituted with 1 to 6 of $R^{12}$ or $C_{2-10}$ alkynyl optionally substituted with 1 to 6 of $R^{12}$; and $R^{12}$ represents a halogen atom, hydroxyl group, dimethylamino group, pyrrolidinyl group, N-methylpyrrolidinyl group, piperidinyl group, phenoxy group optionally substituted with halogen atoms, phenyl group optionally substituted with halogen atoms, tetrahydropyranyl group, 2,3-dihydrobenzofuranyl group, thiophenyl group, diisopropylamino group, methyl(phenyl)amino group, piperadinyl group, 2-oxo-1-pyrrolidinyl group, morpholinyl group, 1,1-dioxothiomorpholinyl group, imidazolyl group, pyridyl group, 2-methoxyethylenoxy group, dimethylaminoethylenoxy group, diethylaminoethylenoxy group, 1,2,3,4-tetrahydroisoquinolinyl group, azepanyl group, pyrazolyl group, 2-oxoimidazolidinyl group, diethylamino group, methoxy group or N-methylpyrazolyl group;

[5] the compound according to [3] above, wherein $R^2$ represents $C_{1-6}$ alkyl group substituted with 1 to 6 of $R^{12}$, $C_{2-6}$ alkenyl group optionally substituted with 1 to 6 of $R^{12}$, or $C_{2-6}$ alkynyl group optionally substituted with 1 to 6 of $R^{12}$, and $R^{12}$ is defined as in [4] above;

[6] the compound according to [4] above, wherein $R^7$ is a hydrogen atom;

[7] the compound according to [6] above, wherein the compound represented by the formula (I) is selected from the group consisting of (1) 2-{3-[(4-methyl-1H-indol-3-yl)methyl]imidazo[1,2-a]pyridin-2-yl}-1-naphthoic acid, (2) 2-{3-[(1,4-dimethyl-1H-indol-3-yl)methyl]-6-methylimidazo[1,2-a]pyridin-2-yl}benzoic acid, (3) 2-{3-[(1,4-dimethyl-1H-indol-3-yl)methyl]imidazo[1,2-a]pyridin-2-yl}benzoic acid, (4) 2-{3-[(1-ethyl-4-methyl-1H-indol-3-yl)methyl]imidazo[1,2-a]pyridin-2-yl}benzoic acid, (5) 2-{6-fluoro-3-[(4-methyl-1H-indol-3-yl)methyl]imidazo[1,2-a]pyridin-2-yl}-1-naphthoic acid, (6) 2-{3-[(5-fluoro-4-methyl-1H-indol-3-yl)methyl]imidazo[1,2-a]pyridin-2-yl}benzoic acid, (7) 2-[3-({4-methyl-1-[2-(4-morpholinyl)ethyl]-1H-indol-3-yl}methyl)imidazo[1,2-a]pyridin-2-yl]-1-naphthoic acid, (8) 2-(3-{[4-methyl-1-(2-propanyl)-1H-indol-3-yl]methyl}imidazo[1,2-a]pyridin-2-yl)-1-naphthoic acid, (9) 2-{3-[(4-methyl-1-propyl-1H-indol-3-yl)methyl]imidazo[1,2-a]pyridin-2-yl}-1-naphthoic acid,

(10) 2-{3-[(1-ethyl-4-methyl-1H-indol-3-yl)methyl]imidazo[1,2-a]pyridin-2-yl}-1-naphthoic acid,

(11) 2-{3-[(5-fluoro-4-methyl-1H-indol-3-yl)methyl]imidazo[1,2-a]pyridin-2-yl}-1-naphthoic acid,

(12) 2-(3-{[1-(2-hydroxyethyl)-4-methyl-1H-indol-3-yl]methyl}imidazo[1,2-a]pyridin-2-yl)-1-naphthoic acid,

(13) 2-[3-({1-[3-(dimethylamino)-2-hydroxypropyl]-4-methyl-1H-indol-3-yl}methyl)imidazo[1,2-a]pyridin-2-yl]-1-naphthoic acid,

(14) 2-(3-{[1-(2,3-dihydroxypropyl)-4-methyl-1H-indol-3-yl]methyl}imidazo[1,2-a]pyridin-2-yl)-1-naphthoic acid,

(15) 2-[3-({1-[2-(dimethylamino)ethyl]-4-methyl-1H-indol-3-yl}methyl)imidazo[1,2-a]pyridin-2-yl]-1-naphthoic acid,

(16) 2-[3-({1-[3-(dimethylamino)propyl]-4-methyl-1H-indol-3-yl}methyl)imidazo[1,2-a]pyridin-2-yl]-1-naphthoic acid,

(17) 2-[3-({4-methyl-1-[2-(pyrrolidin-1-yl)ethyl]-1H-indol-3-yl}methyl)imidazo[1,2-a]pyridin-2-yl]-1-naphthoic acid,

(18) 2-[3-({4-methyl-1-[2-(1-methylpyrrolidin-2-yl)ethyl]-1H-indol-3-yl}methyl)imidazo[1,2-a]pyridin-2-yl]-1-naphthoic acid,

(19) 2-[3-({4-methyl-1-[2-(piperidin-1-yl)ethyl]-1H-indol-3-yl}methyl)imidazo[1,2-a]pyridin-2-yl]-1-naphthoic acid,

(20) 2-(3-{[4-methyl-1-(2-phenoxyethyl)-1H-indol-3-yl]methyl}imidazo[1,2-a]pyridin-2-yl)-1-naphthoic acid,

(21) 2-[3-({1-[(3R)-3-hydroxy-3-phenylpropyl]-4-methyl-1H-indol-3-yl}methyl)imidazo[1,2-a]pyridin-2-yl]-1-naphthoic acid,

(22) 2-[3-({1-[(3S)-3-hydroxy-3-phenylpropyl]-4-methyl-1H-indol-3-yl}methyl)imidazo[1,2-a]pyridin-2-yl]-1-naphthoic acid,

(23) 2-[3-({1-[2-(4-fluorophenyl)ethyl]-4-methyl-1H-indol-3-yl}methyl)imidazo[1,2-a]pyridin-2-yl]-1-naphthoic acid,
(24) 2-[3-({4-methyl-1-[2-(tetrahydro-2H-pyran-4-yl)ethyl]-1H-indol-3-yl}methyl)imidazo[1,2-a]pyridin-2-yl]-1-naphthoic acid,
(25) 2-[3-({1-[2-(2,3-dihydro-1-benzofuran-5-yl)ethyl]-4-methyl-1H-indol-3-yl}methyl)imidazo[1,2-a]pyridin-2-yl]-1-naphthoic acid,
(26) 2-(3-{[4-methyl-1-(3-phenylpropyl)-1H-indol-3-yl]methyl}imidazo[1,2-a]pyridin-2-yl)-1-naphthoic acid,
(27) 2-(3-{[4-methyl-1-(piperidin-4-ylmethyl)-1H-indol-3-yl]methyl}imidazo[1,2-a]pyridin-2-yl)-1-naphthoic acid,
(28) 2-(3-{[1-(3-hydroxypropyl)-4-methyl-1H-indol-3-yl]methyl}imidazo[1,2-a]pyridin-2-yl)-1-naphthoic acid,
(29) 2-[3-({1-[2-(dipropan-2-ylamino)ethyl]-4-methyl-1H-indol-3-yl}methyl)imidazo[1,2-a]pyridin-2-yl]-1-naphthoic acid,
(30) 2-[3-({4-methyl-1-[2-(piperazin-1-yl)ethyl]-1H-indol-3-yl}methyl)imidazo[1,2-a]pyridin-2-yl]-1-naphthoic acid,
(31) 2-[3-({4-methyl-1-[2-(2-oxopyrrolidin-1-yl)ethyl]-1H-indol-3-yl}methyl)imidazo[1,2-a]pyridin-2-yl]-1-naphthoic acid,
(32) 2-[3-({1-[2-(1,1-dioxidethiomorpholin-4-yl)ethyl]-4-methyl-1H-indol-3-yl}methyl)imidazo[1,2-a]pyridin-2-yl]-1-naphthoic acid,
(33) 2-[3-({1-[2-(3,4-dihydroisoquinolin-2(1H)-yl)ethyl]-4-methyl-1H-indol-3-yl}methyl)imidazo[1,2-a]pyridin-2-yl]-1-naphthoic acid,
(34) 2-{3-[(1-{2-[2-(diethylamino)ethoxy]ethyl}-4-methyl-1H-indol-3-yl)methyl]imidazo[1,2-a]pyridin-2-yl}-1-naphthoic acid,
(35) 2-[3-({4-methyl-1-[2-(1-methyl-1H-pyrazol-4-yl)ethyl]-1H-indol-3-yl}methyl)imidazo[1,2-a]pyridin-2-yl]-1-naphthoic acid,
(36) 2-[3-[(1-{2-[2-(dimethylamino)ethoxy]ethyl}-4-methyl-1H-indol-3-yl)methyl]imidazo[1,2-a]pyridin-2-yl]-1-naphthoic acid,
(37) 2-(3-{[4-methyl-1-(4-methylpent-3-en-1-yl)-1H-indol-3-yl]methyl}imidazo[1,2-a]pyridin-2-yl)-1-naphthoic acid,
(38) 2-[3-({1-[2-(3-fluorophenyl)ethyl]-4-methyl-1H-indol-3-yl}methyl)imidazo[1,2-a]pyridin-2-yl]-1-naphthoic acid,
(39) 2-[3-({4-methyl-1-[2-(1H-pyrazol-1-yl)ethyl]-1H-indol-3-yl}methyl)imidazo[1,2-a]pyridin-2-yl]-1-naphthoic acid,
(40) 2-[3-({1-[2-(azepan-1-yl)ethyl]-4-methyl-1H-indol-3-yl}methyl)imidazo[1,2-a]pyridin-2-yl]-1-naphthoic acid,
(41) 2-{3-[(4-methyl-1-{2-[methyl(phenyl)amino]ethyl}-1H-indol-3-yl)methyl]imidazo[1,2-a]pyridin-2-yl}-1-naphthoic acid,
(42) 2-[3-({1-[2-(1H-imidazol-1-yl)ethyl]-4-methyl-1H-indol-3-yl}methyl)imidazo[1,2-a]pyridin-2-yl]-1-naphthoic acid,
(43) 2-[3-({4-methyl-1-[2-(pyridin-4-yl)ethyl]-1H-indol-3-yl}methyl)imidazo[1,2-a]pyridin-2-yl]-1-naphthoic acid,
(44) 2-[3-({1-[2-(2-methoxyethoxy)ethyl]-4-methyl-1H-indol-3-yl}methyl)imidazo[1,2-a]pyridin-2-yl]-1-naphthoic acid,
(45) 2-[3-({4-methyl-1-[2-(thiophen-3-yl)ethyl]-1H-indol-3-yl}methyl)imidazo[1,2-a]pyridin-2-yl]-1-naphthoic acid,
(46) 2-[3-({4-methyl-1-[2-(thiophen-2-yl)ethyl]-1H-indol-3-yl}methyl)imidazo[1,2-a]pyridin-2-yl]-1-naphthoic acid,
(47) 2-(3-{[4-methyl-1-(3-methylbut-3-en-1-yl)-1H-indol-3-yl]methyl}imidazo[1,2-a]pyridin-2-yl)-1-naphthoic acid,
(48) 2-[3-({4-methyl-1-[2-(2-oxoimidazolidin-1-yl)ethyl]-1H-indol-3-yl}methyl)imidazo[1,2-a]pyridin-2-yl]-1-naphthoic acid,
(49) 2-(3-{[1-(but-3-en-1-yl)-4-methyl-1H-indol-3-yl]methyl}imidazo[1,2-a]pyridin-2-yl)-1-naphthoic acid,
(50) 2-[3-({4-methyl-1-[(3Z)-pent-3-en-1-yl]-1H-indol-3-yl}methyl)imidazo[1,2-a]pyridin-2-yl]-1-naphthoic acid,
(51) 2-[3-({4-methyl-1-[3-(pyridin-2-yl)propyl]-1H-indol-3-yl}methyl)imidazo[1,2-a]pyridin-2-yl]-1-naphthoic acid,
(52) 2-(3-{[1-(3,4-dihydroxybutyl)-4-methyl-1H-indol-3-yl]methyl}imidazo[1,2-a]pyridin-2-yl)-1-naphthoic acid,
(53) 2-[3-({1-[2-(diethylamino)ethyl]-4-methyl-1H-indol-3-yl}methyl)imidazo[1,2-a]pyridin-2-yl]-1-naphthoic acid,
(54) 2-(3-{[1-(4-fluorobutyl)-4-methyl-1H-indol-3-yl]methyl}imidazo[1,2-a]pyridin-2-yl)-1-naphthoic acid,
(55) 2-(3-{[4-methyl-1-(4,4,4-trifluorobutyl)-1H-indol-3-yl]methyl}imidazo[1,2-a]pyridin-2-yl)-1-naphthoic acid,
(56) 2-(3-{[1-(4-hydroxybutyl)-4-methyl-1H-indol-3-yl]methyl}imidazo[1,2-a]pyridin-2-yl)-1-naphthoic acid,
(57) 2-(3-{[1-(3-fluoropropyl)-4-methyl-1H-indol-3-yl]methyl}imidazo[1,2-a]pyridin-2-yl)-1-naphthoic acid,
(58) 2-(3-{[4-methyl-1-(tetrahydro-2H-pyran-2-ylmethyl)-1H-indol-3-yl]methyl}imidazo[1,2-a]pyridin-2-yl)-1-naphthoic acid,
(59) 2-[3-({4-methyl-1-[3-(pyridin-3-yl)propyl]-1H-indol-3-yl}methyl)imidazo[1,2-a]pyridin-2-yl]-1-naphthoic acid,
(60) 2-[3-({4-methyl-1-[3-(pyridin-4-yl)propyl]-1H-indol-3-yl}methyl)imidazo[1,2-a]pyridin-2-yl]-1-naphthoic acid,
(61) 2-[3-({1-[3-(1H-imidazol-1-yl)propyl]-4-methyl-1H-indol-3-yl}methyl)imidazo[1,2-a]pyridin-2-yl]-1-naphthoic acid,
(62) 2-(3-{[1-(2-hydroxypropyl)-4-methyl-1H-indol-3-yl]methyl}imidazo[1,2-a]pyridin-2-yl)-1-naphthoic acid,
(63) 2-(3-{[1-(2-hydroxy-3-methoxypropyl)-4-methyl-1H-indol-3-yl]methyl}imidazo[1,2-a]pyridin-2-yl)-1-naphthoic acid,
(64) 2-(3-{[1-(2-hydroxy-2-methylpropyl)-4-methyl-1H-indol-3-yl]methyl}imidazo[1,2-a]pyridin-2-yl)-1-naphthoic acid, or
(65) 2-(3-{[1-(2-hydroxy-3-phenoxypropyl)-4-methyl-1H-indol-3-yl]methyl}imidazo[1,2-a]pyridin-2-yl)-1-naphthoic acid;

[8] a pharmaceutical composition containing the compound represented by the formula (I) in [1] above, a salt thereof, an N-oxide thereof or a solvate thereof, or a prodrug thereof as an active ingredient;

[9] the pharmaceutical composition according to [8] above, which is a chymase inhibitor;

[10] the pharmaceutical composition according to [8] above, which is an agent for preventing and/or treating chymase-mediated diseases;

[11] the pharmaceutical composition according to [10] above, wherein the chymase-mediated diseases are atopic dermatitis, ulcerative colitis, heart failure, pulmonary fibrosis, aneurysm, non-alcoholic steatohepatitis, peptic ulcer, or allergic conjunctivitis;

[12] a pharmaceutical composition comprising the compound represented by the formula (I) in [1] above, a salt thereof, an N-oxide thereof or a solvate thereof, or a prodrug thereof in combination with at least one kind selected from non-steroidal anti-inflammatory drugs, steroid drugs, immune suppressors, prostaglandins, anti-allergic drugs, mediator release inhibitors, leukotriene receptor antagonists, antihistamines, opioid agonists, phosphodiesterase inhibitors, forskolin preparations, nitric oxide synthase inhibitors, cannabinoid-2 receptor stimulants, decoy preparations, aminosalicylic acid preparations, diuretics, angiotensin converting enzyme inhibitors, angiotensin II receptor antagonists, anti-arrhythmic drugs, digitalis preparations, chymase inhibitors, renin inhibitors, calcium antagonists, beta blockers, nitrate drugs, anti-aldosterone drugs, cardiac stimulants, antiplatelet drugs, anticoagulants, antifibrotic drugs, antihyperglycemic drugs, antihypertensive drugs, lipid improvers, anti-obesity drugs, liver supporting drugs and antioxidants;

[13] a method for prevention and/or treatment of chymase-mediated diseases, comprising administering to a patient an effective amount of the compound represented by the formula (I) in [1] above, a salt thereof, an N-oxide thereof or a solvate thereof, or a prodrug thereof;

[14] a compound represented by the formula (I) in [1] above, a salt thereof, an N-oxide thereof or a solvate thereof, or a prodrug thereof, for the purpose of preventing and/or treating chymase-mediated diseases; and

[15] a use of the compound represented by the formula (I) in [1] above, a salt thereof, an N-oxide thereof or a solvate thereof, or a prodrug thereof for manufacturing an agent for preventing and/or treating chymase-mediated diseases.

Effect of the Invention

The compound of the present invention exhibits extremely strong chymase inhibitory activity not seen in the past. Moreover, because of the large gap (ratio) between chymase inhibitory activity and liver cell toxicity, the compound of the present invention is a drug reduced greatly in terms of side effect risk of hepatotoxicity. In addition, the compound of the present invention has excellent metabolic stability. Thus, the compound of the present invention is a drug with a profile that combines adequate chymase inhibitory activity, higher safety, high metabolic stability and the like.

BEST MODE FOR CARRYING OUT THE INVENTION

The detailed explanation of the present invention is described below.

In "a 6- to 10-membered monocyclic or bicyclic aromatic heterocycle" in the present invention, examples of the "6- to 10-membered monocyclic aromatic heterocycle" are pyridine, pyridazine, pyrimidine, and pyrazine.

In "a 6- to 10-membered monocyclic or bicyclic aromatic heterocycle" in the present invention, examples of the "6- to 10-membered bicyclic aromatic heterocycle" are quinoline, isoquinoline, cinnoline, quinazoline, and quinoxaline.

In "a $C_{1-10}$ alkyl group optionally substituted with $R^{11}$" represented by $R^2$ in the present invention, a "$C_{1-10}$ alkyl group" is a "linear or branched $C_{1-10}$ alkyl group". Examples of "linear or branched $C_{1-10}$ alkyl groups" are methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 1-ethylpropyl, 2-ethylpropyl, 2,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 3-ethylbutyl, 1-ethyl-2-methylpropyl, 1-methyl-2-ethylpropyl, 2-methyl-3-pentyl, 2,3-dimethylbutyl, n-heptyl, 5-methylhexyl, 4-methylhexyl, 3-methylhexyl, 2-methylhexyl, 1-methylhexyl, 4,4-dimethylpentyl, 3,4-dimethylpentyl, 2,4-dimethylpentyl, 1,4-dimethylpentyl, 2,3-dimethylpentyl, 1,3-dimethylpentyl, 1,2-dimethylpentyl, 2,3,3-trimethylbutyl, 4,4-dimethylpentyl, 3,3-dimethylpentyl, 2,2-dimethylpentyl, 1,1-dimethylpentyl, 1,3,3-trimethylbutyl, 1,2,3-trimethylbutyl, 1,2,2-trimethylbutyl, 1,1,2-trimethylbutyl, 4-ethylpentyl, 3-ethylpentyl, 2-ethylpentyl, 1-ethylpentyl, 3-methyl-3-ethylbutyl, 2-methyl-3-ethylbutyl, 1-methyl-3-ethylbutyl, 3-methyl-2-ethylbutyl, 2-methyl-2-ethylbutyl, 1-methyl-2-ethylbutyl, 3-methyl-1-ethylbutyl, 2-methyl-1-ethylbutyl, 1-methyl-1-ethylbutyl, 1-propylbutyl, n-octyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1-propylpentyl, 2-propylpentyl, 3-propylpentyl, 4-propylpentyl, n-nonyl, 1-methyloctyl, 2-methyloctyl, 3-methyloctyl, 4-methyloctyl, 5-methyloctyl, 6-methyloctyl, 7-methyloctyl, 1-ethylheptyl, 2-ethylheptyl, 3-ethylheptyl, 4-ethylheptyl, 5-ethylheptyl, 3-propylhexyl, 2-propylhexyl, 1-propylhexyl, 1-butylpentyl, n-decyl, 1-methylnonyl, 2-methylnonyl, 3-methylnonyl, 4-methylnonyl, 5-methylnonyl, 6-methylnonyl, 7-methylnonyl, 8-methylnonyl, 1-ethyloctyl, 2-ethyloctyl, 3-ethyloctyl, 4-ethyloctyl, 5-ethyloctyl, 6-ethyloctyl, 1-propylheptyl, 2-propylheptyl, 3-propylheptyl, 4-propylheptyl, 1-butylhexyl, and 2-butylhexyl.

In "a $C_{2-10}$ alkenyl group optionally substituted with $R^{11}$" represented by $R^2$ in the present invention, a "$C_{2-10}$ alkenyl group" is a "linear or branched $C_{2-10}$ alkenyl group". Examples of the "linear or branched $C_{2-10}$ alkenyl group" are vinyl, 1-propenyl, 2-propenyl, 1-butenyl, 2-butenyl, 3-butenyl, 1-methyl-1-propenyl, 2-methyl-1-propenyl, 1-methyl-2-propenyl, 2-methyl-2-propenyl, 1,2-dimethylvinyl, 1-ethylvinyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,2-dimethyl-1-propenyl, 1-ethyl-1-propenyl, 1-ethyl-2-propenyl, 2-ethyl-2-propenyl, 1,1-dimethyl-2-propenyl, 1-propylvinyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,2-dimethyl-1-butenyl, 1,3-dimethyl-1-butenyl, 2,3-dimethyl-1-butenyl, 3,3-dimethyl-1-butenyl, 1-ethyl-1-butenyl, 2-ethyl-1-butenyl, 3-ethyl-1-butenyl, 1,2-dimethyl-2-butenyl, 1,3-dimethyl-2-butenyl, 1,1-dimethyl-2-butenyl, 2,3-dimethyl-2-butenyl, 1-ethyl-2-butenyl, 2-ethyl-2-butenyl, 3-ethyl-2-butenyl, 1,1-dimethyl-3-butenyl, 1,2-dimethyl-3-butenyl, 1,3-dimethyl-3-butenyl, 2,2-dimethyl-3-butenyl, 2,3-dimethyl-3-butenyl, 1-ethyl-3-butenyl, 2-ethyl-3-butenyl, 3-ethyl-3-butenyl, 1-ethyl-2-methyl-1-propenyl, 1-heptenyl, 2-heptenyl, 3-heptenyl, 4-heptenyl, 5-heptenyl, 6-heptenyl, 1-methyl-5-hexenyl, 2-methyl-5-hexenyl, 3-methyl-5-hexenyl, 4-methyl-5-hexenyl, 5-methyl-5-hexenyl, 5-methyl-4-hexenyl, 4-methyl-4-hexenyl, 3-methyl-4-hexenyl, 2-methyl-4-hexenyl, 1-methyl-4-hexenyl, 5-methyl-3-hexenyl, 4-methyl-3-hexenyl, 3-methyl-3-hexenyl, 2-methyl-3-hexenyl, 1-methyl-3-hexenyl, 5-methyl-2-hexenyl, 4-methyl-2-hexenyl, 3-methyl-2-hexenyl, 2-methyl-2-hexenyl, 1-methyl-2-hexenyl, 5-methyl-1-hexenyl, 4-methyl-1-hexenyl, 3-methyl-1-hexenyl, 2-methyl-1-hexenyl, 1-methyl-1-hexenyl, 4-ethyl-4-pentenyl, 3-ethyl-4-pentenyl, 2-ethyl-4-pentenyl, 1-ethyl-4-pentenyl, 3-ethyl-1-pentenyl, 2-ethyl-1-pentenyl, 1-ethyl-1-pentenyl, 3-ethyl-3- pentenyl, 2-ethyl-3-pentenyl, 1-ethyl-3-pentenyl, 3-ethyl-2-pentenyl, 2-ethyl-2-pentenyl, 1-ethyl-2-pentenyl, 3-propyl-3-butenyl, 2-propyl-3-butenyl, 1-propyl-3-butenyl, 2-propyl-2-butenyl, 1-propyl-2-butenyl, 1-propyl-1-butenyl, 1-octenyl, 2-octenyl, 3-octenyl, 4-octenyl, 5-octenyl, 6-octenyl, 7-octenyl, 6-methyl-6-heptenyl, 5-methyl-6-heptenyl, 4-methyl-6-heptenyl, 3-methyl-6-heptenyl, 2-methyl-6-heptenyl, 1-methyl-6-heptenyl, 6-methyl-5-heptenyl, 5-methyl-5-heptenyl, 4-methyl-5-heptenyl, 3-methyl-5-heptenyl, 2-methyl-5-heptenyl, 1-methyl-5-heptenyl, 6-methyl-4-heptenyl, 5-methyl-4-heptenyl, 4-methyl-4-heptenyl, 3-methyl-4-heptenyl, 2-methyl-4-heptenyl, 1-methyl-4-heptenyl, 6-methyl-3-heptenyl, 5-methyl-3-heptenyl, 4-methyl-3-heptenyl, 3-methyl-3-heptenyl, 2-methyl-3-heptenyl, 1-methyl-3-heptenyl, 6-methyl-2-heptenyl, 5-methyl-2-heptenyl, 4-methyl-2-heptenyl, 3-methyl-2-heptenyl, 2-methyl-2-heptenyl, 1-methyl-2-heptenyl, 6-methyl-1-heptenyl, 5-methyl-1-heptenyl, 4-methyl-1-heptenyl, 3-methyl-1-heptenyl, 2-methyl-1-heptenyl, 1-methyl-1-heptenyl, 8-nonenyl, 7-nonenyl, 6-nonenyl, 5-nonenyl, 4-nonenyl, 3-nonenyl, 2-nonenyl, 1-nonenyl, 7-methyl-7-octenyl, 6-methyl-7-octenyl, 5-methyl-7-octenyl, 4-methyl-7-octenyl, 3-methyl-7-octenyl, 2-methyl-7-octenyl, 1-methyl-7-octenyl, 7-methyl-6-octenyl, 6-methyl-6-octenyl, 5-methyl-6-octenyl, 4-methyl-6-octenyl, 3-methyl-6-octenyl, 2-methyl-6-octenyl, 1-methyl-6-octenyl, 7-methyl-5-octenyl, 6-methyl-5-octenyl, 5-methyl-5-octenyl, 4-methyl-5-octenyl, 3-methyl-5-octenyl, 2-methyl-5-octenyl, 1-methyl-5-octenyl, 7-methyl-4-octenyl, 6-methyl-4-octenyl, 5-methyl-4-octenyl, 4-methyl-4-octenyl, 3-methyl-4-octenyl, 2-methyl-4-octenyl, 1-methyl-4-octenyl, 7-methyl-3-octenyl, 6-methyl-3-octenyl, 5-methyl-3-octenyl, 4-methyl-3-octenyl, 3-methyl-3-octenyl, 2-methyl-3-octenyl, 1-methyl-3-octenyl, 7-methyl-2-octenyl, 6-methyl-2-octenyl, 5-methyl-2-octenyl, 4-methyl-2-octenyl, 3-methyl-2-octenyl, 2-methyl-2-octenyl, 1-methyl-2-octenyl, 7-methyl-1-octenyl, 6-methyl-1-octenyl, 5-methyl-1-octenyl, 4-methyl-1-octenyl, 3-methyl-1-octenyl, 2-methyl-1-octenyl, 1-methyl-1-octenyl, 1-decenyl, 2-decenyl, 3-decenyl, 4-decenyl, 5-decenyl, 6-decenyl, 7-decenyl, 8-decenyl, 9-decenyl, 8-methyl-8-nonenyl, 7-methyl-8-nonenyl, 6-methyl-8-nonenyl, 5-methyl-8-nonenyl, 4-methyl-8-nonenyl, 3-methyl-8-nonenyl, 2-methyl-8-nonenyl, 1-methyl-8-nonenyl, 8-methyl-7-nonenyl, 7-methyl-7-nonenyl, 6-methyl-7-nonenyl, 5-methyl-7-nonenyl, 4-methyl-7-nonenyl, 3-methyl-7-nonenyl, 2-methyl-7-nonenyl, 1-methyl-7-nonenyl, 8-methyl-6-nonenyl, 7-methyl-6-nonenyl, 6-methyl-6-nonenyl, 5-methyl-6-nonenyl, 4-methyl-6-nonenyl, 3-methyl-6-nonenyl, 2-methyl-6-nonenyl, 1-methyl-6-nonenyl, 8-methyl-5-nonenyl, 7-methyl-5-nonenyl, 6-methyl-5-nonenyl, 5-methyl-5-nonenyl, 4-methyl-5-nonenyl, 3-methyl-5-nonenyl, 2-methyl-5-nonenyl, 1-methyl-5-nonenyl, 8-methyl-4-nonenyl, 7-methyl-4-nonenyl, 6-methyl-4-nonenyl, 5-methyl-4-nonenyl, 4-methyl-4-nonenyl, 3-methyl-4-nonenyl, 2-methyl-4-nonenyl, 1-methyl-4-nonenyl, 8-methyl-3-nonenyl, 7-methyl-3-nonenyl, 6-methyl-3-nonenyl, 5-methyl-3-nonenyl, 4-methyl-3-nonenyl, 3-methyl-3-nonenyl, 2-methyl-3-nonenyl, 1-methyl-3-nonenyl, 8-methyl-2-nonenyl, 7-methyl-2-nonenyl, 6-methyl-2-nonenyl, 5-methyl-2-nonenyl, 4-methyl-2-nonenyl, 3-methyl-2-nonenyl, 2-methyl-2-nonenyl, 1-methyl-2-nonenyl, 8-methyl-1-nonenyl, 7-methyl-1-nonenyl, 6-methyl-1-nonenyl, 5-methyl-1-nonenyl, 4-methyl-1-nonenyl, 3-methyl-1-nonenyl, 2-methyl-1-nonenyl, and 1-methyl-1-nonenyl.

In "a $C_{2-10}$ alkynyl group optionally substituted with $R^{11}$" represented by $R^2$ in the present invention, a "$C_{2-10}$ alkynyl group" is a "linear or branched $C_{2-10}$ alkynyl group".

Examples of the "linear or branched $C_{2-10}$ alkynyl group" are ethynyl, 1-propynyl, 2-propynyl, 1-methyl-2-propynyl, 1-butynyl, 2-butynyl, 3-butynyl, 1-pentynyl, 2-pentynyl, 3-pentynyl, 4-pentynyl, 3-methyl-1-butynyl, 1-methyl-2-butynyl, 2-methyl-3-butynyl, 1-methyl-3-butynyl, 1-hexynyl, 2-hexynyl, 3-hexynyl, 4-hexynyl, 5-hexynyl, 4-methyl-1-pentynyl, 3-methyl-1-pentynyl, 4-methyl-2-pentynyl, 1-methyl-2-pentynyl, 2-methyl-3-pentynyl, 1-methyl-3-pentynyl, 3-methyl-4-pentynyl, 2-methyl-4-pentynyl, 1-methyl-4-pentynyl, 1-ethyl-2-butynyl, 2-ethyl-3-butynyl, 1-ethyl-3-butynyl, 6-heptynyl, 5-heptynyl, 4-heptynyl, 3-heptynyl, 2-heptynyl, 1-heptynyl, 4-methyl-5-hexynyl, 3-methyl-5-hexynyl, 2-methyl-5-hexynyl, 1-methyl-5-hexynyl, 3-methyl-4-hexynyl, 2-methyl-4-hexynyl, 1-methyl-4-hexynyl, 5-methyl-3-hexynyl, 2-methyl-3-hexynyl, 1-methyl-3-hexynyl, 5-methyl-2-hexynyl, 4-methyl-2-hexynyl, 1-methyl-2-hexynyl, 5-methyl-1-hexynyl, 4-methyl-1-hexynyl, 3-methyl-1-hexynyl, 1-octynyl, 2-octynyl, 3-octynyl, 4-octynyl, 5-octynyl, 6-octynyl, 7-octynyl, 5-methyl-6-heptynyl, 4-methyl-6-heptynyl, 3-methyl-6-heptynyl, 2-methyl-6-heptynyl, 1-methyl-6-heptynyl, 4-methyl-5-heptynyl, 3-methyl-5-heptynyl, 2-methyl-5-heptynyl, 1-methyl-5-heptynyl, 6-methyl-4-heptynyl, 3-methyl-4-heptynyl, 2-methyl-4-heptynyl, 1-methyl-4-heptynyl, 6-methyl-3-heptynyl, 5-methyl-3-heptynyl, 2-methyl-3-heptynyl, 1-methyl-3-heptynyl, 6-methyl-2-heptynyl, 5-methyl-2-heptynyl, 4-methyl-2-heptynyl, 1-methyl-2-heptynyl, 6-methyl-1-heptynyl, 5-methyl-1-heptynyl, 4-methyl-1-heptynyl, 3-methyl-1-heptynyl, 1-nonynyl, 2-nonynyl, 3-nonynyl, 4-nonynyl, 5-nonynyl, 6-nonynyl, 7-nonynyl, 8-nonynyl, 6-methyl-7-octynyl, 5-methyl-7-octynyl, 4-methyl-7-octynyl, 3-methyl-7-octynyl, 2-methyl-7-octynyl, 1-methyl-7-octynyl, 5-methyl-6-octynyl, 4-methyl-6-octynyl, 3-methyl-6-octynyl, 2-methyl-6-octynyl, 1-methyl-6-octynyl, 7-methyl-5-octynyl, 4-methyl-5-octynyl, 3-methyl-5-octynyl, 2-methyl-5-octynyl, 1-methyl-5-octynyl, 7-methyl-4-octynyl, 6-methyl-4-octynyl, 3-methyl-4-octynyl, 2-methyl-4-octynyl, 1-methyl-4-octynyl, 7-methyl-3-octynyl, 6-methyl-3-octynyl, 5-methyl-3-octynyl, 2-methyl-3-octynyl, 1-methyl-3-octynyl, 7-methyl-2-octynyl, 6-methyl-2-octynyl, 5-methyl-2-octynyl, 4-methyl-2-octynyl, 1-methyl-2-octynyl, 7-methyl-1-octynyl, 6-methyl-1-octynyl, 5-methyl-1-octynyl, 4-methyl-1-octynyl, 3-methyl-1-octynyl, 1-decynyl, 2-decynyl, 3-decynyl, 4-decynyl, 5-decynyl, 6-decynyl, 7-decynyl, 8-decynyl, 9-decynyl, 7-methyl-8-nonynyl, 6-methyl-8-nonynyl, 5-methyl-8-nonynyl, 4-methyl-8-nonynyl, 3-methyl-8-nonynyl, 2-methyl-8-nonynyl, 1-methyl-8-nonynyl, 6-methyl-7-nonynyl, 5-methyl-7-nonynyl, 4-methyl-7-nonynyl, 3-methyl-7-nonynyl, 2-methyl-7-nonynyl, 1-methyl-7-nonynyl, 8-methyl-6-nonynyl, 5-methyl-6-nonynyl, 4-methyl-6-nonynyl, 3-methyl-6-nonynyl, 2-methyl-6-nonynyl, 1-methyl-6-nonynyl, 8-methyl-5-nonynyl, 7-methyl-5-nonynyl, 4-methyl-5-nonynyl, 3-methyl-5-nonynyl, 2-methyl-5-nonynyl, 1-methyl-5-nonynyl, 8-methyl-4-nonynyl, 7-methyl-4-nonynyl, 6-methyl-4-nonynyl, 3-methyl-4-nonynyl, 2-methyl-4-nonynyl, 1-methyl-4-nonynyl, 8-methyl-3-nonynyl, 7-methyl-3-nonynyl, 6-methyl-3-nonynyl, 5-methyl-3-nonynyl, 2-methyl-3-nonynyl, 1-methyl-3-nonynyl, 8-methyl-2-nonynyl, 7-methyl-2-nonynyl, 6-methyl-2-nonynyl, 5-methyl-2-nonynyl, 4-methyl-2-nonynyl, 1-methyl-2-nonynyl, 8-methyl-1-nonynyl, 7-methyl-1-nonynyl, 6-methyl-1-nonynyl, 5-methyl-1-nonynyl, 4-methyl-1-nonynyl, and 3-methyl-1-nonynyl.

In "a $C_{1-10}$ alkyl group optionally substituted with $R^{12}$" represented by $R^2$ in the present invention, examples of the "$C_{1-10}$ alkyl group" are the $C_{1-10}$ alkyl groups in the "$C_{1-10}$ alkyl group optionally substituted with $R^{11}$" represented by $R^2$.

In "a $C_{2-10}$ alkenyl group optionally substituted with $R^{12}$" represented by $R^2$ in the present invention, examples of the "$C_{2-10}$ alkenyl group" are the $C_{2-10}$ alkenyl groups in the "$C_{2-10}$ alkenyl group optionally substituted with $R^{11}$" represented by $R^2$.

In "a $C_{2-10}$ alkynyl group substituted with $R^{12}$" represented by $R^2$ in the present invention, examples of the "$C_{2-10}$ alkynyl group" are the $C_{2-10}$ alkynyl groups in the "$C_{2-10}$ alkynyl group optionally substituted with $R^{11}$" represented by $R^2$.

In "a $C_{1-6}$ alkyl group substituted with $R^{12}$" represented by $R^2$ in the present invention, a "$C_{1-6}$ alkyl group" is a "linear or branched $C_{1-6}$ alkyl group". Examples of the "linear or branched $C_{1-6}$ alkyl group" are methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, 1-ethylpropyl, 2-ethylpropyl, 2,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 3-ethylbutyl, 1-ethyl-2-methylpropyl, 1-methyl-2-ethylpropyl, 2-methyl-3-pentyl and 2,3-dimethylbutyl.

In "a $C_{2-6}$ alkenyl group optionally substituted with $R^{12}$" represented by $R^2$ in the present invention, a "$C_{2-6}$ alkenyl group" is a "linear or branched $C_{2-6}$ alkenyl group". Examples of the "linear or branched $C_{2-6}$ alkenyl group" are vinyl, 1-propenyl, 2-propenyl, 1-butenyl, 2-butenyl, 3-butenyl, 1-methyl-1-propenyl, 2-methyl-1-propenyl, 1-methyl-2-propenyl, 2-methyl-2-propenyl, 1,2-dimethylvinyl, 1-ethylvinyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,2-dimethyl-1-propenyl, 1-ethyl-1-propenyl, 1-ethyl-2-propenyl, 2-ethyl-2-propenyl, 1,1-dimethyl-2-propenyl, 1-propylvinyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,2-dimethyl-1-butenyl, 1,3-dimethyl-1-butenyl, 2,3-dimethyl-1-butenyl, 3,3-dimethyl-1-butenyl, 1-ethyl-1-butenyl, 2-ethyl-1-butenyl, 3-ethyl-1-butenyl, 1,2-dimethyl-2-butenyl, 1,3-dimethyl-2-butenyl, 1,1-dimethyl-2-butenyl, 2,3-dimethyl-2-butenyl, 1-ethyl-2-butenyl, 2-ethyl-2-butenyl, 3-ethyl-2-butenyl, 1,1-dimethyl-3-butenyl, 1,2-dimethyl-3-butenyl, 1,3-dimethyl-3-butenyl, 2,2-dimethyl-3-butenyl, 2,3-dimethyl-3-butenyl, 1-ethyl-3-butenyl, 2-ethyl-3-butenyl, 3-ethyl-3-butenyl, and 1-ethyl-2-methyl-1-propenyl.

In "a $C_{2-6}$ alkynyl optionally substituted with $R^{12}$" represented by $R^2$ in the present invention, a "$C_{2-6}$ alkynyl" is a "linear or branched $C_{2-6}$ alkynyl". Examples of the "linear or branched $C_{2-6}$ alkynyl" are ethynyl, 1-propynyl, 2-propynyl, 1-methyl-2-propynyl, 1-butynyl, 2-butynyl, 3-butynyl, 1-pentynyl, 2-pentynyl, 3-pentynyl, 4-pentynyl, 3-methyl-1-butynyl, 1-methyl-2-butynyl, 2-methyl-3-butynyl, 1-methyl-3-butynyl, 1-hexynyl, 2-hexynyl, 3-hexynyl, 4-hexynyl, 5-hexynyl, 4-methyl-1-pentynyl, 3-methyl-1-pentynyl, 4-methyl-2-pentynyl, 1-methyl-2-pentynyl, 2-methyl-3-pentynyl, 1-methyl-3-pentynyl, 3-methyl-4-pentynyl, 2-methyl-4-pentynyl, 1-methyl-4-pentynyl, 1-ethyl-2-butynyl, 2-ethyl-3-butynyl, and 1-ethyl-3-butynyl.

A "$C_{1-2}$ alkyl group" represented by $R^4$ in the present invention is a methyl or ethyl.

A "$C_{1-3}$ alkyl group" represented by $R^5$, $R^6$, $R^8$, $R^9$, and $R^{10}$ in the present invention is a methyl, ethyl, n-propyl or isopropyl.

A "$C_{1-4}$ alkyl group" represented by $R^7$ in the present invention is a methyl, ethyl, n-propyl, isopropyl, n-butyl, sec-butyl, tert-butyl or isobutyl group.

Examples of a "$C_{1-3}$ haloalkyl group" represented by $R^5$, $R^6$, and $R^8$ in the present invention are monofluoromethyl, difluoromethyl, trifluoromethyl, 2-fluoroethyl, 1-fluoroethyl, 2,2-difluoroethyl, 1,2-difluoroethyl, 1,1-difluoroethyl, 2,2,2-trifluoroethyl, 1,2,2-trifluoroethyl, 1,1,2-trifluoroethyl, 1,2,2,2-tetrafluoroethyl, 1,1,2,2-tetrafluoroethyl, pentafluoroethyl, 1,2-dibromo-1,2,2-trifluoroethyl, 1-chloro-1,2,2,2-tetrafluoroethyl, 3-fluoropropyl, 3-chloropropyl, 2-fluoropropyl, 2-chloropropyl, 1-fluoropropyl, 1-chloropropyl, 3,3-difluoropropyl, 2,3-difluoropropyl, 1,3-difluoropropyl, 1,2-difluoropropyl, 2,2-difluoropropyl, 1,1-difluoropropyl, 3,3,3-trifluoropropyl, 2,3,3-trifluoropropyl, 1,3,3-trifluoropropyl, 1,2,2-trifluoropropyl, 1,1,2-trifluoropropyl, 1,1,3-trifluorpropyl, 1,1,2,2-tetrafluoropropyl, and 2,2,3,3,3-pentafluoropropyl.

Examples of a "$C_{1-2}$ haloalkyl group" represented by $R^4$ in the present invention are monofluoromethyl, difluoromethyl, trifluoromethyl, 2-fluoroethyl, 1-fluoroethyl, 2,2-difluoroethyl, 1,2-difluoroethyl, 1,1-difluoroethyl, 2,2,2-trifluoroethyl, 1,2,2-trifluoroethyl, 1,1,2-trifluoroethyl, 1,2,2,2-tetrafluoroethyl, 1,1,2,2-tetrafluoroethyl, pentafluoroethyl, 1,2-dibromo-1,2,2-trifluoroethyl, and 1-chloro-1,2,2,2-tetrafluoroethyl.

Examples of a "$C_{1-3}$ alkoxy group" represented by $R^8$ in the present invention are methoxy, ethoxy, n-propoxy, and isopropoxy.

Examples of a "$C_{5-6}$ carbocycle" represented by $R^8$ in the present invention are cyclopentyl, cyclopentenyl, cyclopentadienyl, cyclohexyl, cyclohexenyl, cyclohexadienyl, and phenyl.

Examples of a "5- to 6-membered heterocycle containing 1 to 2 nitrogen atoms, 1 oxygen atom and/or 1 optionally oxidized sulfur atom" represented by $R^8$ in the present invention are pyrrolidyl, tetrahydrofuranyl, thiolanyl, sulfolanyl, piperidinyl, tetrahydropyranyl, tetrahydrothiopyranyl, 1,1-dioxohexahydrothiopyranyl, hexahydropyrimidinyl, piperadinyl, morpholinyl, thiomorpholinyl, 1,1-dioxothiomorpholinyl, pyrrolinyl, furanyl, thiofuranyl, pyrazolinyl, imidazolinyl, isoxazolinyl, oxazolinyl, isothiazolinyl, thiazolinyl, pyridinyl, pyridazinyl, pyrimidinyl, and pyrazinyl.

In a "$C_{5-6}$ carbocycle optionally substituted with at least one selected from a halogen atom, oxo group and methyl group" represented by $R^{11}$ in the present invention, the "$C_{5-6}$ carbocycle" is given as a "$C_{5-6}$ carbocycle" represented by $R^8$.

In a "3- to 10-membered heterocycle containing 1 to 4 nitrogen atoms, 1 to 2 oxygen atoms and/or 1 to 2 sulfur atoms, optionally substituted with at least one group selected from a halogen atom, an oxo group and a methyl group" represented by $R^{11}$ in the present invention, examples of the "3- to 10-membered heterocycle containing 1 to 4 nitrogen atoms, 1 to 2 oxygen atoms and/or 1 to 2 sulfur atoms" are aziridinyl, oxiranyl, thiiranyl, azetidinyl, oxetanyl, thietanyl, azepanyl, oxepanyl, thiepanyl, 1,4-diazepanyl, 1,4-oxazepanyl, azacyclooctanyl, 1,5-diazacyclooctanyl, pyrrolidyl, tetrahydrofuranyl, thiolanyl, sulfolanyl, piperidinyl, tetrahydropyranyl, tetrahydrothiopyranyl, 1,1-dioxohexahydrothiopyranyl, hexahydropyrimidinyl, piperadinyl, morpholinyl, thiomorpholinyl, 1,1-dioxothiomorpholinyl, 1,3-dioxanyl, 1,4-dioxanyl, 1,3-dithianyl, 1,4-dithianyl, pyrrolinyl, furanyl, thiofuranyl, pyrazolinyl, imidazolinyl, isooxazolinyl, oxazolinyl, isothiazolinyl, thiazolinyl, pyridinyl, pyridazinyl, pyrimidinyl, pyrazinyl, 2,3-dihydrobenzofuranyl, indolinyl, benzothiazolinyl, 2,3-dihydro-1H-indazolinyl, tetrahydrobenzimidazolinyl, 2,3-dihydrofuro[3,2-b]pyridinyl, 2,3-dihydrofuro[2,3-b]pyridinyl, 2,3-dihydrothieno[2,3-b]pyridinyl, 2,3-dihydro-1H-pyrrolo[2,3-b]pyridinyl, 2,3-benzofuranyl, benzo[b]thiophenyl, indolinyl, 1,2-benzisoxazolinyl, benzoxazolinyl, 1,2-benzisothiazolinyl, benzothiazolinyl, indazolinyl, benzimidazolinyl, furo[2,3-b]pyridinyl, furo[2,3-c]pyridinyl, furo[3,2-c]pyridinyl, furo[3,2-b]pyridinyl, thieno[2,3-b]pyridinyl, thieno[2,3-b]pyridinyl, thieno[3,2-c]pyridinyl, thieno[2,3-c]pyridinyl, thieno[3,2-b]pyridinyl, 7-azaindolinyl, 6-azaindole, 5-azaindolinyl, 4-azaindolinyl, isoxazolo[5,4-b]pyridinyl, isoxazolo[5,4-c]pyridinyl, isoxazolo[4,5-b]pyridinyl, isothiazolo[5,4-b]pyridinyl, oxazolo[5,4-b]pyridinyl, oxazolo[5,4-c]pyridinyl, oxazolo[4,5-c]pyridinyl, oxazolo[4,5-b]pyridinyl, thiazolo[5,4-b]pyridinyl, thiazolo[5,4-c]pyridinyl, thiazolo[4,5-c]pyridinyl, thiazolo[4,5-b]pyridinyl, 1H-pyrazolo[3,4-b]pyridinyl, 1H-pyrazolo[3,4-c]pyridinyl, 1H-pyrazolo[4,3-c]pyridinyl, 1H-pyrazolo[4,3-b]pyridinyl, 3H-imidazo[4,5-b]pyridinyl, 3H-imidazo[4,5-c]pyridinyl, 5-azabenzimidazolinyl, 4-azabenzimidazolinyl, 3,4-dihydro-(2H)-1-benzopyranyl, isochromanyl, 1,2,3,4-tetrahydroquinoline, 1,2,3,4-tetrahydroisoquinoline, 3,4-dihydro-2H-pyrano[2,3-b]pyridinyl, 3,4-dihydro-2H-pyrano[2,3-c]pyridinyl, 3,4-dihydro-2H-pyrano[3,2-c]pyridinyl, 3,4-dihydro-2H-pyrano[3,2-b]pyridinyl, 7,8-dihydro-5H-pyrano[4,3-b]pyridinyl, 1,2,3,4-tetrahydro-1,8-naphthyridinyl, 1,2,3,4-tetrahydro-1,7-naphthyridinyl, 1,2,3,4-tetrahydro-1,6-naphthyridinyl, 1,2,3,4-tetrahydro-1,5-naphthyridinyl, 5,6,7,8-tetrahydro-1,7-naphthyridinyl, 1,2,3,4-tetrahydro-2,7-naphthyridinyl, 1,2,3,4-tetrahydro-2,6-naphthyridinyl, 5,6,7,8-tetrahydro-1,6-naphthyridinyl, 3,4-dihydro-2H-benzo[e][1,3]oxazinyl, 3,4-dihydro-2H-1,4-benzoxazinyl, 3,4-dihydro-2H-1,4-benzothiazinyl, 2,3-dihydro-1H-pyrido[2,3-b][1,4]oxazinyl, 2,3-dihydro-1H-pyrido[3,4-b][1,4]oxazinyl, 3,4-dihydro-2H-pyrido[4,3-b][1,4]oxazinyl, 3,4-dihydro-2H-pyrido[3,2-b][1,4]oxazinyl, 1,4-benzodioxanyl, 2,3-dihydro-1,4-benzodithinyl, 3,4-dihydro-2H-1,4-benzothiazinyl, 2,3-dihydro-1,4-dioxino[2,3-b]pyridinyl, 2H-chromenyl, 2H-pyrano[2,3-c]pyridinyl, 2H-pyrano[3,2-c]pyridinyl, 2H-pyrano[3,2-b]pyridinyl, benzoxazinyl and 2H-pyrido[4,3-b]-1,4-oxazinyl.

In the present invention, $R^{12}$ is a halogen atom, hydroxyl group, dimethylamino group, pyrrolidinyl group, N-methylpyrrolidinyl group, piperidinyl group, phenoxy group optionally substituted with halogen atoms, phenyl group optionally substituted with halogen atoms, tetrahydropyranyl group, 2,3-dihydrobenzofuranyl group, thiophenyl group, diisopropylamino group, methyl(phenyl)amino group, piperadinyl group, 2-oxo-1-pyrrolidinyl group, morpholinyl group, 1,1-dioxothiomorpholinyl group, imidazolyl group, pyridyl group, 2-methoxyethyleneoxy group, dimethylaminoethyleneoxy group, diethylaminoethyleneoxy group, 1,2,3,4-tetrahydroisoquinolinyl group, azepanyl group, pyrazolyl group, 2-oxoimidazolidinyl group, diethylamino group, methoxy group or N-methylpyrazolyl group.

In the present invention, "halogen atoms" are fluorine, chlorine, bromine and iodine atoms.

In the present invention, $R^1$ is preferably a hydrogen atom.

In the present invention, $R^2$ is preferably a hydrogen atom, $C_{1-10}$ alkyl group optionally substituted with 1 to 6 of $R^{12}$, $C_{2-10}$ alkenyl optionally substituted with 1 to 6 of $R^{12}$ or $C_{2-10}$ alkynyl optionally substituted with 1 to 6 of $R^{12}$. More preferably, $R^{12}$ is a hydrogen atom, methyl group, ethyl group, n-propyl group, isopropyl group, $C_{1-6}$ alkyl substituted with 1 to 6 of $R^{12}$, $C_{2-6}$ alkenyl optionally substituted with 1 to 6 of $R^{12}$ or $C_{2-6}$ alkynyl optionally substituted with 1 to 6 of $R^{12}$. $R^2$ is still more preferably a hydrogen atom, methyl group, ethyl group or 2-(4-morpholinyl)ethyl group.

In the present invention, $R^3$ is preferably a hydrogen atom or methyl group. More preferably, $R^3$ is methyl group.

In the present invention, $R^4$ is preferably a hydrogen atom, methyl group, fluorine atom or chlorine atom. More preferably, $R^4$ is a fluorine atom.

In the present invention, $R^5$ is preferably a hydrogen atom, methyl group or fluorine atom. More preferably, $R^5$ is a hydrogen atom or fluorine atom.

In the present invention, $R^6$ is preferably a hydrogen atom, methyl group or fluorine atom. More preferably, $R^6$ is a hydrogen atom.

In the present invention, $R^7$ is preferably a hydrogen atom or methyl group. More preferably, $R^7$ is a hydrogen atom.

In the present invention, $R^8$ is preferably a hydrogen atom, $C_{1-3}$ alkyl, $C_{5-6}$ carbocycle, $C_{1-3}$ alkyl substituted with a $C_{1-3}$ alkoxy or $C_{1-3}$ alkyl substituted with $NR^9R^{10}$. More preferably, $R^8$ is a hydrogen atom, methyl group, phenyl group or methoxyethyl group or an ethyl group substituted with $NR^9R^{10}$.

In the present invention, $R^9$ and $R^{10}$ are preferably methyl, ethyl, isopropyl or phenyl.

In the present invention, $R^{11}$ is preferably a fluorine atom, hydroxyl group, dimethylamino group, pyrrolidinyl group, N-methylpyrrolidinyl group, piperidinyl group, phenoxy group, phenyl group, phenyl group substituted with fluorine atoms, tetrahydropyranyl group, 2,3-dihydrobenzofuranyl group, thiophenyl group, diisopropylamino group, methyl(phenyl)amino group, piperazinyl group, 2-oxo-1-pyrrolidinyl group, morpholinyl group, 1,1-dioxothiomorpholinyl group, imidazolyl group, pyridyl group, 2-methoxyethyleneoxy group, dimethylaminoethyleneoxy group, diethylaminoethyleneoxy group, 1,2,3,4-tetrahydroisoquinolinyl group, azepanyl group, pyrazolyl group, 2-oxoimidazolidinyl group, diethylamino group, methoxy group, or N-methylpyrazolyl group.

In the present invention, $R^{12}$ is preferably a fluorine atom, hydroxyl group, dimethylamino group, pyrrolidinyl group, N-methylpyrrolidinyl group, piperidinyl group, phenoxy group, phenyl group, phenyl group substituted with fluorine atoms, tetrahydropyranyl group, 2,3-dihydrobenzofuranyl group, thiophenyl group, diisopropylamino group, methyl(phenyl)amino group, piperazinyl group, 2-oxo-1-pyrrolidinyl group, morpholinyl group, 1,1-dioxothiomorpholinyl group, imidazolyl group, pyridyl group, 2-methoxyethyleneoxy group, dimethylaminoethyleneoxy group, diethylaminoethyleneoxy group, 1,2,3,4-tetrahydroisoquinolinyl group, azepanyl group, pyrazolyl group, 2-oxoimidazolidinyl group, diethylamino group, methoxy group, or N-methylpyrazolyl group.

In the present invention, $R^{4-a}$ is preferably a hydrogen atom, methyl group, fluorine atom or chlorine atom. A fluorine atom is more preferred as $R^{4-a}$.

In the present invention, $R^{5-a}$ is preferably a hydrogen atom, methyl group or fluorine atom. A hydrogen atom or fluorine atom is more preferred as $R^{5-a}$.

In the present invention, benzene, naphthalene, pyridine, pyrimidine, pyridazine, pyrazine, quinoline or isoquinoline ring is preferred as the ring represented by:

and benzene or naphthalene ring is especially preferred.

In the present invention, a compound represented by:

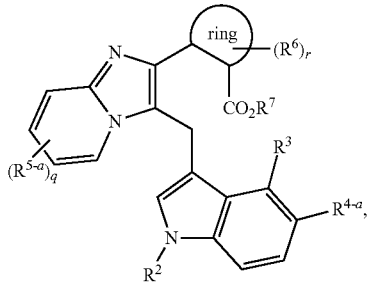
(I-a)

wherein all symbols have the same meaning as in [2] above,
a salt thereof, an N-oxide thereof or a solvate thereof, or a prodrug thereof is preferred as the compound represented by the formula (I), and a compound represented by:

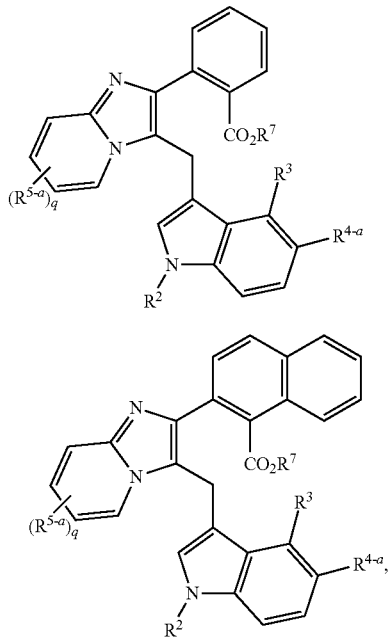
(I-b)
or
(I-c)

wherein all symbols have the same meaning as in [2] above,
a salt thereof, an N-oxide thereof or a solvate thereof, or a prodrug thereof is more preferred, and a compound represented by:

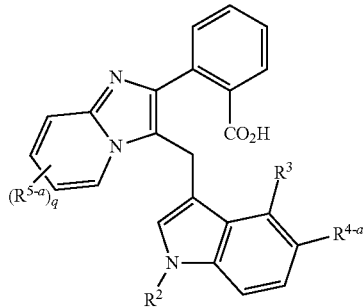
(I-d)
or
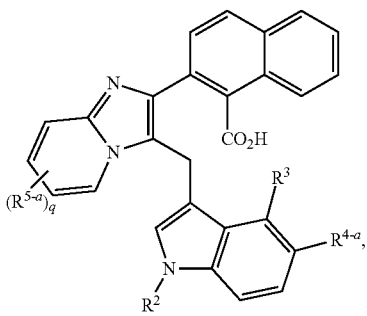
(I-e)

wherein all symbols have the same meaning as in [2] above,
a salt thereof, an N-oxide thereof or a solvate thereof, or a prodrug thereof is even more preferred.

2-{3-[(4-methyl-1H-indol-3-yl)methyl]imidazo[1,2-a]pyridin-2-yl}-1-naphthoic acid,
2-{3-[(1,4-dimethyl-1H-indol-3-yl)methyl]-6-methylimidazo[1,2-a]pyridin-2-yl}benzoic acid, 2-{3-[(1,4-dimethyl-1H-indol-3-yl)methyl]imidazo[1,2-a]pyridin-2-yl}benzoic acid,
2-{3-[(1-ethyl-4-methyl-1H-indol-3-yl)methyl]imidazo[1,2-a]pyridin-2-yl}benzoic acid,
2-{6-fluoro-3-[(4-methyl-1H-indol-3-yl)methyl]imidazo[1,2-a]pyridin-2-yl}-1-naphthoic acid,
2-{3-[(5-fluoro-4-methyl-1H-indol-3-yl)methyl]imidazo[1,2-a]pyridin-2-yl}benzoic acid,
2-[3-({4-methyl-1-[2-(4-morpholinyl)ethyl]-1H-indol-3-yl}methyl)imidazo[1,2-a]pyridin-2-yl]-1-naphthoic acid,
2-(3-{[4-methyl-1-(2-propanyl)-1H-indol-3-yl]methyl}imidazo[1,2-a]pyridin-2-yl)-1-naphthoic acid,
2-{3-[(4-methyl-1-propyl-1H-indol-3-yl)methyl]imidazo[1,2-a]pyridin-2-yl}-1-naphthoic acid,
2-{3-[(1-ethyl-4-methyl-1H-indol-3-yl)methyl]imidazo[1,2-a]pyridin-2-yl}-1-naphthoic acid,
2-{3-[(5-fluoro-4-methyl-1H-indol-3-yl)methyl]imidazo[1,2-a]pyridin-2-yl}-1-naphthoic acid,
2-(3-{[1-(2-hydroxyethyl)-4-methyl-1H-indol-3-yl]methyl}imidazo[1,2-a]pyridin-2-yl)-1-naphthoic acid,
2-[3-({1-[3-(dimethylamino)-2-hydroxypropyl]-4-methyl-1H-indol-3-yl}methyl)imidazo[1,2-a]pyridin-2-yl]-1-naphthoic acid,
2-(3-{[1-(2,3-dihydroxypropyl)-4-methyl-1H-indol-3-yl]methyl}imidazo[1,2-a]pyridin-2-yl)-1-naphthoic acid,
2-[3-({1-[2-(dimethylamino)ethyl]-4-methyl-1H-indol-3-yl}methyl)imidazo[1,2-a]pyridin-2-yl]-1-naphthoic acid,
2-[3-({1-[3-(dimethylamino)propyl]-4-methyl-1H-indol-3-yl}methyl)imidazo[1,2-a]pyridin-2-yl]-1-naphthoic acid,
2-[3-({4-methyl-1-[2-(pyrrolidin-1-yl)ethyl]-1H-indol-3-yl}methyl)imidazo[1,2-a]pyridin-2-yl]-1-naphthoic acid, 2-[3-({4-methyl-1-[2-(1-methylpyrrolidin-2-yl)ethyl]-1H-indol-3-yl}methyl)imidazo[1,2-a]pyridin-2-yl]-1-naphthoic acid,
2-[3-({4-methyl-1-[2-(piperidin-1-yl)ethyl]-1H-indol-3-yl}methyl)imidazo[1,2-a]pyridin-2-yl]-1-naphthoic acid,
2-(3-{[4-methyl-1-(2-phenoxyethyl)-1H-indol-3-yl]methyl}imidazo[1,2-a]pyridin-2-yl)-1-naphthoic acid,
2-[3-({1-[(3R)-3-hydroxy-3-phenylpropyl]-4-methyl-1H-indol-3-yl}methyl)imidazo[1,2-a]pyridin-2-yl]-1-naphthoic acid,
2-[3-({1-[(3S)-3-hydroxy-3-phenylpropyl]-4-methyl-1H-indol-3-yl}methyl)imidazo[1,2-a]pyridin-2-yl]-1-naphthoic acid,
2-[3-({1-[2-(4-fluorophenyl)ethyl]-4-methyl-1H-indol-3-yl}methyl)imidazo[1,2-a]pyridin-2-yl]-1-naphthoic acid,
2-[3-({4-methyl-1-[2-(tetrahydro-2H-pyran-4-yl)ethyl]-1H-indol-3-yl}methyl)imidazo[1,2-a]pyridin-2-yl]-1-naphthoic acid,
2-[3-({1-[2-(2,3-dihydro-1-benzofuran-5-yl)ethyl]-4-methyl-1H-indol-3-yl}methyl)imidazo[1,2-a]pyridin-2-yl]-1-naphthoic acid,
2-(3-{[4-methyl-1-(3-phenylpropyl)-1H-indol-3-yl]methyl}imidazo[1,2-a]pyridin-2-yl)-1-naphthoic acid,
2-(3-{[4-methyl-1-(piperidin-4-ylmethyl)-1H-indol-3-yl]methyl}imidazo[1,2-a]pyridin-2-yl)-1-naphthoic acid,
2-(3-{[1-(3-hydroxypropyl)-4-methyl-1H-indol-3-yl]methyl}imidazo[1,2-a]pyridin-2-yl)-1-naphthoic acid,
2-[3-({1-[2-(dipropan-2-ylamino)ethyl]-4-methyl-1H-indol-3-yl}methyl)imidazo[1,2-a]pyridin-2-yl]-1-naphthoic acid,
2-[3-({4-methyl-1-[2-(piperazin-1-yl)ethyl]-1H-indol-3-yl}methyl)imidazo[1,2-a]pyridin-2-yl]-1-naphthoic acid,
2-[3-({4-methyl-1-[2-(2-oxopyrrolidin-1-yl)ethyl]-1H-indol-3-yl}methyl)imidazo[1,2-a]pyridin-2-yl]-1-naphthoic acid,
2-[3-({1-[2-(1,1-dioxidethiomorpholin-4-yl)ethyl]-4-methyl-1H-indol-3-yl}methyl)imidazo[1,2-a]pyridin-2-yl]-1-naphthoic acid,
2-[3-({1-[2-(3,4-dihydroisoquinolin-2(1H)-yl)ethyl]-4-methyl-1H-indol-3-yl}methyl)imidazo[1,2-a]pyridin-2-yl]-1-naphthoic acid,
2-{3-[(1-{2-[2-(diethylamino)ethoxy]ethyl}-4-methyl-1H-indol-3-yl)methyl]imidazo[1,2-a]pyridin-2-yl}-1-naphthoic acid,
2-[3-({4-methyl-1-[2-(1-methyl-1H-pyrazol-4-yl)ethyl]-1H-indol-3-yl}methyl)imidazo[1,2-a]pyridin-2-yl]-1-naphthoic acid,
2-{3-[(1-{2-[2-(dimethylamino)ethoxy]ethyl}-4-methyl-1H-indol-3-yl)methyl]imidazo[1,2-a]pyridin-2-yl}-1-naphthoic acid,
2-(3-{[4-methyl-1-(4-methylpent-3-en-1-yl)-1H-indol-3-yl]methyl}imidazo[1,2-a]pyridin-2-yl)-1-naphthoic acid,
2-[3-({1-[2-(3-fluorophenyl)ethyl]-4-methyl-1H-indol-3-yl}methyl)imidazo[1,2-a]pyridin-2-yl]-1-naphthoic acid,
2-[3-({4-methyl-1-[2-(1H-pyrazol-1-yl)ethyl]-1H-indol-3-yl}methyl)imidazo[1,2-a]pyridin-2-yl]-1-naphthoic acid,
2-[3-({1-[2-(azepan-1-yl)ethyl]-4-methyl-1H-indol-3-yl}methyl)imidazo[1,2-a]pyridin-2-yl]-1-naphthoic acid,
2-{3-[(4-methyl-1-{2-[methyl(phenyl)amino]ethyl}-1H-indol-3-yl)methyl]imidazo[1,2-a]pyridin-2-yl}-1-naphthoic acid,
2-[3-({1-[2-(1H-imidazol-1-yl)ethyl]-4-methyl-1H-indol-3-yl}methyl)imidazo[1,2-a]pyridin-2-yl]-1-naphthoic acid,
2-[3-({4-methyl-1-[2-(pyridin-4-yl)ethyl]-1H-indol-3-yl}methyl)imidazo[1,2-a]pyridin-2-yl]-1-naphthoic acid,
2-[3-({1-[2-(2-methoxyethoxy)ethyl]-4-methyl-1H-indol-3-yl}methyl)imidazo[1,2-a]pyridin-2-yl]-1-naphthoic acid,
2-[3-({4-methyl-1-[2-(thiophen-3-yl)ethyl]-1H-indol-3-yl}methyl)imidazo[1,2-a]pyridin-2-yl]-1-naphthoic acid,
2-[3-({4-methyl-1-[2-(thiophen-2-yl)ethyl]-1H-indol-3-yl}methyl)imidazo[1,2-a]pyridin-2-yl]-1-naphthoic acid,
2-(3-{[4-methyl-1-(3-methylbut-3-en-1-yl)-1H-indol-3-yl]methyl}imidazo[1,2-a]pyridin-2-yl)-1-naphthoic acid,
2-[3-({4-methyl-1-[2-(2-oxoimidazolidin-1-yl)ethyl]-1H-indol-3-yl}methyl)imidazo[1,2-a]pyridin-2-yl]-1-naphthoic acid,
2-(3-{[1-(but-3-en-1-yl)-4-methyl-1H-indol-3-yl]methyl}imidazo[1,2-a]pyridin-2-yl)-1-naphthoic acid,
2-[3-({4-methyl-1-[(3Z)-pent-3-en-1-yl]-1H-indol-3-yl}methyl)imidazo[1,2-a]pyridin-2-yl]-1-naphthoic acid,
2-[3-({4-methyl-1-[3-(pyridin-2-yl)propyl]-1H-indol-3-yl}methyl)imidazo[1,2-a]pyridin-2-yl]-1-naphthoic acid,
2-(3-{[1-(3,4-dihydroxybutyl)-4-methyl-1H-indol-3-yl]methyl}imidazo[1,2-a]pyridin-2-yl)-1-naphthoic acid,
2-[3-({1-[2-(diethylamino)ethyl]-4-methyl-1H-indol-3-yl}methyl)imidazo[1,2-a]pyridin-2-yl]-1-naphthoic acid,
2-(3-{[1-(4-fluorobutyl)-4-methyl-1H-indol-3-yl]methyl}imidazo[1,2-a]pyridin-2-yl)-1-naphthoic acid,
2-(3-{[4-methyl-1-(4,4,4-trifluorobutyl)-1H-indol-3-yl]methyl}imidazo[1,2-a]pyridin-2-yl)-1-naphthoic acid,
2-(3-{[1-(4-hydroxybutyl)-4-methyl-1H-indol-3-yl]methyl}imidazo[1,2-a]pyridin-2-yl)-1-naphthoic acid,
2-(3-{[1-(3-fluoropropyl)-4-methyl-1H-indol-3-yl]methyl}imidazo[1,2-a]pyridin-2-yl)-1-naphthoic acid,
2-(3-{[4-methyl-1-(tetrahydro-2H-pyran-2-ylmethyl)-1H-indol-3-yl]methyl}imidazo[1,2-a]pyridin-2-yl)-1-naphthoic acid,
2-[3-({4-methyl-1-[3-(pyridin-3-yl)propyl]-1H-indol-3-yl}methyl)imidazo[1,2-a]pyridin-2-yl]-1-naphthoic acid,
2-[3-({4-methyl-1-[3-(pyridin-4-yl)propyl]-1H-indol-3-yl}methyl)imidazo[1,2-a]pyridin-2-yl]-1-naphthoic acid,
2-[3-({1-[3-(1H-imidazol-1-yl)propyl]-4-methyl-1H-indol-3-yl}methyl)imidazo[1,2-a]pyridin-2-yl]-1-naphthoic acid,
2-(3-{[1-(2-hydroxypropyl)-4-methyl-1H-indol-3-yl]methyl}imidazo[1,2-a]pyridin-2-yl)-1-naphthoic acid,
2-(3-{[1-(2-hydroxy-3-methoxypropyl)-4-methyl-1H-indol-3-yl]methyl}imidazo[1,2-a]pyridin-2-yl)-1-naphthoic acid,
2-(3-{[1-(2-hydroxy-2-methylpropyl)-4-methyl-1H-indol-3-yl]methyl}imidazo[1,2-a]pyridin-2-yl)-1-naphthoic acid, or
2-(3-{[1-(2-hydroxy-3-phenoxypropyl)-4-methyl-1H-indol-3-yl]methyl}imidazo[1,2-a]pyridin-2-yl)-1-naphthoic acid, a salt thereof, an N-oxide thereof or a solvate thereof, or a prodrug thereof is most preferred.

Unless otherwise specifically mentioned, all isomers are included in the present invention. For example, alkyl includes straight chain and branched ones. Moreover, all of isomers due to presence of asymmetric carbon(s) etc. (R-, S-, α- and β-configuration, enantiomer and diastereomer), optically active compounds having optical rotation (D-, L-, d- and l-forms), polar compound by chromatographic separation (more polar compound and less polar compound), equilibrium compounds, rotational isomers, a mixture thereof in any proportion and a racemic mixture are included in the present invention.

According to the present invention, unless otherwise indicated and as is apparent for those skilled in the art, symbol  indicates that it is bound to the opposite side of the sheet (namely α-configuration), symbol  indicates that it is bound to the front side of the sheet (namely β-configuration), symbol  indicates that it is a α-configuration, β-configuration or a optional mixture thereof, and symbol  indicates that it is a optional mixture of α-configuration and β-configuration.

[Salt]

The compound represented by the formula (I) is converted to a salt by known methods.

A pharmaceutically acceptable salt is preferred as the salt. Water soluble salt is preferable.

Examples of salts include alkali metal salts, alkali earth metal salts, ammonium salts, amine salts or acid addition salts, or the like.

Examples of alkali metal salts include potassium and sodium salts and the like.

Examples of alkali earth metal salts include calcium and magnesium salts and the like.

Examples of ammonium salts include tetramethylammonium and the like.

Examples of amine salts include triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine and the like.

Examples of acid addition salts include inorganic acid salts such as hydrochloride salts, hydrobromide salts, hydroiodide salts, sulfate salts, phosphate salts and nitrate salts, or organic acid salts such as acetate salts, lactate salts, tartrate salts, benzoate salts, citrate salts, methanesulfonate salts, ethanesulfonate salts, trifluoroacetate salts, benzenesulfonate salts, toluenesulfonate salts, isethionate salts, glucuronate salts and gluconate salts.

The compound of the present invention can also be made into an N-oxide by any method. The N-oxide is the compound which the nitrogen atom of the compound represented by the formula (I) was oxidized to.

The compound represented by the formula (I) and the salt thereof can also be converted into solvates.

A solvate is preferably non-toxic and water-soluble. Examples of suitable solvates include solvates using water or an alcohol solvent such as ethanol or the like.

[Prodrug]

A prodrug of the compound represented by the formula (I) is a compound that is converted by enzymes, gastric acids or the like in the body into the compound represented by the formula (I). Examples of prodrugs of the compound represented by the formula (I) include compounds in which a carboxyl group in the formula (I) is esterified or amidated (such as those in which a carboxyl in the compound represented by the formula (I) is ethyl-esterified, isopropyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified or methylamidated); and compounds in which a carboxyl group in the formula (I) has been replaced with a hydroxymethyl group and the like.

These compounds can be manufactured by known methods. A prodrug of the compound represented by the formula (I) may be a hydrate or non-hydrate.

Further, the compound represented by the formula (I) may be labeled with an isotope (e.g., $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, etc.).

[Method for Manufacturing the Compound of the Present Invention]

The compound of the present invention represented by the formula (I) can be manufactured by known methods, such as by the methods shown below or similar methods thereof, or by the methods described in the examples. A raw material compound may be used in the form of a salt. When a raw material compound has a reactive functional group (carboxyl group or the like), this reactive functional group can be protected as necessary with a suitable protective group, which can then be removed after completion of the reaction. When a raw material compound is used in the form of a salt, one described as a pharmaceutically acceptable salt of the formula (I) is used.

The compound represented by the formula (I) can be manufactured by subjecting the compound represented by the formula (II):

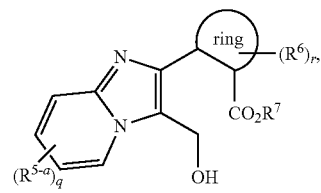

wherein all symbols have the same meaning as in [1] above, and the compound represented by the formula (III):

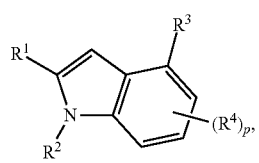

wherein all symbols have the same meaning as in [1] above, to a carbon-carbon bond-forming reaction.

A carbon-carbon bond-forming reaction between the compound represented by the formula (II) and the compound represented by the formula (III) can be accomplished, for example, by reacting them at temperature from room temperature to 250° C. in the presence of an acid (organic acid such as acetic acid, trifluoracetic acid, methanesulfonic acid, p-toluenesulfonic acid, camphorsulfonic acid or the like, inorganic acid such as hydrochloric acid, sulfuric acid or the like, or a mixture of these (hydrogen bromide/acetic acid or the like)), either in a solvent (an organic solvent such as dioxane, dimethylformamide, acetic acid or the like, or water, or a mixed solvent of these (acetic acid/water or the like)) or without a solvent.

As the carboxyl-protecting group, there are exemplified methyl group, ethyl group, allyl group, tert-butyl group, trichloroethyl group, benzyl (Bn) group, phenacyl group, p-methoxybenzyl group, trityl group, 2-chlorotrityl group, or a solid-phase carrier are coupled by those structures, and so forth.

In addition to the above protecting groups for carboxyl group, there is no particular limitation so long as it can be easily and selectively removed. For example, protecting groups described in T. W. Greene, Protective Groups in Organic Synthesis, Wiley, New York, 1999 can be used.

The deprotection method for the protecting group of carboxy group is well known. Examples of such deprotection are
(1) alkali hydrolysis,
(2) deprotection under acidic conditions,
(3) deprotection by hydrogenolysis,
(4) deprotection of silyl groups,
(5) deprotection using a metal,
(6) deprotection using a metal complex.

Details of these deprotection methods are hereinafter illustrated.

(1) The deprotection by alkali hydrolysis is carried out at about 0° C. to about 150° C., using an alkali hydroxide (e.g., sodium hydroxide, potassium hydroxide, lithium hydroxide, etc.), an alkali earth metal hydroxide (e.g., barium hydroxide, calcium hydroxide, etc.) or a carbonate (e.g., sodium carbonate, potassium carbonate, etc.) or an aqueous solution thereof or a mixture thereof, in an organic solvent (e.g., methanol, tetrahydrofuran, 1,4-dioxane, etc.).

(2) The deprotection under acidic conditions is carried out at about 0° C. to about 100° C. with an organic acid (e.g., acetic acid, trifluoroacetic acid, methanesulfonic acid, p-toluenesulfonic acid, etc.) or an inorganic acid (e.g., hydrochloric acid, sulfuric acid, etc.) or a mixture thereof (e.g., hydrogen bromide/acetic acid) in an organic solvent (e.g., dichloromethane, chloroform, dioxane, ethyl acetate, anisole, etc.) in the presence or absence of 2,2,2-trifluoroethanol.

(3) The deprotection by hydrogenolysis is carried out at about 0° C. to about 200° C. in a solvent [ethers (e.g., tetrahydrofuran, dioxane, dimethoxyethane, diethyl ether, etc.), alcohols (e.g., methanol, ethanol, etc.), benzenes (e.g., benzene, toluene, etc.), ketones (e.g., acetone, methyl ethyl ketone, etc.), nitriles (e.g., acetonitrile, etc.), amides (e.g., N,N-dimethylformamide, etc.), water, ethyl acetate, acetic acid or a mixture of two or more solvents thereof] in the presence of a catalyst (e.g., palladium-carbon, palladium black, palladium hydroxide, platinum oxide, Raney-Ni, etc.) under a normal pressure or an increased pressure in a hydrogen stream or in the presence of ammonium formate.

(4) The deprotection of the silyl group is carried out in a water-miscible organic solvent (e.g., tetrahydrofuran, acetonitrile, etc.) using tetrabutylammonium fluoride at about 0° C. to about 40° C.

(5) The deprotection using a metal is carried out in an acidic solvent (e.g., acetic acid, a buffer of pH 4.2 to 7.2, or a mixture of a solvent thereof and an organic solvent such as tetrahydrofuran) in the presence of a zinc dust at about 0° C. to about 40° C. while applying ultrasonic waves, if required.

(6) The deprotection using a metal complex is carried out at about 0° C. to about 40° C. in an organic solvent (e.g., dichloromethane, dimethylformamide, tetrahydrofuran, ethyl acetate, acetonitrile, dioxane, ethanol, etc.), water or a mixture thereof in the presence of a trapping reagent (e.g., tributyltin hydride, triethylsilane, dimedone, morpholine, diethylamine, pyrrolidine, etc.), an organic acid (e.g., acetic acid, formic acid, 2-ethylhexanoic acid, etc.) and/or an organic acid salt (e.g., sodium 2-ethylhexanoate, potassium 2-ethylhexanoate, etc.) and in the presence or absence of a phosphine reagent (e.g., triphenylphosphine, etc.), using a metal complex [e.g., tetrakistriphenylphosphine palladium(0), bis(triphenylphosphine)palladium(II) dichloride, palladium(II) acetate, tris(triphenylphosphine)rhodium(I) chloride].

For example, as well as above, the deprotection reaction can be done by means of a method described by T. W. Greene, Protective Groups in Organic Synthesis, Wiley, New York, 1999.

The compound represented by the formula (II) can be manufactured by the method shown by Reaction Process Formula 1. In Reaction Process Formula 1, X represents a halogen atom or sulfonate (for example, mesylate, tosylate, trifluoromethanesulfonate or the like), and the other symbols have the same meanings as in [1] above.

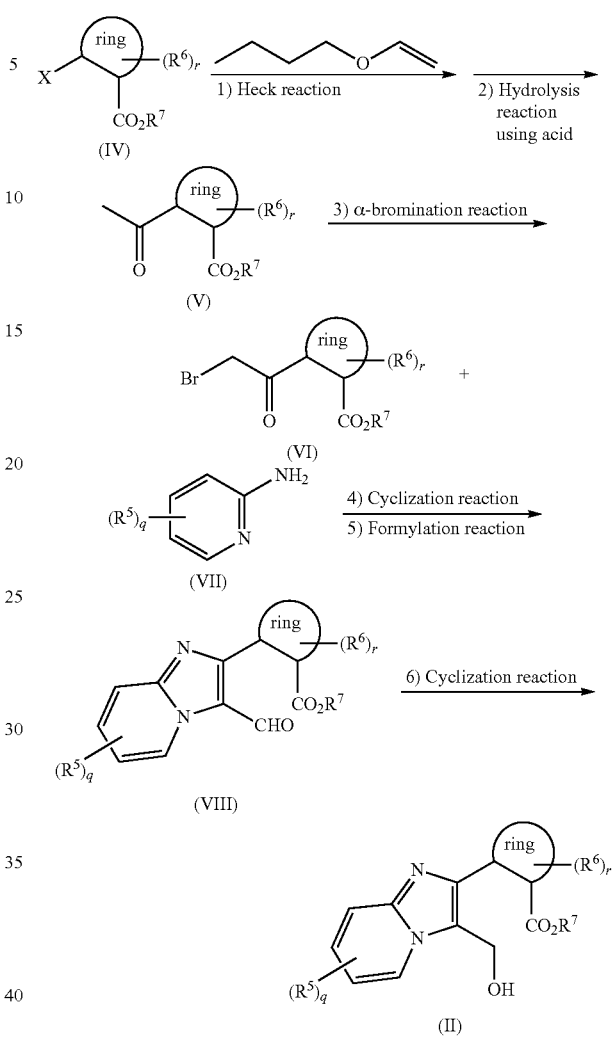

Reaction Process Formula 1

The Heck reaction, hydrolysis reaction using acid, α-bromination reaction, cyclization reaction, formylation reaction and cyclization reaction in Reaction Process Formula 1 can be accomplished under the conditions described in the examples of the description, or under known conditions.

In Reaction Process Formula 1, the compounds represented by the formulae (IV) and (VII) to use as a starting material are well known, or can be produced easily by using a known method, for example, the method described in "Comprehensive Organic Transformations: A Guide to Functional Group Preparations 2nd Edition (Richard C. Larock, John Wiley & Sons Inc, 1999)".

The compound represented by the formula (III) is well known, or can be produced easily by using a known method, for example, the method described in "Comprehensive Organic Transformations: A Guide to Functional Group Preparations 2nd Edition (Richard C. Larock, John Wiley & Sons Inc, 1999)".

Besides compounds shown as above of the compound of the present invention described by the formula (I), they can be produced by the examples described in the description, the known method, for example, the method described in Comprehensive Organic Transformations: A Guide to Functional Group Preparations, 2nd Edition (Richard C. Larock, John Wiley & Sons Inc, 1999), or a combination method thereof.

The heating reaction in each reaction of the present invention may be performed using a water bath, an oil bath, a sand bath or a microwave, though it is apparent to those skilled in the art.

In each reaction of the present invention, a reagent appropriately carried on a solid carrier of polymers (e.g., polystyrene, polyacrylamide, polypropylene, polyethylene glycol, etc.) may be used.

In each reaction in the description, reaction products may be purified by general purification techniques, for example, by distillation under atmospheric or reduced pressure, by high performance liquid chromatography, by thin layer chromatography, by ion exchange resin, by scavenger resin, or by column chromatography using silica gel or magnesium silicate; or by washing or by recrystallization. Purification may be carried out after each reaction or after a series of reactions.

[Toxicity]

The compound of the present reaction has sufficiently low toxicity, and has been confirmed to be safe enough for use as a medicinal drug.

[Application to Medicinal Drug]

Because the compound of the present invention exhibits chymase inhibitory activity, it is useful as an agent for preventing and/or treating chymase-mediated diseases, such as skin diseases, circulatory diseases, digestive system diseases, respiratory diseases, kidney diseases, ocular diseases, liver diseases, organ adhesion due to surgery or the like.

More particularly, examples of skin diseases include atopic dermatitis, allergic contact dermatitis, scleroderma, systemic scleroderma, keloids, hypertrophic scar, hives, psoriasis and the like. Examples of circulatory diseases include hypertension, pulmonary hypertension, cardiomyopathy, myocarditis, restenosis following percutaneous transluminal coronary angioplasty and/or thrombolysis treatment, stenosis following implantation of artificial blood vessels and/or transplanted blood vessels, heart failure (such as congestive heart failure, acute heart failure or chronic heart failure), arrhythmia, angina (such as unstable angina), acute coronary syndrome, myocardial infarction (such as acute myocardial infarction), coronary artery disease, arteriosclerosis (such as arteriosclerosis obliterans), peripheral circulatory disorders, cerebrovascular diseases, angiitis, aneurism, angiopathy involving arteriovenous fistula during blood dialysis and the like. Examples of digestive system diseases include peptic ulcers (such as stomach ulcers, duodenal ulcers, small-intestinal ulcers and digestive ulcers caused by non-steroidal antiphlogistic analgesics), inflammatory bowel disease (such as ulcerative colitis and Crohn's disease) and the like. Examples of respiratory diseases include bronchial asthma, chronic obstructive pulmonary disease, chronic bronchitis, pulmonary emphysema, idiopathic interstitial pneumonia, pulmonary fibrosis (such as idiopathic pulmonary fibrosis) and the like. Examples of kidney diseases include diabetic nephropathy and non-diabetic nephropathy, IgA nephropathy, glomerular nephritis and the like. Examples of ocular diseases include myopia, dry eye, corneal epithelial disorder, marginal blepharitis, allergic conjunctivitis and the like. Examples of liver diseases include cirrhosis of the liver, hepatic fibrosis, non-alcoholic fatty liver disease (such as non-alcoholic steatohepatitis), alcoholic steatohepatitis and the like. Examples of organ adhesion due to surgery include abdominal organ adhesion after abdominal surgery, adhesion after glaucoma surgery (such as trabeculotomy), adhesion after craniotomy procedures (such as external decompression), adhesion after heart surgery and the like.

The compound of the present invention has unprecedented chymase inhibitory activity, and its side-effect risk of hepatotoxicity is very low, and its compound has excellent metabolic stability. Therefore, the compound of the present invention becomes a useful medicinal drug for clinical use.

In general, the medicinal drugs are more preferable if the effect on a disease of medicinal drugs is greater, but a side-effect must not become serious with it. A drug is safer, if the gap (ratio) between the dosage exhibiting an effect on the disease (effectiveness) and the dosage at which side-effect appears is greater, and such medical drugs are expected.

Also, most chymase-mediated diseases are chronic diseases, and it is wished that the drug that a burden on a liver was reduced more is found, because the drug needs to be administered for a long term in order to treat, in particular, atopic dermatitis, ulcerative colitis, peptic ulcers, non-alcoholic fatty liver diseases, and pulmonary fibrosis or the like. That is, the compound that risk of hepatotoxicity is low is expected. Risk of hepatotoxicity can be evaluated by means of mitochondrial function, reactive metabolites, and human liver cancer cell lines (abbreviated as HepG2) or the like.

Of the commonly known medicinal drugs, in medicinal drugs that the hepatotoxicity is a problem, a ratio of principal activity ($IC_{50}$) and, for example, HepG2 cell toxicity ($IC_{50}$) ($IC_{50}$ (HepG2 cell toxicity)/$IC_{50}$ (principal activity of drug)) is 0.06 to 2000, so compounds for which this ratio is about 2000 are expected as compounds with low risk of hepatotoxicity.

That is, in the present invention, the ratio of HepG2 cell toxicity ($IC_{50}$) to chymase inhibitory activity ($IC_{50}$) ($IC_{50}$ (HepG2 cell toxicity)/$IC_{50}$ (chymase inhibitory activity)) is preferably 2000× or more, or more preferably 3500× or more in order to achieve a medicinal drug that is clinically useful against chymase-mediated diseases.

In chymase-mediated diseases, in particular, in atopic dermatitis, ulcerative colitis, peptic ulcers, non-alcoholic fatty liver disease, pulmonary fibrosis and the like, the aim is to completely cure the disease or suppress the progress of the disease. Therefore, chymase inhibitory activity should be evaluated at the level of $IC_{90}$ as a benchmark of maximum effect in order to ensure the maximum effect of curing the disease or suppressing the progress of the disease.

Thus, in the compound of the present invention, $IC_{90}$ value was calculated in addition to $IC_{50}$ value of normal enzyme inhibitory activity.

In addition, HepG2 cell toxicity should be evaluated at the level of $IC_{10}$ so that the safety risk of the liver can be assessed with more sensitivity in order to discover drugs that reduce the burden on the liver.

Thus, the $IC_{10}$ value was calculated in addition to the normal $IC_{50}$ value for cell toxicity of the compound of the present invention.

The compound of the present invention is also useful as an agent for preventing and/or treating hyperuricemia.

The compound of the present invention can also be administered as a companion drug in combination with another drug in order to:

1) supplement and/or enhance the preventive and/or therapeutic effect of the compound;

2) improve the pharmacokinetics and absorption or reduce the dosage of the compound; and/or 3) reduce the side-effects of the compound.

When the compound of the present invention is used as a companion drug with another drug, the two can be compounded in one preparation and administered in the form of a combination drug, or can be administered as separate preparations. When they are administered as separate preparations, they may be administered simultaneously or with a time lag between administrations. If there is a time lag, the compound of the present invention may be administered first and the other drug administered later, or the other drug may be administered first and the compound of the present invention administered later. The administration methods may be the same or different.

The disease on which such a companion drug has a preventive and/or therapeutic effect is not particularly limited, and may be any disease for which the preventive and/or therapeutic effect of the compound of the present invention is supplemented and/or enhanced.

The other medicaments for the purpose of supplementing and/or enhancing of preventive and/or therapeutic effect of the compound of the present invention on atopic dermatitis include, for example, nonsteroidal anti-inflammatory drugs, steroid drugs, immunosuppressive drugs, prostaglandins, anti-allergic drugs, mediator release inhibitors, leukotriene receptor antagonists, antihistamines, opioid agonists (such as agonist), phosphodiesterase inhibitors, forskolin formulations, nitric oxide synthase inhibitors, cannabinoid-type 2 receptor agonists, decoy formulations such as NF-κB, and chymase inhibitors, etc.

Examples of nonsteroidal anti-inflammatory drugs include sazapirin, sodium salicylate, aspirin, aspirin preparation such as aspirin dialuminate formulations, diflunisal, indomethacin, suprofen, ufenamate, dimethylisopropylazulene, bufexamac, felbinac, diclofenac, tolmetin sodium, clinoril, fenbufen, nabumetone, puroglumetacine, indometacin farnesil, acemetacin, proglumetacin maleate, amfenac sodium, mofezolac, etodolac, ibuprofen, ibuprofenpiconol, naproxen, flurbiprofen, flurbiprofen axetil, ketoprofen, fenoprofen calcium, tiaprofene, oxaprozin, pranoprofen, loxoprofen sodium, aluminoprophen, zaltoprofen, mefenamic acid, aluminum mefenamete, tolfenamic acid, furokutafenin, ketofenirubutazon, oxyphenbutazone, piroxicam, tenoxicam, anpirokishikamu, napageln, epirizole, tiaramide hydrochloride, tinoridine hydrochloride, emorfazone, sulpyrine, migrenin, saridon, sedes G, amipylo-N, sorbon, pyrine drug for common cold, acetaminophen, phenacetin, dimetotiazine mesilate, meloxicam, celecoxib, rofecoxib, valdecoxib, simetride combination drug, and non-pyrine drug for common cold, etc.

Examples of steroid drugs as external medicine include clobetasol propionate, diflorazone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone dipropionate, triamcinolone acetonide, flumetasone pivalate, alclometasone dipropionate, clobetasone butyrate, prednisolone, beclometasone dipropionate, and fludroxycortide.

Examples of steroid drugs as internal drug or injection drug include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, sodium methylprednisolone succinate, triamcinolone, triamcinolone diacetate, triamcinolone acetonide, dexamethasone, dexamethasone acetate, dexamethasone sodium phosphate, dexamethasone palmitate, paramethasone acetate, and betamethasone, etc.

Examples of steroid drugs as inhalation drug include beclomethasone dipropionate, fluticasone propionate, budesonide, flunisolide, triamcinolone, ST-126P, ciclesonide, dexamethasone palmitate, mometasone furancarbonate, prasterone sulfonate, deflazacort, methylprednisolone suleptanate, and sodium methylprednisolone succinate, etc.

Examples of immunosuppressive drugs include protopic, tacrolimus (FK-506), methotrexate, cyclosporin, neoral, ascomycin, leflunomide, bucillamine, and salazosulfapyridine, etc.

Examples of prostaglandins (hereinafter, abbreviated as PG) include agonist and antagonist, etc. of PGE receptors (EP1, EP2, EP3 and EP4), PGD receptors (DP, CRTH2), PGF receptors (FP), PGI receptors (IP), TX receptors (TP), etc.

Examples of antiallergic drugs include amlexanox, azelastine hydrochloride, israpafant, ibudilast, imitrodast sodium, ebastine, epinastine hydrochloride, emedastine difumarate, oxatomide, ozagrel hydrochloride, olopatadine hydrochloride, cromoglicate, sodium cromoglicate, ketotifen fumarate, seratrodast, cetirizine hydrochloride, suplatast tosilate, tazanolast, terfenadine, domitroban calcium hydrate, tranilast, nedocromil, fexofenadine, fexofenadine hydrochloride, pemirolast potassium, mequitazine, ramatroban, repirinast, and loratadine, etc.

Examples of mediator release inhibitors include tranilast, sodium cromoglicate, amlexanox, repirinast, ibudilast, tazanolast, and pemirolast potassium, etc.

Examples of leukotriene receptor antagonists include pranlukast hydrate, montelukast, zafirlukast, MCC-847, KCA-757, CS-615, YM-158, L-740515, CP-195494, LM-1484, RS-635, A-93178, S-36496, BIIL-284, and ONO-4057, etc.

Examples of antihistamines include ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, and acrivastine, etc.

Examples of opioid agonists include codeine, fentanyl, hydromorphone, levorphanol, meperidine, methadone, morphine, oxycodone, oxymorphone, propoxyphene, etc. Examples of κ-opioid agonists include TRK-820, nalfurafine, and U50488H, etc.

Examples of phosphodiesterase inhibitors as phosphodiesterase 4 inhibitor include rolipram, cilomilast, Bay19-8004, NIK-616, roflumilast (BY-217), cipamfylline (BRL-61063), atizoram (CP-80633), SCH-351591, YM-976, V-11294A, PD-168787, D-4396, and IC-485, etc. Examples of phosphodiesterase inhibitors as phosphodiesterase 5 inhibitor include sildenafil, etc.

Examples of forskolin formulations include colforsin daropate hydrochloride and forslean, etc.

Examples of nitric oxide synthase inhibitors include $N^G$-nitro-L-arginine methyl ester (L-NAME), $N^G$-monomethyl-L-arginine (L-NMMA), and $N^G$-nitro-L-arginine (L-NNA), etc.

Examples of cannabinoid-2 receptor stimulants include S-777469, S-444823, the compounds described in WO 02/010135, and the compounds described in WO 03/064389, etc.

Examples of decoy formulations include NF-κB, etc.

Examples of chymase inhibitors include TPC-806, and SUN13834, etc.

The other medicaments for the purpose of supplementing and/or enhancing of preventive and/or therapeutic effect of the compound of the present invention on ulcerative colitis include, for example, steroid drugs, immunosuppressive drugs, aminosalicylic acid formulations, chymase inhibitors, and the other drugs.

Examples of steroid drugs include steroid drugs described as the other medicaments for the purpose of supplementing and/or enhancing of preventive and/or therapeutic effect of the compound of the present invention on atopic dermatitis.

Examples of immunosuppressive drugs include immunosuppressive drugs described as the other medicaments for the purpose of supplementing and/or enhancing of preventive and/or therapeutic effect of the compound of the present invention on atopic dermatitis.

Examples of aminosalicylic acid formulations include pentasa, salazosulfapyridine, and mesalazine, etc.

Examples of chymase inhibitors include chymase inhibitors described as the other medicaments for the purpose of supplementing and/or enhancing of preventive and/or therapeutic effect of the compound of the present invention on atopic dermatitis.

Examples of the other drugs include thalidomide, remicade, infliximab, and the other TNF-α antagonist, and Interleukin-6 (hereinafter, abbreviated as IL-6) antagonist such as Anti-IL-6 receptor antibody, etc.

The other medicaments for the purpose of supplementing and/or enhancing of preventive and/or therapeutic effect of the compound of the present invention on heart failure include, for example, diuretics, angiotensin converting enzyme inhibitors, angiotensin II receptor antagonists, antiarrhythmic drugs, digitalis preparations, chymase inhibitors, renin inhibitors, calcium antagonists, beta blockers, nitric acids, anti-aldosterone drugs, cardiotonic drugs, antiplatelet drugs, and anticoagulant drugs, etc.

Examples of diuretics include hydrochlorothiazide, trichlormethiazide, benzylhydrochlorothiazide, indapamide, chlorthalidone, mefruside, meticrane, tripamide, furosemide, torasemide, ethacrynic acid, bumetanide, piretanide, azosemide, and triamterene, etc.

Examples of angiotensin converting enzyme inhibitors include captopril, enalapril, alacepril, delapril, cilazapril, benazepril, lisinopril, and perindopril, etc.

Examples of angiotensin II receptor antagonists include candesartan, losartan, olmesartan, valsartan, telmisartan, irbesartan, candesartan cilexetil, losartan potassium, olmesartan medoxomil, losartan potassium, losartan potassium hydrochlorothiazide, blopress plus, diovan HCT, valsartan HCTZ, CS-866CMB, VAA489, CS-8663, CS-866AZ, candesartan amlodipine, telmisartan HCTZ, TAK-491, TAK-536, TAK-591, and KT3-671, etc.

Examples of antiarrhythmic drugs include amiodarone, etc.

Examples of digitalis preparations include digoxin, etc.

Examples of chymase inhibitors include chymase inhibitors described as the other medicaments for the purpose of supplementing and/or enhancing of preventive and/or therapeutic effect of the compound of the present invention on atopic dermatitis.

Examples of renin inhibitors include aliskiren, and aliskiren fumarate, etc.

Examples of calcium antagonists include nifedipine, nicardipine, nicardipine hydrochloride, nilvadipine, nisoldipine, nitrendipine, manidipine, manidipine hydrochloride, benidipine, barnidipine hydrochloride, barnidipine, amlodipine, amlodipine besilate, efonidipine, efonidipine hydrochloride; felodipine, cilnidipine, aranidipine, azelnidipine, diltiazem, diltiazem hydrochloride, verapamil, verapamil hydrochloride, bepridil, and bepridil hydrochloride, etc.

Examples of beta blockers include carvedilol, bisoprolol, metoprolol, propranolol, nadolol, nipradilol, tilisolol, pindolol, penbutolol, carteolol, bopindolol, atenolol, acebutolol, and celiprolol, etc.

Examples of nitric acids include nitroglycerin, amyl nitrite, and isosorbide dinitrate, etc.

Examples of anti-aldosterone drugs include spironolactone, and eplerenone, etc.

Examples of cardiotonic drugs include pimobendan, denopamine, docarpamine, and vesnarinone, etc.

Examples of antiplatelet drugs include cyclooxygenase inhibitors, thromboxane synthetase inhibitors, thromboxane receptor antagonists, adenosine diphosphate receptor antagonists, serotonin receptor antagonists, phosphodiesterase inhibitor, prostaglandins, and glycoprotein IIb/IIIa receptor antagonists, etc. Specifically, for example, aspirin, ticlopidine hydrochloride, clopidogrel sulfate, prasugrel, CS-747, ticagrelor, AZD6140, elinogrel, PRT128, YM337, YM028, dipyridamole, cilostazol, beraprost sodium, sarpogrelate hydrochloride, ozagrel sodium, abciximab, tirofiban, and eptifibatide are included.

Examples of anticoagulant drugs include heparin such as heparin sodium, dalteparin sodium, heparin calcium, parnaparin sodium, and revaparin sodium, heparinoid such as low molecule heparin, for example, danaparoid sodium, enoxaparin, nadroparin, bemiparin, reviparin, and tinzaparin, thrombin inhibitor such as argatroban, ximelagatran, melagatran, dabigatran, bivalirudin (hirulog), lepirudin, hirudin, desirudin, SSR-182289A, SR-123781A, S-18326, AZD-0837, LB-30870, L-375378, MCC-977, and AT-1326, activated protein C preparation such as CTC-111, activated drotrecogin alfa, antithrombin III preparation, gabexate mesilate, nafamostat mesilate, tissue factor pathway inhibitor such as rNAPc2, Sunol-CH36, Ro-678698, and PHA-798, the order anticoagulant drug, for example, inhibitors activated blood coagulation factor X such as apixaban, rivaroxaban, edoxaban, BMS-561389, BAY-59-7939, YM150, LY-517717, KFA-1982, KFA-1829, DU-176b, fondaparinux, idraparinux, inhibitors activated blood coagulation factor IX such as TTP-889, IXa aptamer (RB006), and 224AE3, thrombomodulin preparation such as ART-123, carboxypeptidase U inhibitor (TAFI) such as sodium citrate and AZD-9684, vitamin K antagonist such as warfarin, warfarin, warfarin potassium.

The other medicaments for the purpose of supplementing and/or enhancing of preventive and/or therapeutic effect of the compound of the present invention on pulmonary fibrosis include, for example, steroid drugs, immunosuppressive drugs, and antifibrotic drugs, etc.

Examples of steroid drugs include steroid drugs described as the other medicaments for the purpose of supplementing and/or enhancing of preventive and/or therapeutic effect of the compound of the present invention on atopic dermatitis.

Examples of immunosuppressive drugs include immunosuppressive drugs described as the other medicaments for the purpose of supplementing and/or enhancing of preventive and/or therapeutic effect of the compound of the present invention on atopic dermatitis.

Examples of antifibrotic drugs include pirfenidone, pirespa, and chymase inhibitors such as TPC-806 and SUN13834, etc.

The other medicaments for the purpose of supplementing and/or enhancing of preventive and/or therapeutic effect of the compound of the present invention on aneurysm include, for example, hypoglycemic drugs, anti-hypertensive drugs, lipid improving drugs, and anti-obesity drugs, etc.

Examples of hypoglycemic drugs include repaglinide, miglitol, exenatide, nateglinide, mitiglinide calcium hydrate, pioglitazone hydrochloride, rosiglitazone maleate, balaglitazone, R-483, netoglitazone, naveglitazar, T-131, SUN-E7001, CLX-0921, metformin, buformin, miglitol, voglibose, acarbose, insulinotropin, liraglutide, CJC-1131, GLP-1, R-1583, LY-307161, rGLP-1 (Betatropin), sitagliptin, vildagliptin, alogliptin, LAF-237, P-32/98, P-93/01, TS-021, 815541, 825964, 823093, TA-6666, and MK-0431, etc.

Examples of anti-hypertensive drugs include captopril, enalapril, alacepril, delapril, cilazapril, benazepril, lisinopril, perindopril, candesartan, losartan, olmesartan, valsartan, telmisartan, irbesartan, candesartan cilexetil, losartan potassium, olmesartan medoxomil, losartan potassium, losartan potassium hydrochlorothiazide, blopress plus, diovan HCT, valsartan HCTZ, CS-866CMB, VAA489, CS-8663, CS-866AZ, candesartan amlodipine, telmisartan HCTZ, TAK-491, TAK-536, TAK-591, KT3-671, doxazosin, urapidil, terazosin, and prazosin, etc.

Examples of anti-obesity drugs include rimonabant, mazindol, orlistat, and sibutramine, etc.

Examples of lipid improving drugs include atorvastatin, simvastatin, pitavastatin, pravastatin, fluvastatin, rosuvastatin, lovastatin, ezetimibe, bezafibrate, clinofibrate, aluminium clofibrate, fenofibrate, clofibrate, probucol, and eicosapentaenoic acid, etc.

The other medicaments for the purpose of supplementing and/or enhancing of preventive and/or therapeutic effect of the compound of the present invention on non-alcoholic steatohepatitis (NASH) include, for example, hypoglycemic drugs, anti-hypertensive drugs, lipid improving drugs, anti-obesity drugs, hepatoprotective agents, antioxidant drugs, and antifibrotic drugs, etc.

Examples of hypoglycemic drugs include hypoglycemic drugs described as the other medicaments for the purpose of supplementing and/or enhancing of preventive and/or therapeutic effect of the compound of the present invention on aneurysm.

Examples of anti-hypertensive drugs include anti-hypertensive drugs described as the other medicaments for the purpose of supplementing and/or enhancing of preventive and/or therapeutic effect of the compound of the present invention on aneurysm.

Examples of anti-obesity drugs include anti-obesity drugs described as the other medicaments for the purpose of supplementing and/or enhancing of preventive and/or therapeutic effect of the compound of the present invention on aneurysm.

Examples of lipid improving drugs include lipid improving drugs described as the other medicaments for the purpose of supplementing and/or enhancing of preventive and/or therapeutic effect of the compound of the present invention on aneurysm.

Examples of hepatoprotective agents include stronger neominophagen C, ursodeoxycholic acid, and sho-saiko-to, etc.

Examples of antioxidant drugs include Vitamin C, Vitamin E, N-acetylcysteine, betaine, and s-adenosylmethionine, etc.

Examples of antifibrotic drugs include antifibrotic drugs described as the other medicaments for the purpose of supplementing and/or enhancing of preventive and/or therapeutic effect of the compound of the present invention on pulmonary fibrosis.

The other medicaments for the purpose of supplementing and/or enhancing of preventive and/or therapeutic effect of the compound of the present invention on non-steroidal anti-inflammatory drugs-induced peptic ulcer include, for example, prostaglandins, H2-receptor antagonists, and proton pump inhibitors, etc.

Examples of prostaglandins include misoprostol, cytotec, and cobiprostone, etc.

Examples of H2-receptor antagonists include, cimetidine, tagamet, ranitidine hydrochloride, zantac, famotidine, gastar, nizatidine, acinon, roxatidine acetate hydrochloride, altat, lafutidine, protecadin, and stogar, etc.

Examples of proton pump inhibitors include omepral, omeprazon, takepron, pariet, lansoprazole, omeprazole, and rabeprazole, etc.

The other medicaments for the purpose of supplementing and/or enhancing of preventive and/or therapeutic effect of the compound of the present invention on allergic conjunctivitis include, for example, anti-allergic drugs and steroid drugs, etc.

Examples of anti-allergic drugs include anti-allergic drugs described as the other medicaments for the purpose of supplementing and/or enhancing of preventive and/or therapeutic effect of the compound of the present invention on atopic dermatitis.

Examples of steroid drugs include steroid drugs described as the other medicaments for the purpose of supplementing and/or enhancing of preventive and/or therapeutic effect of the compound of the present invention on atopic dermatitis.

The mass ratio of the compound of the present invention and the other medicaments is not specifically limited.

Any combination of two or more kinds of other medicaments may be administered.

Further, the other medicaments for supplementing and/or enhancing the preventive and/or therapeutic effect of the compound of the present invention include not only those found so far but also those which will be found on the basis of the above-mentioned mechanism.

For the purpose described above, the compound of the present invention, or a combination of the compound of the present invention and other medicaments may be normally administered systemically or locally, usually by oral or parenteral administration.

The dosages to be administered are determined depending upon, for example, ages, body weights, symptoms, the desired therapeutic effects, the route of administration, and the duration of the treatment. For the human adult, the dosage per person is generally from 1 mg to 1,000 mg, by oral administration, from one to several times per day, and from 0.1 mg to 100 mg, by parenteral administration (preferably, nasal drops, eye drops, or ointments), from one to several times per day, or continuous administration for 1 to 24 hours per day from vein.

As described above, of course, the dosages to be used depend upon various conditions. Therefore, there are cases in which dosages lower than or greater than the ranges specified above may be used.

The compound of the present invention, or the combination agent of the compound of the present invention and the other medicaments is administrated, those are used as solid preparations for internal use and liquid preparations for internal use for oral administration as well as preparations for injections, external preparations, suppositories, eye drops, inhalations and the like for parenteral administration.

The solid preparations for oral administration include tablets, pills, capsules, dispersible powders, granules, and so forth. The capsules include hard capsules and soft capsules. Further, the tablets include sublingual tablets, oral patches, orally disintegrating tablets, etc.

Such a solid preparation for internal use is prepared by a formulation method commonly employed by using one or more active substances either as it is or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer, and a solubilizer (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

Liquid forms for oral administration include pharmaceutically acceptable solutions, suspensions and emulsions, syrups, and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

In the parenteral administration, formulation of external use include, for example, ointment, gel, cream, poultice, patch, liniment, aerosolized agent, inhalation, spray, aerosols, eye-drop, and nasal spray, etc. They includes one or more of the active compound(s) and be prepared by known method or usual method.

Aerosolized agent, inhalation and spray may comprise in addition to a diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solubilizers (such as glutamic acid, aspartic acid or POLYSORBATE80 (registered trade mark)), suspending agents, emulsifying agents, soothing agent, buffering agents, preservative. They may be sterilized at a final step, or may be prepared by an aseptic manipulation. They may also be manufactured in the form of sterile solid forms, for example, freeze-dried products, which may be dissolved in sterile water or some other sterile diluent(s) for injection immediately before use.

The other compositions for parenteral administration include suppositories for intrarectal administration and pessaries for vaginal administration which comprise one or more of the active substance(s) and may be prepared by methods known per se.

In addition, documents described by the description of the present invention are quoted by reference.

EXAMPLES

The present invention is explained below in detail based on Examples, but the present invention is not limited thereto.

Solvents given in parentheses concerning chromatographic separation and TLC each indicate the eluting solvent or the developing solvent employed, and the ratio is expressed in ratio by volume.

The solvents in parenthesis in NMR show the solvents used for measurement.

The nomenclature used in the description of the present invention is based on ACD/Name (registered trademark) (version 6.00, manufactured by Advanced Chemistry Development Inc.).

Example 1

Methyl 2-acetyl-1-naphthoate

Under an atmosphere of argon, butyl vinyl ether (6.4 mL), palladium(II) acetate (0.17 g), triphenylphosphine (0.39 g), and triethylamine (1.7 mL) were added to a solution of methyl 2-trifluoromethanemethanesulfonyloxy-1-naphthoate (3.34 g) in acetonitrile (20 mL). The reaction mixture was stirred under reflux overnight. The reaction mixture was filtered with Celite (trade name), and the filtrate was concentrated under reduced pressure. The obtained residue was dissolved with tetrahydrofuran (200 mL), and the reaction mixture was cooled on ice bath. 1 M hydrochloric acid (200 mL) was added to the reaction mixture, and the reaction mixture was stirred for ten minutes. Water was added to the reaction mixture, and the reaction mixture was extracted with ethyl acetate. The obtained organic layer was washed with water and a saturated salt solution. The obtained extract was concentrated after drying with anhydrous sodium sulfate. The obtained residue was purified by column chromatography on silica gel (hexane:ethyl acetate=75:25) to give the title compound (2.15 g) having the following physical data.

TLC: Rf 0.36 (hexane:ethyl acetate=3:1);

$^1$H-NMR (CDCl$_3$): δ 2.70 (s, 3H), 4.07 (s, 3H), 7.52-7.68 (m, 2H), 7.85-8.06 (m, 4H).

Example 2

Methyl 2-(bromoacetyl)-1-naphthoate

Diisopropylethylamine (0.10 mL) and phenyltrimethylammoniumtribromide (747 mg) were added to a solution of the compound prepared in Example 1 (454 mg) in 1,2-dimethoxyethane (10 mL), and the reaction mixture was stirred for 3.5 hours at room temperature. The reaction mixture was filtered, and the filtrate was concentrated under reduced pressure. The obtained residue was purified by column chromatography on silica gel (hexane:ethyl acetate=75:25) to give the title compound (325 mg) having the following physical data.

TLC: Rf 0.40 (hexane:ethyl acetate=3:1);

$^1$H-NMR (CDCl$_3$): δ 4.07 (s, 3H), 4.51 (s, 2H), 7.57-7.70 (m, 2H), 7.81 (d, 1H), 7.87-7.95 (m, 1H), 7.97-8.10 (m, 2H).

Example 3

Methyl 2-imidazo[1,2-a]pyridin-2-yl-1-naphthoate 2-aminopyridine (184 mg) was added to a solution of the compound prepared in Example 2 (321 mg) in dimethylformamide (10 mL), and the reaction mixture was stirred for an hour at 80° C. Water was added to the reaction mixture, and the reaction mixture was extracted with ethyl acetate. The obtained organic layer was washed with a saturated salt solution. The obtained extract was concentrated under reduced pressure after drying with anhydrous sodium sulfate. The obtained residue was purified by column chromatography on silica gel (hexane:ethyl acetate=50:50) to give the title compound (145 mg) having the following physical data.

TLC: Rf 0.37 (hexane:ethyl acetate=1:1);
$^1$H-NMR (CDCl$_3$): δ 4.01 (s, 3H), 6.73-6.87 (m, 1H), 7.10-7.23 (m, 1H), 7.44-7.60 (m, 2H), 7.64 (dd, 1H), 7.79-7.91 (m, 3H), 7.91-8.04 (m, 2H), 8.08-8.22 (m, 1H).

Example 4

Methyl 2-(3-formylimidazo[1,2-a]pyridin-2-yl)-1-naphthoate

The compound prepared in Example 3 (172 mg) was added to phosphorous oxychloride (1.7 mL), and the suspended reaction mixture was stirred at room temperature. Dimethylformamide (0.046 mL) was added to the reaction mixture, and the reaction mixture was stirred for 5.5 hours at 70° C. The reaction mixture was cooled on ice bath, and neutralized with an aqueous solution of 2 N sodium hydroxide. The reaction mixture was extracted with ethyl acetate. The obtained organic layer was washed with a saturated salt solution. The obtained extract was concentrated under reduced pressure after drying with anhydrous sodium sulfate. The title compound (196 mg) having the following physical data was obtained.

TLC: Rf 0.37 (hexane:ethyl acetate=1:1);
$^1$H-NMR (CDCl$_3$): δ 3.82 (s, 3H), 7.11-7.22 (m, 1H), 7.52-7.68 (m, 3H), 7.72 (d, 1H), 7.78-7.87 (m, 1H), 7.91-8.00 (m, 1H), 8.01-8.13 (m, 2H), 9.58-9.71 (m, 1H), 9.95 (s, 1H).

Example 5

Methyl 2-[3-(hydroxymethyl)imidazo[1,2-a]pyridin-2-yl]-1-naphthoate

The compound prepared in Example 4 (195 mg) was added to tetrahydrofuran (1.5 mL) and suspended. A solution of sodium borohydride (34 mg) in water (0.4 mL) was added to the reaction mixture on ice bath, and the reaction mixture was stirred for an hour. A saturated aqueous solution of ammonium chloride was added to the reaction mixture, and the reaction mixture was extracted twice with ethyl acetate. The obtained organic layer was joined, and washed with water, a saturated aqueous solution of sodium hydrogen carbonate and a saturated salt solution sequentially. The obtained organic layer concentrated under reduced pressure after drying with anhydrous sodium sulfate. The obtained residue was purified by column chromatography on silica gel (hexane:ethyl acetate=25:75) to give the title compound (186 mg) having the following physical data.

TLC: Rf 0.27 (hexane:ethyl acetate=1:3);
$^1$H-NMR (CDCl$_3$): δ 2.65 (t, 1H), 3.77 (s, 3H), 4.86 (d, 2H), 6.81-6.97 (m, 1H), 7.24-7.33 (m, 1H), 7.51-7.69 (m, 4H), 7.82-7.95 (m, 2H), 7.97 (d, 1H), 8.25-8.38 (m, 1H).

Example 6

Methyl 2-{3-[(4-methyl-1H-indol-3-yl)methyl]imidazo[1,2-a]pyridin-2-yl}-1-naphthoate The compound prepared in Example 5 (47 mg) and 4-methylindole (20 mg) were added to water (0.25 mL) and suspended, and the reaction mixture was stirred at room temperature. Acetic acid (0.024 mL) was added to the reaction mixture, and the reaction mixture was stirred at 95° C. overnight. A saturated aqueous solution of sodium hydrogen carbonate was added to the reaction mixture, and the reaction mixture was extracted with ethyl acetate. The obtained organic layer was washed with a saturated salt solution, and concentrated under reduced pressure after drying with anhydrous sodium sulfate. The obtained residue was purified by column chromatography on silica gel (hexane:ethyl acetate=25:75) to give the title compound (36 mg) having the following physical data.

TLC: Rf 0.46 (hexane:ethyl acetate=1:3);
$^1$H-NMR (CDCl$_3$): δ 2.82 (s, 3H), 3.91 (s, 3H), 4.77 (d, 1H), 4.81 (d, 1H), 6.34-6.50 (m, 1H), 6.65-6.78 (m, 1H), 6.87-7.00 (m, 1H), 7.06-7.25 (m, 3H), 7.46-7.60 (m, 2H), 7.61-7.70 (m, 2H), 7.79-7.89 (m, 3H), 7.92-8.06 (m, 2H).

Example 7

2-[3-[(4-methyl-1H-indol-3-yl)methyl]imidazo[1,2-a]pyridin-2-yl]-1-naphthoic acid

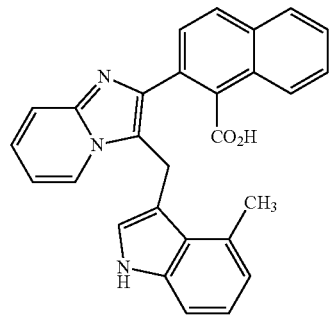 [SMILES: Cc1cccc2[nH]cc(Cc3c(-c4ccc5ccccc5c4C(=O)O)nc4ccccn34)c12]

An aqueous solution of 2 M sodium hydroxide (0.4 mL) was added to a solution of the compound prepared in Example 6 (36 mg) in ethanol (2 mL). The reaction mixture was irradiated by a microwave, and stirred at 100° C. for an hour. The reaction mixture was cooled on ice bath, and neutralized with 2 M hydrochloric acid (0.4 mL). The reaction mixture was extracted with methylene chloride. The obtained organic layer was washed with a saturated salt solution. The obtained extract was concentrated under reduced pressure after drying with anhydrous sodium sulfate. The compound of the present invention (32 mg) having the following physical data was obtained.

TLC: Rf 0.32 (methylene chloride:methanol=9:1);
$^1$H-NMR (DMSO-D$_6$): δ 2.68 (s, 3H), 4.73 (s, 2H), 6.46 (s, 1H), 6.71 (d, 1H), 6.93 (t, 1H), 7.03-7.28 (m, 2H), 7.49-7.73 (m, 4H), 7.74-7.86 (m, 1H), 7.93-8.15 (m, 3H), 8.24-8.42 (m, 1H), 10.8 (s, 1H).

Example 8

Methyl 2-acetylbenzoate

Methyl iodide (66.85 g) and potassium carbonate (118.40 g) were added to a solution of 2-acetylbenzoic acid (70.29 g) in dimethylformamide (500 mL) on ice bath, and the reaction mixture was stirred for an hour. The reaction mixture was filtered with Celite (trade name), and the filtrate was concentrated under reduced pressure. A saturated aqueous solution of ammonium chloride was added to the obtained residue, and the reaction mixture was extracted with ethyl acetate. The obtained organic layer was washed with water and a saturated salt solution, and concentrated under reduced pressure after drying with anhydrous sodium sulfate. The title compound (72.24 g) having the following physical data was obtained.
TLC: Rf 0.40 (hexane:ethyl acetate=3:1);
$^1$H-NMR (CDCl$_3$): δ 2.54 (s, 3H), 3.90 (s, 3H), 7.41 (dd, 1H), 7.45-7.61 (m, 2H), 7.84 (dd, 1H).

Example 9

Methyl 2-[3-(hydroxymethyl)-6-methylimidazo[1,2-a]pyridin-2-yl]benzoate

By the same procedure as a series of reactions of Example 2→Example 3→Example 4→Example 5, using 5-methyl-2-aminopyridine instead of 2-aminopyridine and using the compound prepared in Example 8 instead of the compound prepared in Example 1, the title compound having the following physical data was obtained.
TLC: Rf 0.13 (hexane:ethyl acetate=2:3);
$^1$H-NMR (CDCl$_3$): δ 2.38 (s, 3H), 2.72 (t, 1H), 3.77 (s, 3H), 4.77 (d, 2H), 7.08-7.12 (m, 1H), 7.37-7.61 (m, 4H), 7.93-7.96 (m, 1H), 8.08 (s, 1H).

Example 10

1,4-dimethyl-1H-indole

Methyl iodide (28.44 g) and cesium carbonate (82.26 g) were added to a solution of 4-methylindole (22.08 g) in dimethylformamide (200 mL), and the reaction mixture was stirred at room temperature overnight. The reaction mixture was filtered with Celite (trade name), and the filtrate was concentrated under reduced pressure. A saturated aqueous solution of ammonium chloride was added to the obtained residue, and the reaction mixture was extracted with ethyl acetate. The obtained organic layer was washed with water and a saturated salt solution, and concentrated under reduced pressure after drying with anhydrous sodium sulfate. The obtained residue was purified by column chromatography on silica gel (hexane:ethyl acetate=100:0→85:15) to give the title compound (20.83 g) having the following physical data.
TLC: Rf 0.79 (hexane:ethyl acetate=4:1);
$^1$H-NMR (CDCl$_3$): δ 2.55 (s, 3H), 3.78 (s, 3H), 6.49 (dd, 1H), 6.86-6.94 (m, 1H), 7.04 (d, 1H), 7.09-7.20 (m, 2H).

Example 11

2-{3-[(1,4-dimethyl-1H-indol-3-yl)methyl]-6-methylimidazo[1,2-a]pyridin-2-yl}benzoic acid By the same procedure as a series of reactions of Example 6→Example 7, using the compound prepared in Example 10 instead of 4-methylindole and using the compound prepared in Example 9 instead of the compound prepared in Example 5, the compound of the present invention having the following physical data was obtained.
TLC: Rf 0.22 (methylene chloride:methanol=10:1);
$^1$H-NMR (DMSO-D$_6$): δ 2.21 (s, 3H), 2.67 (s, 3H), 3.50 (s, 3H), 4.57 (s, 2H), 6.39 (s, 1H), 6.73 (d, 1H), 6.89-7.05 (m, 2H), 7.11 (d, 1H), 7.18-7.35 (m, 3H), 7.42-7.61 (m, 2H), 7.89 (s, 1H).

Example 12

Methyl 2-[3-(hydroxymethyl)imidazo[1,2-a]pyridin-2-yl]benzoate

By the same procedure as a series of reactions of Example 2→Example 3→Example 4→Example 5, using the compound prepared in Example 8 instead of the compound prepared in Example 1, the title compound having the following physical data was obtained.
TLC: Rf 0.45 (hexane:ethyl acetate=1:4);
$^1$H-NMR (CDCl$_3$): δ 2.78 (s, 3H), 3.57 (s, 3H), 3.71 (s, 3H), 4.67 (d, 2H), 6.26 (s, 1H), 6.65-6.76 (m, 1H), 6.82-6.92 (m, 1H), 7.07-7.22 (m, 3H), 7.34-7.47 (m, 2H), 7.47-7.54 (m, 1H), 7.59-7.69 (m, 1H), 7.77-7.88 (m, 2H).

Example 13

2-{3-[(1,4-dimethyl-1H-indol-3-yl)methyl]imidazo[1,2-a]pyridin-2-yl}benzoic acid By the same procedure as a series of reactions of Example 6→Example 7, using the compound prepared in Example 12 instead of the compound prepared in Example 5 and using the compound prepared in Example 10 instead of 4-methylindole, the compound of the present invention having the following physical data was obtained.
TLC: Rf 0.22 (ethyl acetate:methanol=4:1);
$^1$H-NMR (CDCl$_3$): δ 2.79 (s, 3H), 3.62 (s, 3H), 4.62-4.85 (m, 2H), 6.26 (s, 1H), 6.86-6.97 (m, 2H), 7.16-7.22 (m, 2H), 7.34-7.56 (m, 4H), 7.69-7.79 (m, 1H), 7.89-8.00 (m, 1H), 8.28-8.37 (m, 1H).

Example 14

1-ethyl-4-methyl-1H-indole

By the same procedure as a reaction of Example 10, using ethyl iodide instead of methyl iodide, the title compound having the following physical data was obtained.
TLC: Rf 0.48 (hexane:ethyl acetate=29:1);
$^1$H-NMR (CDCl$_3$): δ 1.46 (t, 3H), 2.55 (s, 3H), 4.17 (q, 2H), 6.48-6.52 (m, 1H), 6.86-6.93 (m, 1H), 7.07-7.16 (m, 2H), 7.20 (d, 1H).

Example 15

2-{3-[(1-ethyl-4-methyl-1H-indol-3-yl)methyl]imidazo[1,2-a]pyridin-2-yl}benzoic acid By the same procedure as a series of reactions of Example 6→Example 7, using the compound prepared in Example 14 instead of 4-methylindole and using the compound prepared in Example 12 instead of the compound prepared in Example 5, the compound of the present invention having the following physical data was obtained.
TLC: Rf 0.31 (methylene chloride:methanol=9:1);
$^1$H-NMR (DMSO-D$_6$): δ 1.10 (t, 3H), 2.67 (s, 3H), 3.92 (q, 2H), 4.65 (s, 2H), 6.46 (s, 1H), 6.73 (d, 1H), 6.97 (t, 2H), 7.17 (d, 1H), 7.31-7.56 (m, 4H), 7.67 (d, 1H), 7.77 (d, 1H), 8.24 (d, 1H).

Example 16

2-{6-fluoro-3-[(4-methyl-1H-indol-3-yl)methyl]imidazo[1,2-a]pyridin-2-yl}-1-naphthoic acid By the same procedure as a series of reactions of Example 3→Example 4→Example 5→Example 6→Example 7, using 5-fluoro-2-aminopyridine instead of 2-aminopyridine, the compound of the present invention having the following physical data was obtained.
TLC: Rf 0.43 (methylene chloride:methanol=10:1);
$^1$H-NMR (DMSO-D$_6$): δ 2.69 (s, 3H), 4.74 (s, 2H), 6.35 (s, 1H), 6.71 (d, 1H), 6.93 (t, 1H), 7.11 (d, 1H), 7.35-7.49 (m, 1H), 7.53-7.67 (m, 3H), 7.69-7.81 (m, 1H), 7.91-8.06 (m, 3H), 8.41-8.50 (m, 1H), 10.7 (d, 1H).

Example 17

7-chloro-5-fluoro-4-methyl-1H-indole

Under an atmosphere of argon, 4-chloro-2-fluoro-5-nitrotoluene (1.9 g) was dissolved with anhydrous tetrahydrofuran (100 mL), and the reaction mixture was stirred at −50° C. Vinylmagnesium bromide (1.0 M solution in tetrahydrofuran, 40 mL) was dropped to the reaction mixture. The reaction mixture was raised slowly to −20° C. for 40 minutes. A saturated aqueous solution of ammonium chloride was added to the reaction mixture, and the reaction mixture was extracted with ethyl acetate. The obtained organic layer was washed with water and a saturated salt solution. The obtained extract was concentrated under reduced pressure after drying with sodium sulfate. The obtained residue was purified by column chromatography on silica gel (hexane:ethyl acetate=95:5→91:9) to give the title compound (1.09 g) having the following physical data.

TLC: Rf 0.50 (hexane:ethyl acetate=5:1);
$^1$H-NMR (CDCl$_3$): δ 2.42 (d, 3H), 6.58 (dd, 1H), 6.98 (d, 1H), 7.26-7.31 (m, 1H), 8.30 (br s, 1H).

Example 18

5-fluoro-4-methyl-1H-indole

The compound prepared in Example 17 (500 mg) was dissolved with ethanol (9 mL). Triethylamine (0.46 mL) was added to the reaction mixture, and the reaction mixture was stirred at room temperature. Under an atmosphere of argon, 10% Pd—C (50% wet, 50 mg) was added to the reaction mixture. The reaction mixture was made an atmosphere of hydrogen from an atmosphere of argon, and stirred for 4.5 hours. The reaction mixture was filtered with Celite (trade name), and the filtrate was concentrated under reduced pressure. The obtained residue was purified by column chromatography on silica gel (hexane:ethyl acetate=98:2→91:9) to give the title compound (355 mg) having the following physical data.

TLC: Rf 0.37 (hexane:ethyl acetate=5:1);
$^1$H-NMR (CDCl$_3$): δ 2.46 (d, 3H), 6.48-6.59 (m, 1H), 6.86-6.97 (m, 1H), 7.12-7.18 (m, 1H), 7.22-7.25 (m, 1H), 8.12 (br s, 1H).

Example 19

2-{3-[(5-fluoro-4-methyl-1H-indol-3-yl)methyl]imidazo[1,2-a]pyridin-2-yl}benzoic acid By the same procedure as a series of reactions of Example 6→Example 7, using the compound prepared in Example 18 instead of 4-methylindole and using the compound prepared in Example 12 instead of the compound prepared in Example 5, the compound of the present invention having the following physical data was obtained.

TLC: Rf 0.56 (methylene chloride:methanol=10:1);
$^1$H-NMR (CDCl$_3$): δ 2.66 (s, 3H), 4.68 (s, 2H), 6.44 (s, 1H), 6.87 (t, 1H), 6.97 (t, 1H), 7.13 (dd, 1H), 7.29-7.38 (m, 1H), 7.39-7.52 (m, 3H), 7.73 (d, 1H), 7.89 (d, 1H), 8.12 (br s, 1H), 8.26 (d, 1H).

Example 20

2-{3-[(4-methyl-1H-indol-3-yl)methyl]imidazo[1,2-a]pyridin-2-yl}-1-naphthoic acid hydrochloride salt The compound prepared in Example 7 (190 mg) was dissolved with 4N hydrochloric acid/1,4-dioxane (9 mL). The reaction mixture was stirred for 5 minutes at room temperature. The reaction mixture was concentrated under reduced pressure. The obtained residue was dissolved with methanol, and concentrated under reduced pressure again. The compound of the present invention having the following physical data was obtained.

TLC: Rf 0.38 (methylene chloride:methanol=6:1);
$^1$H-NMR (DMSO-D$_6$): δ 2.65 (s, 3H), 4.72 (s, 2H), 6.59 (s, 1H), 6.70 (d, 1H), 6.92 (dd, 1H), 7.11 (d, 1H), 7.29-7.49 (m, 1H), 7.59-7.78 (m, 3H), 7.78-8.23 (m, 5H), 8.44-8.67 (m, 1H), 10.8 (d, 1H).

Example 21

2-{3-[(4-methyl-1H-indol-3-yl)methyl]imidazo[1,2-a]pyridin-2-yl}-1-naphthoic acid sodium salt An aqueous solution of 1 M sodium hydroxide (11.6 mL) was added to a solution of the compound prepared in Example 7 (5.0 g) in ethanol (100 mL)/water (50 mL). The reaction mixture was refluxed at 80° C. The reaction mixture was concentrated under reduced pressure after being cooled to room temperature. Water (30 mL) and ethanol (10 mL) was added to the obtained residue, and the reaction mixture was refluxed. The reaction mixture was cooled to room temperature, and the precipitated crystal was filtered. The obtained crystal was dried at 100° C. under reduced pressure. The compound of the present invention having the following physical data was obtained.

TLC: Rf 0.50 (methylene chloride:methanol:acetic acid=9:1:0.1);
$^1$H-NMR (DMSO-D$_6$): δ 2.66 (s, 3H), 4.75 (s, 2H), 6.24 (d, 1H), 6.66 (d, 1H), 6.73-6.81 (m, 1H), 6.87 (dd, 1H), 7.06 (d, 1H), 7.16 (dd, 1H), 7.33-7.50 (m, 3H), 7.55-7.69 (m, 2H), 7.73-7.83 (m, 1H), 7.99-8.17 (m, 2H), 10.6 (s, 1H).

Example 22

2-{3-[(1,4-dimethyl-1H-indol-3-yl)methyl]imidazo[1,2-a]pyridin-2-yl}benzoic acid sodium salt By the same procedure as a reaction of Example 21, using the compound prepared in Example 13, the compound of the present invention having the following physical data was obtained.

TLC: Rf 0.57 (methylene chloride:methanol:acetic acid=9:1:0.1);
$^1$H-NMR (DMSO-D$_6$): δ 2.65 (s, 3H), 3.49 (s, 3H), 4.58 (s, 2H), 6.48 (s, 1H), 6.66-6.83 (m, 2H), 6.95 (dd, 1H), 7.05-7.23 (m, 4H), 7.28 (dd, 1H), 7.45 (d, 1H), 7.53 (d, 1H), 8.00 (d, 1H).

Example 23-(1)~(4)

By the same procedure as a series of reactions of Example 10→Example 7→Example 20, using the corresponding alkyl halides instead of methyl iodide, the compounds of the present invention having the following physical data were obtained (in this regard, Example 23-(4) was obtained by the same procedure as a series of reactions of Example 10→Example 7).

Example 23-(1)

2-(3-{[4-methyl-1-(2-propanyl)-1H-indol-3-yl]methyl}imidazo[1,2-a]pyridin-2-yl)-1-naphthoic acid hydrochloride salt TLC: Rf 0.35 (methylene chloride:methanol=9:1);
$^1$H-NMR (DMSO-D$_6$): δ 1.10 (d, 6H), 2.68 (s, 3H), 4.31-4.60 (m, 1H), 4.76 (s, 2H), 6.48 (s, 1H), 6.72 (d, 1H), 6.84-7.02 (m, 2H), 7.18 (d, 1H), 7.24-7.41 (m, 1H), 7.48-7.73 (m, 4H), 7.86-8.12 (m, 3H), 8.25 (d, 1H).

Example 23-(2)

2-{3-[(4-methyl-1-propyl-1H-indol-3-yl)methyl]imidazo[1,2-a]pyridin-2-yl}-1-naphthoic acid hydrochloride salt TLC: Rf 0.40 (methylene chloride:methanol=9:1);
$^1$H-NMR (DMSO-D$_6$): δ 0.58 (t, 3H), 1.34-1.58 (m, 2H), 2.69 (s, 3H), 3.85 (t, 2H), 4.74 (s, 2H), 6.39 (s, 1H), 6.74 (d, 1H), 6.89 (t, 1H), 6.93-7.04 (m, 1H), 7.18 (d, 1H), 7.22-7.35 (m, 1H), 7.49-7.72 (m, 4H), 7.87-8.09 (m, 3H), 8.19 (d, 1H).

Example 23-(3)

2-{3-[(1-ethyl-4-methyl-1H-indol-3-yl)methyl]imidazo[1,2-a]pyridin-2-yl}-1-naphthoic acid hydrochloride salt TLC: Rf 0.51 (methylene chloride:methanol=9:1);
$^1$H-NMR (DMSO-D$_6$): δ 1.06 (t, 3H), 2.62 (s, 3H), 3.88 (q, 2H), 4.71 (s, 2H), 6.65 (s, 1H), 6.72 (d, 1H), 6.91-7.02 (m, 1H), 7.15 (d, 1H), 7.34-7.47 (m, 1H), 7.59 (d, 1H), 7.62-7.75 (m, 2H), 7.81-7.95 (m, 1H), 7.96-8.16 (m, 4H), 8.61 (d, 1H).

Example 23-(4)

2-[3-({4-methyl-1-[2-(4-morpholinyl)ethyl]-1H-indol-3-yl}methyl)imidazo[1,2-a]pyridin-2-yl]-1-naphthoic acid TLC: Rf 0.52 (methylene chloride:methanol=9:1);
$^1$H-NMR (DMSO-D$_6$): δ 2.12-2.27 (m, 4H), 2.40 (t, 2H), 2.70 (s, 3H), 3.20-3.35 (m, 4H), 4.01 (t, 2H), 4.73 (s, 2H), 6.43 (s, 1H), 6.74 (d, 1H), 6.88 (t, 1H), 6.94-7.03 (m, 1H), 7.20 (d, 1H), 7.23-7.36 (m, 1H), 7.47-7.73 (m, 4H), 7.88-7.98 (m, 2H), 8.01 (d, 1H), 8.18 (d, 1H).

Example 24

2-{3-[(5-fluoro-4-methyl-1H-indol-3-yl)methyl]imidazo[1,2-a]pyridin-2-yl}-1-naphthoic acid By the same procedure as a series of reactions of Example 6→Example 7, using the compound prepared in Example 18 instead of 4-methylindole, the compound of the present invention having the following physical data was obtained.
TLC: Rf 0.69 (methylene chloride:methanol=9:1);
$^1$H-NMR (DMSO-D$_6$): δ 2.56 (s, 3H), 4.74 (s, 2H), 6.34 (s, 1H), 6.77-6.91 (m, 2H), 7.02-7.13 (m, 1H), 7.18-7.30 (m, 1H), 7.45-7.66 (m, 4H), 7.79-7.94 (m, 2H), 8.04 (d, 1H), 8.12 (d, 1H), 10.8 (s, 1H).

Example 25

Methyl 2-[3-({4-methyl-1-[2-(tetrahydro-2H-pyran-2-yloxy)ethyl]-1H-indol-3-yl}methyl)imidazo[1,2-a]pyridin-2-yl]-1-naphthoate By the same procedure as a reaction of Example 10, using 2-(2-bromoethoxy)tetrahydro-2H-pyran instead of methyl iodide, the title compound having the following physical data was obtained.
TLC: Rf 0.33 (hexane:ethyl acetate=1:1);
$^1$H-NMR (CDCl$_3$): δ 1.17-1.63 (m, 6H), 2.80 (s, 3H), 3.27-3.38 (m, 1H), 3.48-3.63 (m, 2H), 3.83-3.94 (m, 4H), 4.02-4.21 (m, 2H), 4.32-4.40 (m, 1H), 4.79 (s, 2H), 6.43 (s, 1H), 6.72 (td, 1H), 6.86-6.94 (m, 1H), 7.09-7.24 (m, 3H), 7.46-7.60 (m, 2H), 7.62-7.71 (m, 2H), 7.78-7.91 (m, 3H), 7.96-8.05 (m, 1H).

Example 26

Methyl 2-(3-{[1-(2-hydroxyethyl)-4-methyl-1H-indol-3-yl]methyl}imidazo[1,2-a]pyridin-2-yl)-1-naphthoate The compound prepared in Example 25 (390 mg) was dissolved with acetic acid (12 mL) and water (3 mL). The reaction mixture was stirred at 80° C. for 1.5 hours. The reaction mixture was neutralized with an aqueous solution of 2N sodium hydroxide after being cooled to room temperature. The reaction mixture was extracted with ethyl acetate. The obtained organic layer was washed with a saturated salt solution. The obtained extract was concentrated under reduced pressure after drying with anhydrous sodium sulfate. The obtained residue was purified by column chromatography on silica gel (hexane:ethyl acetate=80:20→50:50→0:100, ethyl acetate:methanol=95:5→90:10) to give the title compound (320 mg) having the following physical data.
TLC: Rf 0.22 (hexane:ethyl acetate=1:4);
$^1$H-NMR (CDCl$_3$): δ 3.49 (s, 3H), 3.75-3.83 (m, 2H), 3.88 (s, 3H), 4.01-4.09 (m, 2H), 4.74-4.81 (m, 2H), 6.36 (s, 1H), 6.74 (td, 1H), 6.86-6.93 (m, 1H), 7.08-7.24 (m, 3H), 7.45-7.59 (m, 2H), 7.62 (d, 1H), 7.68 (dt, 1H), 7.79-7.91 (m, 3H), 7.94-8.02 (m, 1H).

Example 27

2-(3-{[1-(2-hydroxyethyl)-4-methyl-1H-indol-3-yl]methyl}imidazo[1,2-a]pyridin-2-yl)-1-naphthoic acid hydrochloride salt By the same procedure as a series of reactions of Example 7→Example 20, using the compound prepared in Example 26, the compound of the present invention having the following physical data was obtained.
TLC: Rf 0.23 (chloroform:methanol=9:1);
$^1$H-NMR (DMSO-D$_6$): δ 2.62 (s, 3H), 3.47 (t, 2H), 3.90 (t, 2H), 4.70 (s, 2H), 6.66 (s, 1H), 6.71 (d, 1H), 6.90-7.01 (m, 1H), 7.17 (d, 1H), 7.36-7.49 (m, 1H), 7.61 (d, 1H), 7.64-7.78 (m, 2H), 7.87-8.17 (m, 5H), 8.63 (d, 1H).

Example 28

Methyl 2-[3-({1-[3-(dimethylamino)-2-hydroxypropyl]-4-methyl-1H-indol-3-yl}methyl)imidazo[1,2-a]pyridin-2-yl]-1-naphthoate Sodium hydride (60% dispersion in mineral oil; 16 mg) was added to a solution of the compound prepared in Example 6 (150 mg) in dimethylformamide (3.4 mL) on the ice bath. The reaction mixture was stirred for a few minutes. Epibromohydrin (35 μL) was added to the reaction mixture on the ice bath, and the reaction mixture was stirred for 30 minutes. An aqueous solution of 1N sodium hydroxide (0.5 mL) was added to the reaction mixture. The reaction mixture was stirred at 70° C. overnight. 1N hydrochloric acid was added to the reaction mixture, and the reaction mixture was made the acidity. The water layer was washed with methylene chloride, and made the basicity with the aqueous solution of 1N sodium hydroxide. The reaction mixture was extracted with methylene chloride. The obtained organic layer was dried with anhydrous sodium sulfate, and concentrated under reduced pressure. The title compound (130 mg) having the following physical data was obtained.

TLC: Rf 0.45 (methylene chloride:methanol=9:1);
$^1$H-NMR (CDCl$_3$): δ 2.01 (dd, 1H), 2.08-2.16 (m, 7H), 2.80 (s, 3H), 3.25 (br, 1H), 3.78-3.88 (m, 1H), 3.91 (s, 3H), 3.92-4.00 (m, 2H), 4.79 (s, 2H), 6.35 (s, 1H), 6.72 (t, 1H), 6.90 (d, 1H), 7.09-7.25 (m, 3H), 7.45-7.59 (m, 2H), 7.60-7.73 (m, 2H), 7.77-7.91 (m, 3H), 8.00 (d, 1H).

Example 29

2-[3-({1-[3-(dimethylamino)-2-hydroxypropyl]-4-methyl-1H-indol-3-yl}methyl)imidazo[1,2-a]pyridin-2-yl]-1-naphthoic acid sodium salt By the same procedure as a series of reactions of Example 7→Example 21, using the compound prepared in Example 28, the compound of the present invention having the following physical data was obtained.

TLC: Rf 0.32 (ethyl acetate:acetic acid:water=3:1:1);
$^1$H-NMR (DMSO-D$_6$): δ 1.93-2.06 (m, 8H), 2.66 (s, 3H), 3.60-3.81 (m, 2H), 3.93-4.07 (m, 1H), 4.69 (s, 2H), 5.16-5.28 (m, 1H), 6.38 (s, 1H), 6.68 (d, 1H), 6.78 (t, 1H), 6.87-6.97 (m, 1H), 7.08-7.20 (m, 2H), 7.35-7.47 (m, 3H), 7.57-7.66 (m, 2H), 7.72-7.83 (m, 1H), 8.02-8.18 (m, 2H).

Example 30

Methyl 2-(3-{[1-(2,3-dihydroxypropyl)-4-methyl-1H-indol-3-yl]methyl}imidazo[1,2-a]pyridin-2-yl)-1-naphthoate Sodium hydride (60% dispersion in mineral oil; 16 mg) was added to a solution of the compound prepared in Example 6 (150 mg) in dimethylformamide (5 mL) at room temperature. The reaction mixture was stirred for a few minutes. Glycidol (0.1 mL) was added to the reaction mixture, and the reaction mixture was stirred at 80° C. for 30 minutes. Water was added to the reaction mixture. The reaction mixture was extracted with ethyl acetate. The obtained organic layer was washed with a saturated salt solution. The obtained extract was concentrated under reduced pressure after drying with anhydrous sodium sulfate. The obtained residue was purified by column chromatography on silica gel (column: main column L, inject column S (made in Yamazen Co.), ethyl acetate:methanol=100:0→90:10) to give the title compound (68 mg) having the following physical data.

TLC: Rf 0.45 (ethyl acetate);
$^1$H-NMR (CDCl$_3$): δ 2.80 (s, 3H), 3.29 (dd, 1H), 3.46 (dd, 1H), 3.80-3.93 (m, 4H), 3.93-4.03 (m, 2H), 4.78 (s, 2H), 6.32 (s, 1H), 6.75 (t, 1H), 6.89 (d, 1H), 7.06-7.24 (m, 3H), 7.45-7.59 (m, 2H), 7.60-7.73 (m, 2H), 7.80-7.91 (m, 3H), 7.96 (d, 1H).

Example 31

2-(3-{[1-(2,3-dihydroxypropyl)-4-methyl-1H-indol-3-yl]methyl}imidazo[1,2-a]pyridin-2-yl)-1-naphthoic acid hydrochloride salt By the same procedure as a series of reactions of Example 7→Example 20, using the compound prepared in Example 30, the compound of the present invention having the following physical data was obtained.

TLC: Rf 0.36 (methylene chloride:methanol=9:1);
$^1$H-NMR (DMSO-D$_6$): δ 2.63 (s, 3H), 3.07-3.27 (m, 2H), 3.51-3.63 (m, 1H), 3.74 (dd, 1H), 4.00 (dd, 1H), 4.70 (s, 2H), 6.57 (s, 1H), 6.72 (d, 1H), 6.90-7.05 (m, 1H), 7.19 (d, 1H), 7.21-7.38 (m, 1H), 7.55-8.19 (m, 8H), 8.39-8.56 (m, 1H).

Example 32-(1)~(47)

By the same procedure as a series of reactions of Example 10→Example 7, using the corresponding alkyl halides instead of methyl iodide, the compounds of the present invention having the following physical data were obtained.

Example 32-(1)

2-[3-({1-[2-(dimethylamino)ethyl]-4-methyl-1H-indol-3-yl}methyl)imidazo[1,2-a]pyridin-2-yl]-1-naphthoic acid TLC: Rf 0.39 (chloroform:methanol:aqueous ammonia=79:20:1);
$^1$H-NMR (CDCl$_3$): δ 2.39 (s, 6H), 2.67 (s, 3H), 2.95-3.00 (m, 2H), 4.10-4.15 (m, 2H), 4.46 (s, 2H), 6.66 (s, 1H), 6.72-6.75 (m, 1H), 6.79-6.81 (m, 1H), 7.05-7.06 (m, 2H), 7.18-7.22 (m, 1H), 7.42-7.48 (m, 2H), 7.58 (d, 1H), 7.70 (d, 1H), 7.83-7.89 (m, 3H), 8.11 (d, 1H).

Example 32-(2)

2-[3-({1-[3-(dimethylamino)propyl]-4-methyl-1H-indol-3-yl}methyl)imidazo[1,2-a]pyridin-2-yl]-1-naphthoic acid TLC: Rf 0.24 (chloroform:methanol:aqueous ammonia=79:20:1);
$^1$H-NMR (CDCl$_3$): δ 1.81-1.92 (m, 2H), 2.35 (s, 6H), 2.50-2.60 (m, 2H), 2.77 (s, 3H), 3.36-3.43 (m, 2H), 4.65 (s, 2H), 6.63-6.67 (m, 2H), 6.82 (d, 1H), 6.88 (d, 1H), 7.04 (dd, 1H), 7.15-7.22 (m, 1H), 7.38-7.46 (m, 2H), 7.54 (d, 1H), 7.67 (d, 1H), 7.74-7.82 (m, 3H), 8.13 (d, 1H).

Example 32-(3)

2-[3-({4-methyl-1-[2-(pyrrolidin-1-yl)ethyl]-1H-indol-3-yl}methyl)imidazo[1,2-a]pyridin-2-yl]-1-naphthoic acid TLC: Rf 0.50 (chloroform:methanol:aqueous ammonia=79:20:1);
$^1$H-NMR (CDCl$_3$): δ 1.79-1.90 (m, 4H), 2.68 (s, 3H), 2.82-3.00 (m, 2H), 3.19-3.30 (m, 2H), 4.09-4.19 (m, 2H), 4.48 (s, 2H), 6.70-6.75 (m, 2H), 6.77-6.81 (m, 1H), 7.02-7.05 (m, 2H), 7.14-7.19 (m, 1H), 7.39-7.45 (m, 2H), 7.52 (d, 1H), 7.61 (d, 1H), 7.76 (d, 1H), 7.80 (d, 1H), 7.87 (d, 1H), 8.09 (d, 1H).

Example 32-(4)

2-[3-({4-methyl-1-[2-(1-methylpyrrolidin-2-yl)ethyl]-1H-indol-3-yl}methyl)imidazo[1,2-a]pyridin-2-yl]-1-naphthoic acid TLC: Rf 0.23 (chloroform:methanol:aqueous ammonia=79:20:1);
$^1$H-NMR (DMSO-D$_6$): δ 1.19-1.28 (m, 1H), 1.43-1.56 (m, 3H), 1.60-1.69 (m, 1H), 1.81-1.89 (m, 1H), 1.91-2.00 (m, 1H), 2.02-2.08 (m, 4H), 2.66 (s, 3H), 2.83-2.88 (m, 1H), 3.87-3.91 (m, 2H), 4.70 (s, 2H), 6.41 (s, 1H), 6.73 (d, 1H), 6.82 (dd, 1H), 6.97 (dd, 1H), 7.12 (d, 1H), 7.23 (dd, 1H), 7.50-7.60 (m, 4H), 7.87-7.92 (m, 2H), 8.03 (d, 1H), 8.09 (d, 1H).

Example 32-(5)

2-[3-({4-methyl-1-[2-(piperidin-1-yl)ethyl]-1H-indol-3-yl}methyl)imidazo[1,2-a]pyridin-2-yl]-1-naphthoic acid TLC: Rf 0.53 (chloroform:methanol:aqueous ammonia=79:20:1);
$^1$H-NMR (CDCl$_3$): δ 1.54-1.66 (m, 2H), 1.72-1.85 (m, 4H), 2.71 (s, 3H), 2.97-3.12 (m, 4H), 3.37-3.46 (m, 2H), 4.28-4.41 (m, 2H), 4.62 (s, 2H), 6.71 (s, 1H), 6.78 (d, 1H), 6.84-6.93 (m, 1H), 6.98-7.08 (m, 1H), 7.21 (d, 1H), 7.30-7.40 (m, 1H), 7.43-7.51 (m, 2H), 7.55 (d, 1H), 7.65 (d, 1H), 7.86 (d, 2H), 8.05 (d, 1H), 8.15 (d, 1H).

Example 32-(6)

2-(3-{[4-methyl-1-(2-phenoxyethyl)-1H-indol-3-yl]methyl}imidazo[1,2-a]pyridin-2-yl)-1-naphthoic acid TLC: Rf 0.70 (chloroform:methanol:acetic acid=79:20:1);
$^1$H-NMR (CDCl$_3$): δ 2.65 (s, 3H), 4.12-4.18 (m, 2H), 4.33-4.41 (m, 2H), 7.23 (s, 2H), 6.12 (s, 1H), 6.63-6.71 (m, 4H), 6.85-6.95 (m, 4H), 7.13 (dd, 1H), 7.19-7.23 (m, 2H), 7.27-7.38 (m, 2H), 7.46 (d, 1H), 7.68 (d, 1H), 7.71 (d, 1H), 7.96-8.02 (m, 1H), 8.10 (d, 1H).

Example 32-(7)

2-[3-({1-[(3R)-3-hydroxy-3-phenylpropyl]-4-methyl-1H-indol-3-yl}methyl)imidazo[1,2-a]pyridin-2-yl]-1-naphthoic acid TLC: Rf 0.50 (chloroform:methanol:aqueous ammonia=79:20:1);
$^1$H-NMR (DMSO-D$_6$): δ 1.81-1.87 (m, 2H), 2.64 (s, 3H), 3.88-4.06 (m, 2H), 4.33-4.47 (m, 1H), 4.70 (s, 2H), 6.44 (s, 1H), 6.71 (d, 1H), 6.79-6.82 (m, 1H), 6.92-6.96 (m, 1H), 7.08 (d, 1H), 7.12-7.17 (m, 3H), 7.19-7.23 (m, 3H), 7.47-7.59 (m, 4H), 7.81 (d, 1H), 7.86 (d, 1H), 8.04 (d, 1H), 8.09 (d, 1H).

Example 32-(8)

2-[3-({1-[(3S)-3-hydroxy-3-phenylpropyl]-4-methyl-1H-indol-3-yl}methyl)imidazo[1,2-a]pyridin-2-yl]-1-naphthoic acid TLC: Rf 0.50 (chloroform:methanol:aqueous ammonia=79:20:1);
$^1$H-NMR (DMSO-D$_6$): δ 1.81-1.87 (m, 2H), 2.64 (s, 3H), 3.88-4.06 (m, 2H), 4.33-4.47 (m, 1H), 4.70 (s, 2H), 6.44 (s, 1H), 6.71 (d, 1H), 6.79-6.82 (m, 1H), 6.92-6.96 (m, 1H), 7.08 (d, 1H), 7.12-7.17 (m, 3H), 7.19-7.23 (m, 3H), 7.47-7.59 (m, 4H), 7.81 (d, 1H), 7.86 (d, 1H), 8.04 (d, 1H), 8.09 (d, 1H).

Example 32-(9)

2-[3-({1-[2-(4-fluorophenyl)ethyl]-4-methyl-1H-indol-3-yl}methyl)imidazo[1,2-a]pyridin-2-yl]-1-naphthoic acid TLC: Rf 0.50 (chloroform:methanol:aqueous ammonia=79:20:1);
$^1$H-NMR (CDCl$_3$): δ 2.64 (s, 3H), 2.81 (t, 2H), 4.10 (t, 2H), 4.67 (s, 2H), 6.33 (s, 1H), 6.71 (d, 1H), 6.81-6.87 (m, 3H), 6.92-7.04 (m, 3H), 7.12 (d, 1H), 7.22-7.26 (m, 1H), 7.50-7.59 (m, 4H), 7.87-7.92 (m, 2H), 8.03-8.05 (m, 2H).

Example 32-(10)

2-[3-({4-methyl-1-[2-(tetrahydro-2H-pyran-4-yl)ethyl]-1H-indol-3-yl}methyl)imidazo[1,2-a]pyridin-2-yl]-1-naphthoic acid TLC: Rf 0.49 (chloroform:methanol:aqueous ammonia=79:20:1);
$^1$H-NMR (DMSO-D$_6$): δ 0.99-1.10 (m, 2H), 1.18-1.27 (m, 1H), 1.36-1.39 (dd, 2H), 1.43-1.48 (dt, 2H), 2.66 (s, 3H), 3.05 (t, 2H), 3.65-3.69 (m, 2H), 3.88 (t, 2H), 4.71 (s, 2H), 6.39 (s, 1H), 6.72 (d, 1H), 6.81-6.84 (m, 1H), 6.94-6.97 (m, 1H), 7.11 (d, 1H), 7.21-7.25 (m, 1H), 7.49-7.59 (m, 4H), 7.86 (d, 1H), 7.90 (d, 1H), 8.05 (d, 1H), 8.10 (d, 1H).

Example 32-(11)

2-[3-({1-[2-(2,3-dihydro-1-benzofuran-5-yl)ethyl]-4-methyl-1H-indol-3-yl}methyl)imidazo[1,2-a]pyridin-2-yl]-1-naphthoic acid TLC: Rf 0.54 (chloroform:methanol:aqueous ammonia=79:20:1);
$^1$H-NMR (DMSO-D$_6$): δ 2.64 (s, 3H), 2.72 (t, 2H), 2.99 (t, 2H), 4.04 (t, 2H), 4.40 (t, 2H), 4.68 (s, 2H), 6.38 (s, 1H), 6.46 (d, 1H), 6.67 (d, 1H), 6.71 (d, 1H), 6.79-6.82 (m, 1H), 6.87 (s, 1H), 6.94 (dd, 1H), 7.12 (d, 1H), 7.20-7.24 (m, 1H), 7.48-7.58 (m, 4H), 7.82 (d, 1H), 7.88 (d, 1H), 8.03-8.07 (m, 2H).

Example 32-(12)

2-(3-{[4-methyl-1-(3-phenylpropyl)-1H-indol-3-yl]methyl}imidazo[1,2-a]pyridin-2-yl)-1-naphthoic acid TLC: Rf 0.53 (chloroform:methanol:aqueous ammonia=79:20:1);
$^1$H-NMR (DMSO-D$_6$): δ 1.80-1.87 (m, 2H), 2.35 (t, 2H), 2.65 (s, 3H), 3.87 (t, 2H), 4.72 (s, 2H), 6.40 (s, 1H), 6.72 (d, 1H), 6.79-6.83 (m, 1H), 6.93-6.97 (m, 3H), 7.07-7.12 (m, 2H), 7.15-7.24 (m, 3H), 7.48-7.60 (m, 4H), 7.83 (d, 1H), 7.87 (d, 1H), 8.04 (d, 1H), 8.12 (d, 1H).

Example 32-(13)

2-(3-{[4-methyl-1-(piperidin-4-ylmethyl)-1H-indol-3-yl]methyl}imidazo[1,2-a]pyridin-2-yl)-1-naphthoic acid TLC: Rf 0.53 (chloroform:ethanol:water=3:7:4);
$^1$H-NMR (DMSO-D$_6$): δ 0.99-1.11 (m, 2H), 1.27-1.31 (m, 2H), 1.70-1.80 (m, 1H), 2.40-2.50 (d, 2H), 2.66 (s, 3H), 2.91-2.94 (m, 2H), 3.75 (d, 2H), 4.69 (s, 2H), 6.34 (s, 1H), 6.72 (d, 1H), 6.79-6.82 (m, 1H), 6.93-6.97 (m, 1H), 7.13 (d, 1H), 7.20-7.24 (m, 1H), 7.49-7.59 (m, 4H), 7.81 (d, 1H), 7.86 (d, 1H), 8.07-8.08 (m, 2H).

Example 32-(14)

2-(3-{[1-(3-hydroxypropyl)-4-methyl-1H-indol-3-yl]methyl}imidazo[1,2-a]pyridin-2-yl)-1-naphthoic acid TLC: Rf 0.23 (chloroform:methanol:aqueous ammonia=79:20:1);
$^1$H-NMR (CDCl$_3$): δ 1.63-1.69 (m, 2H), 2.64 (s, 3H), 3.23 (t, 2H), 3.92 (t, 2H), 4.69 (s, 2H), 6.42 (s, 1H), 6.71 (d, 1H), 6.80-6.83 (m, 1H), 6.95 (dd, 1H), 7.13 (d, 1H), 7.19-7.23 (m, 1H), 7.49-7.59 (m, 4H), 7.84 (d, 1H), 7.88 (d, 1H), 8.05-8.09 (m, 2H).

Example 32-(15)

2-[3-({1-[2-(dipropan-2-ylamino)ethyl]-4-methyl-1H-indol-3-yl}methyl)imidazo[1,2-a]pyridin-2-yl]-1-naphthoic acid TLC: Rf 0.35 (chloroform:methanol:aqueous ammonia=79:20:1);
$^1$H-NMR (DMSO-D$_6$): δ 0.68 (d, 12H), 2.71 (s, 3H), 2.77-2.85 (m, 2H), 3.15-3.62 (m, 2H), 3.80-3.90 (m, 2H), 4.73 (s, 2H), 6.40 (s, 1H), 6.74 (d, 1H), 6.86-6.89 (m, 1H), 6.97-7.01 (m, 1H), 7.16 (d, 1H), 7.25-7.29 (m, 1H), 7.54-7.65 (m, 4H), 7.92-8.02 (m, 3H), 8.17 (d, 1H).

Example 32-(16)

2-[3-({4-methyl-1-[2-(piperazin-1-yl)ethyl]-1H-indol-3-yl}methyl)imidazo pyridin-2-yl]-1-naphthoic acid TLC: Rf 0.44 (chloroform:ethanol:water=3:7:4);
$^1$H-NMR (DMSO-D$_6$): δ 2.31-2.33 (m, 4H), 2.50 (t, 2H), 2.62-2.69 (m, 7H), 3.97 (t, 2H), 4.69 (s, 2H), 6.48 (s, 1H), 6.73 (d, 1H), 6.80-6.84 (m, 1H), 6.94-6.98 (m, 1H), 7.15 (s, 1H), 7.21-7.25 (m, 1H), 7.50-7.59 (m, 4H), 7.86-7.91 (m, 2H), 8.05-8.07 (m, 2H).

Example 32-(17)

2-[3-({4-methyl-1-[2-(2-oxopyrrolidin-1-yl)ethyl]-1H-indol-3-yl}methyl)imidazo[1,2-a]pyridin-2-yl]-1-naphthoic acid TLC: Rf 0.44 (chloroform:methanol:aqueous ammonia=79:20:1);
$^1$H-NMR (DMSO-D$_6$): δ 1.48-1.55 (m, 2H), 1.91 (m, 2H), 2.66 (s, 3H), 2.80 (t, 2H), 3.30 (t, 2H), 4.01 (t, 2H), 4.71 (s, 2H), 6.40 (s, 1H), 6.75 (d, 1H), 6.82-6.85 (m, 1H), 6.96-7.00 (m, 1H), 7.15 (d, 1H), 7.22-7.26 (m, 1H), 7.50-7.61 (m, 4H), 7.88-7.92 (m, 2H), 8.03 (d, 1H), 8.11 (d, 1H).

Example 32-(18)

2-[3-({1-[2-(1,1-dioxidethiomorpholin-4-yl)ethyl]-4-methyl-1H-indol-3-yl}methyl)imidazo[1,2-a]pyridin-2-yl]-1-naphthoic acid TLC: Rf 0.26 (chloroform:methanol:aqueous ammonia=79:20:1);
$^1$H-NMR (DMSO-D$_6$): δ 2.63 (t, 2H), 2.66 (s, 3H), 2.71-2.78 (m, 8H), 3.95 (t, 2H), 4.71 (s, 2H), 6.46 (s, 1H), 6.72 (d, 1H), 6.81-6.85 (m, 1H), 6.94-6.98 (m, 1H), 7.15 (d, 1H), 7.20-7.24 (m, 1H), 7.49-7.59 (m, 4H), 7.86 (d, 1H), 7.89 (d, 1H), 8.05 (d, 1H), 8.11 (d, 1H).

Example 32-(19)

2-[3-({1-[2-(3,4-dihydroisoquinolin-2(1H)-yl)ethyl]-4-methyl-1H-indol-3-yl}methyl)imidazo[1,2-a]pyridin-2-yl]-1-naphthoic acid TLC: Rf 0.43 (chloroform:methanol:aqueous ammonia=79:20:1);
$^1$H-NMR (DMSO-D$_6$): δ 2.55-2.57 (m, 4H), 2.62-2.66 (m, 5H), 3.46 (s, 2H), 4.06 (t, 2H), 4.68 (s, 2H), 6.48 (s, 1H), 6.70-6.73 (m, 2H), 6.89 (d, 1H), 6.94-6.98 (m, 2H), 7.01-7.05 (m, 2H), 7.16-7.20 (m, 2H), 7.50-7.58 (m, 4H), 7.80 (d, 1H), 7.88 (d, 1H), 8.00 (d, 1H), 8.08 (d, 1H).

Example 32-(20)

2-{3-[(1-{2-[2-(diethylamino)ethoxy]ethyl}-4-methyl-1H-indol-3-yl)methyl]imidazo[1,2-a]pyridin-2-yl}-1-naphthoic acid TLC: Rf 0.15 (chloroform:methanol:aqueous ammonia=79:20:1);
$^1$H-NMR (DMSO-D$_6$): δ 0.85 (t, 6H), 2.41 (q, 4H), 2.46-2.50 (m, 2H), 2.67 (s, 3H), 3.28 (t, 2H), 3.50 (t, 2H), 4.00 (t, 2H), 4.70 (s, 2H), 6.51 (s, 1H), 6.73 (d, 1H), 6.80-6.83 (m, 1H), 6.93-6.97 (m, 1H), 7.14 (d, 1H), 7.20-7.24 (m, 1H), 7.50-7.58 (m, 4H), 7.87 (d, 1H), 7.90 (d, 1H), 8.05-8.10 (m, 2H).

Example 32-(21)

2-[3-({4-methyl-1-[2-(1-methyl-1H-pyrazol-4-yl)ethyl]-1H-indol-3-yl}methyl)imidazo[1,2-a]pyridin-2-yl]-1-naphthoic acid TLC: Rf 0.36 (chloroform:methanol:aqueous ammonia=79:20:1);
$^1$H-NMR (DMSO-D$_6$): δ 2.62-2.66 (m, 5H), 3.62 (s, 3H), 4.00 (t, 2H), 4.69 (s, 2H), 6.41 (s, 1H), 6.72 (d, 1H), 6.81-6.85 (m, 1H), 6.93-6.97 (m, 1H), 7.01 (s, 1H), 7.13 (d, 1H), 7.16 (s, 1H), 7.22-7.25 (m, 1H), 7.50-7.59 (m, 4H), 7.87 (d, 1H), 7.90 (d, 1H), 8.04 (d, 1H), 8.08 (d, 1H).

Example 32-(22)

2-{3-[(1-{2-[2-(dimethylamino)ethoxy]ethyl}-4-methyl-1H-indol-3-yl)methyl]imidazo[1,2-a]pyridin-2-yl}-1-naphthoic acid TLC: Rf 0.08 (chloroform:methanol:aqueous ammonia=79:20:1);
$^1$H-NMR (DMSO-D$_6$): δ 2.13 (s, 6H), 2.32 (t, 2H), 2.68 (s, 3H), 3.31 (t, 2H), 3.50 (t, 2H), 4.00 (t, 2H), 4.70 (s, 2H), 6.57 (s, 1H), 6.73 (d, 1H), 6.80-6.83 (m, 1H), 6.93-6.97 (m, 1H), 7.14 (d, 1H), 7.20-7.24 (m, 1H), 7.49-7.59 (m, 4H), 7.87-7.91 (m, 2H), 8.07-8.10 (m, 2H).

Example 32-(23)

2-(3-{[4-methyl-1-(4-methylpent-3-en-1-yl)-1H-indol-3-yl]methyl}imidazo[1,2-a]pyridin-2-yl)-1-naphthoic acid TLC: Rf 0.69 (chloroform:methanol:aqueous ammonia=79:20:1);
$^1$H-NMR (DMSO-D$_6$): δ 1.30 (s, 3H), 1.45 (s, 3H), 2.19 (dt, 2H), 2.66 (s, 3H), 3.85 (t, 2H), 4.70 (s, 2H), 4.90 (t, 1H), 6.37 (s, 1H), 6.72 (d, 1H), 6.81-6.84 (m, 1H), 6.94-6.98 (m, 1H), 7.12 (d, 1H), 7.21-7.25 (m, 1H), 7.50-7.59 (m, 4H), 7.87-7.91 (m, 2H), 8.03 (d, 1H), 8.09 (d, 1H).

Example 32-(24)

2-[3-({1-[2-(3-fluorophenyl)ethyl]-4-methyl-1H-indol-3-yl}methyl)imidazo[1,2-a]pyridin-2-yl]-1-naphthoic acid TLC: Rf 0.66 (chloroform:methanol:aqueous ammonia=79:20:1);
$^1$H-NMR (CDCl$_3$): δ 2.67 (s, 3H), 2.95 (t, 2H), 4.13 (t, 2H), 4.55 (s, 2H), 6.07 (s, 1H), 6.65 (d, 1H), 6.77-6.83 (m, 4H), 7.01 (d, 1H), 7.06-7.14 (m, 3H), 7.27-7.38 (m, 3H), 7.54 (d, 1H), 7.68 (d, 1H), 7.73 (d, 1H), 7.89 (d, 1H), 8.15 (d, 1H).

Example 32-(25)

2-[3-({4-methyl-1-[2-(1H-pyrazol-1-yl)ethyl]-1H-indol-3-yl}methyl)imidazo[1,2-a]pyridin-2-yl]-1-naphthoic acid TLC: Rf 0.61 (chloroform:methanol:aqueous ammonia=79:20:1);
$^1$H-NMR (DMSO-D$_6$): δ 2.63 (s, 3H), 4.24-4.32 (m, 4H), 4.63 (s, 2H), 5.89-5.90 (m, 1H), 6.14 (s, 1H), 6.73 (d, 1H), 6.82-6.86 (m, 1H), 6.93-6.97 (m, 1H), 7.07 (d, 1H), 7.13 (d, 1H), 7.21 (d, 1H), 7.23-7.27 (m, 1H), 7.51-7.60 (m, 4H), 7.89-7.94 (m, 2H), 8.01-8.03 (m, 2H).

Example 32-(26)

2-[3-({1-[2-(azepan-1-yl)ethyl]-4-methyl-1H-indol-3-yl}methyl)imidazo[1,2-a]pyridin-2-yl]-1-naphthoic acid TLC: Rf 0.67 (chloroform:methanol:aqueous ammonia=79:20:1);
$^1$H-NMR (DMSO-D$_6$): δ 1.35-1.41 (m, 8H), 2.44-2.50 (m, 4H), 2.63-2.66 (m, 5H), 3.92 (t, 2H), 4.69 (s, 2H), 6.49 (s, 1H), 6.72 (d, 1H), 6.81-6.84 (m, 1H), 6.94-6.98 (m, 1H), 7.13 (d, 1H), 7.21-7.25 (m, 1H), 7.51-7.59 (m, 4H), 7.87-7.92 (m, 2H), 8.03 (d, 1H), 8.11 (d, 1H).

Example 32-(27)

2-{3-[(4-methyl-1-{2-[methyl(phenyl)amino]ethyl}-1H-indol-3-yl)methyl]imidazo[1,2-a]pyridin-2-yl}-1-naphthoic acid TLC: Rf 0.66 (chloroform:methanol:aqueous ammonia=79:20:1);
$^1$H-NMR (DMSO-D$_6$): δ 2.48 (s, 3H), 2.65 (s, 3H), 3.42 (t, 2H), 4.04 (t, 2H), 4.69 (s, 2H), 6.37 (s, 1H), 6.45 (d, 2H), 6.53-6.57 (m, 1H), 6.73 (d, 1H), 6.79-6.82 (m, 1H), 6.92-6.96 (m, 1H), 7.00-7.07 (m, 3H), 7.21-7.25 (m, 1H), 7.49-7.59 (m, 4H), 7.83 (d, 1H), 7.89 (d, 1H), 8.03-8.07 (m, 2H).

Example 32-(28)

2-[3-({1-[2-(1H-imidazol-1-yl)ethyl]-4-methyl-1H-indol-3-yl}methyl)imidazo[1,2-a]pyridin-2-yl]-1-naphthoic acid TLC: Rf 0.52 (chloroform:methanol:aqueous ammonia=79:20:1);
$^1$H-NMR (DMSO-D$_6$): δ 2.63 (s, 3H), 4.14 (t, 2H), 4.24 (t, 2H), 4.66 (s, 2H), 6.31 (s, 1H), 6.65 (s, 1H), 6.73-6.75 (m, 2H), 6.84-6.87 (m, 1H), 6.93-6.97 (m, 1H), 7.11 (d, 1H), 7.16-7.18 (m, 1H), 7.23-7.27 (m, 1H), 7.53-7.59 (m, 4H), 7.90-7.94 (m, 2H), 8.01-8.06 (m, 2H).

Example 32-(29)

2-[3-({4-methyl-1-[2-(pyridin-4-yl)ethyl]-1H-indol-3-yl}methyl)imidazo[1,2-a]pyridin-2-yl]-1-naphthoic acid TLC: Rf 0.60 (chloroform:methanol:aqueous ammonia=79:20:1);
$^1$H-NMR (DMSO-D$_6$): δ 2.61 (s, 3H), 2.84 (t, 2H), 4.11 (t, 2H), 4.72 (s, 2H), 6.54 (s, 1H), 6.66 (d, 1H), 6.72-6.76 (m, 1H), 6.85-6.89 (m, 1H), 6.97 (d, 2H), 7.06 (d, 1H), 7.12-7.16 (m, 1H), 7.34-7.37 (m, 3H), 7.53-7.57 (m, 2H), 7.72-7.74 (m, 1H), 7.97 (d, 1H), 8.22-8.24 (m, 3H).

Example 32-(30)

2-[3-({1-[2-(2-methoxyethoxy)ethyl]-4-methyl-1H-indol-3-yl}methyl)imidazo[1,2-a]pyridin-2-yl]-1-naphthoic acid TLC: Rf 0.63 (chloroform:methanol:aqueous ammonia=79:20:1);
$^1$H-NMR (DMSO-D$_6$): δ 2.64 (s, 3H), 3.09 (s, 3H), 3.21 (t, 2H), 3.30 (t, 2H), 3.52 (t, 2H), 4.00 (t, 2H), 4.70 (s, 2H), 6.42 (s, 1H), 6.72 (d, 1H), 6.81-6.84 (m, 1H), 6.93-6.97 (m, 1H), 7.15 (d, 1H), 7.21-7.25 (m, 1H), 7.50-7.59 (m, 4H), 7.85-7.91 (m, 2H), 8.04 (d, 1H), 8.10 (d, 1H).

Example 32-(31)

2-[3-({4-methyl-1-[2-(thiophen-3-yl)ethyl]-1H-indol-3-yl}-methyl)imidazo[1,2-a]pyridin-2-yl]-1-naphthoic acid TLC: Rf 0.67 (chloroform:methanol:aqueous ammonia=79:20:1);
$^1$H-NMR (DMSO-D$_6$): δ 2.64 (s, 3H), 2.85 (t, 2H), 4.10 (t, 2H), 4.68 (s, 2H), 6.37 (s, 1H), 6.72 (d, 1H), 6.76 (d, 1H), 6.81-6.84 (m, 1H), 6.90-6.96 (m, 2H), 7.13 (d, 1H), 7.21-7.25 (m, 2H), 7.49-7.59 (m, 4H), 7.86 (d, 1H), 7.88 (d, 1H), 8.04-8.07 (m, 2H).

Example 32-(32)

2-[3-({4-methyl-1-[2-(thiophen-2-yl)ethyl]-1H-indol-3-yl}methyl)imidazo[1,2-a]pyridin-2-yl]-1-naphthoic acid TLC: Rf 0.68 (chloroform:methanol:aqueous ammonia=79:20:1);
$^1$H-NMR (DMSO-D$_6$): δ 2.64 (s, 3H), 3.05 (t, 2H), 4.05 (t, 2H), 4.67 (s, 2H), 6.38 (s, 1H), 6.61-6.62 (m, 1H), 6.72-6.76 (m, 2H), 6.81-6.84 (m, 1H), 6.93-6.97 (m, 1H), 7.11-7.14 (m, 2H), 7.21-7.25 (m, 1H), 7.50-7.59 (m, 4H), 7.86 (d, 1H), 7.90 (d, 1H), 8.03-8.06 (m, 2H).

Example 32-(33)

2-(3-{[4-methyl-1-(3-methylbut-3-en-1-yl)-1H-indol-3-yl]methyl}imidazo[1,2-a]pyridin-2-yl)-1-naphthoic acid TLC: Rf 0.64 (chloroform:methanol:aqueous ammonia=79:20:1);
$^1$H-NMR (DMSO-D$_6$): δ 1.53 (s, 3H), 2.22 (t, 2H), 2.65 (s, 3H), 3.97 (t, 2H), 4.45 (s, 1H), 4.55 (s, 1H), 4.69 (s, 2H), 6.40 (s, 1H), 6.72 (d, 1H), 6.81-6.85 (m, 1H), 6.95-6.98 (m, 1H), 7.13 (d, 1H), 7.22-7.26 (m, 1H), 7.51-7.59 (m, 4H), 7.89 (d, 1H), 7.91 (d, 1H), 8.03 (d, 1H), 8.09 (d, 1H).

Example 32-(34)

2-[3-({4-methyl-1-[2-(2-oxoimidazolidin-1-yl)ethyl]-1H-indol-3-yl}methyl)imidazo[1,2-a]pyridin-2-yl]-1-naphthoic acid TLC: Rf 0.57 (chloroform:methanol:aqueous ammonia=79:20:1);
$^1$H-NMR (DMSO-D$_6$): δ 2.65 (s, 3H), 2.88-2.90 (m, 4H), 3.20 (t, 2H), 3.99 (t, 2H), 4.70 (s, 2H), 5.81 (s, 1H), 6.43 (s, 1H), 6.74 (d, 1H), 6.82-6.85 (m, 1H), 6.96-7.00 (m, 1H), 7.18 (d, 1H), 7.22-7.26 (m, 1H), 7.51-7.61 (m, 4H), 7.89-7.93 (m, 2H), 8.03 (d, 1H), 8.10 (d, 1H).

Example 32-(35)

2-(3-{[1-(but-3-en-1-yl)-4-methyl-1H-indol-3-yl]methyl}imidazo[1,2-a]pyridin-2-yl)-1-naphthoic acid TLC: Rf 0.63 (chloroform:methanol:aqueous ammonia=79:20:1);

$^1$H-NMR (DMSO-D$_6$): δ 2.23-2.29 (m, 2H), 2.64 (s, 3H), 3.92 (t, 2H), 4.69 (s, 2H), 4.77-4.85 (m, 2H), 5.50-5.61 (m, 1H), 6.40 (s, 1H), 6.72 (d, 1H), 6.81-6.85 (m, 1H), 6.94-6.98 (m, 1H), 7.13 (d, 1H), 7.22-7.26 (m, 1H), 7.51-7.59 (m, 4H), 7.87-7.92 (m, 2H), 8.03 (d, 1H), 8.09 (d, 1H).

Example 32-(36)

2-[3-({4-methyl-1-[(3Z)-pent-3-en-1-yl]-1H-indol-3-yl}methyl)imidazo[1,2-a]pyridin-2-yl]-1-naphthoic acid TLC: Rf 0.67 (chloroform:methanol:aqueous ammonia=79:20:1);

$^1$H-NMR (DMSO-D$_6$): δ 1.29 (d, 3H), 2.23-2.28 (m, 2H), 2.65 (s, 3H), 3.89 (t, 2H), 4.70 (s, 2H), 5.12-5.17 (m, 1H), 5.23-5.28 (m, 1H), 6.38 (s, 1H), 6.72 (d, 1H), 6.81-6.85 (m, 1H), 6.94-6.98 (m, 1H), 7.14 (d, 1H), 7.22-7.26 (m, 1H), 7.52-7.60 (m, 4H), 7.88-7.92 (m, 2H), 8.03 (d, 1H), 8.09 (d, 1H).

Example 32-(37)

2-[3-({4-methyl-1-[3-(pyridin-2-yl)propyl]-1H-indol-3-yl}methyl)imidazo[1,2-a]pyridin-2-yl]-1-naphthoic acid TLC: Rf 0.60 (chloroform:methanol:aqueous ammonia=79:20:1);

$^1$H-NMR (DMSO-D$_6$): δ 1.91-1.98 (m, 2H), 2.50 (t, 2H), 2.66 (s, 3H), 3.92 (t, 2H), 4.71 (s, 2H), 6.42 (s, 1H), 6.73 (d, 1H), 6.80-6.83 (m, 1H), 6.95-6.97 (m, 2H), 7.08-7.11 (m, 2H), 7.20-7.24 (m, 1H), 7.49-7.60 (m, 5H), 7.86-7.90 (m, 2H), 8.02 (d, 1H), 8.12 (d, 1H), 8.37 (d, 1H).

Example 32-(38)

2-(3-{[1-(3,4-dihydroxybutyl)-4-methyl-1H-indol-3-yl]methyl}imidazo[1,2-a]pyridin-2-yl)-1-naphthoic acid TLC: Rf 0.49 (chloroform:methanol:aqueous ammonia=79:20:1);

$^1$H-NMR (DMSO-D$_6$): δ 1.46-1.55 (m, 1H), 1.67-1.76 (m, 1H), 2.63 (s, 3H), 3.10-3.33 (m, 3H), 3.92-3.99 (m, 2H), 4.69 (s, 2H), 6.43 (s, 1H), 6.71 (d, 1H), 6.80-6.83 (m, 1H), 6.93-6.97 (m, 1H), 7.14 (d, 1H), 7.20-7.23 (m, 1H), 7.49-7.59 (m, 4H), 7.85 (d, 1H), 7.89 (d, 1H), 8.04-8.08 (m, 2H).

Example 32-(39)

2-[3-({1-[2-(diethylamino)ethyl]-4-methyl-1H-indol-3-yl}methyl)imidazo[1,2-a]pyridin-2-yl]-1-naphthoic acid TLC: Rf 0.43 (chloroform:methanol:aqueous ammonia=79:20:1);

$^1$H-NMR (CDCl$_3$): δ 1.00 (t, 6H), 2.68-3.00 (m, 9H), 4.08-4.10 (m, 2H), 4.51 (s, 2H), 6.61 (s, 1H), 6.69-6.72 (m, 1H), 6.79-6.81 (m, 1H), 7.04-7.05 (m, 2H), 7.13-7.18 (m, 1H), 7.38-7.50 (m, 3H), 7.68 (d, 1H), 7.76-7.80 (m, 2H), 7.85 (d, 1H), 8.19 (d, 1H).

Example 32-(40)

2-(3-{[1-(4-fluorobutyl)-4-methyl-1H-indol-3-yl]methyl}imidazo[1,2-a]pyridin-2-yl)-1-naphthoic acid TLC: Rf 0.50 (chloroform:methanol:aqueous ammonia=79:20:1);

$^1$H-NMR (DMSO-D$_6$): δ 1.35-1.46 (m, 2H), 1.56-1.63 (m, 2H), 2.64 (s, 3H), 3.89 (t, 2H), 4.15-4.18 (m, 1H), 4.27-4.30 (m, 1H), 4.72 (s, 2H), 6.42 (s, 1H), 6.72 (d, 1H), 6.79-6.82 (m, 1H), 6.93-6.97 (m, 1H), 7.13 (d, 1H), 7.19-7.23 (m, 1H), 7.48-7.58 (m, 4H), 7.82 (d, 1H), 7.88 (d, 1H), 8.06 (d, 1H), 8.09 (d, 1H).

Example 32-(41)

2-(3-{[4-methyl-1-(4,4,4-trifluorobutyl)-1H-indol-3-yl]methyl}imidazo[1,2-a]pyridin-2-yl)-1-naphthoic acid TLC: Rf 0.47 (chloroform:methanol:aqueous ammonia=79:20:1);

$^1$H-NMR (DMSO-D$_6$): δ 1.71-1.78 (m, 2H), 1.90-2.02 (m, 2H), 2.65 (s, 3H), 3.96 (t, 2H), 4.71 (s, 2H), 6.41 (s, 1H), 6.74 (d, 1H), 6.79-6.82 (m, 1H), 6.95-6.99 (m, 1H), 7.15 (d, 1H), 7.20-7.24 (m, 1H), 7.49-7.59 (m, 4H), 7.84 (d, 1H), 7.89 (d, 1H), 8.04 (d, 1H), 8.10 (d, 1H).

Example 32-(42)

2-(3-{[1-(4-hydroxybutyl)-4-methyl-1H-indol-3-yl]methyl}imidazo[1,2-a]pyridin-2-yl)-1-naphthoic acid TLC: Rf 0.24 (chloroform:methanol:aqueous ammonia=79:20:1);

$^1$H-NMR (DMSO-D$_6$): δ 1.18-1.27 (m, 2H), 1.52-1.60 (m, 2H), 2.63 (s, 3H), 3.27 (t, 2H), 3.86 (t, 2H), 4.71 (s, 2H), 6.42 (s, 1H), 6.70 (d, 1H), 6.77-6.81 (m, 1H), 6.91-6.96 (m, 1H), 7.11 (d, 1H), 7.17-7.20 (m, 1H), 7.45-7.52 (m, 3H), 7.56 (d, 1H), 7.77 (d, 1H), 7.84 (d, 1H), 8.05-8.10 (m, 2H).

Example 32-(43)

2-(3-{[1-(3-fluoropropyl)-4-methyl-1H-indol-3-yl]methyl}imidazo[1,2-a]pyridin-2-yl)-1-naphthoic acid TLC: Rf 0.58 (chloroform:methanol:aqueous ammonia=79:20:1);

$^1$H-NMR (DMSO-D$_6$): δ 1.81-1.93 (m, 2H), 2.64 (s, 3H), 3.96 (t, 2H), 4.10-4.13 (m, 1H), 4.22-4.25 (m, 1H), 4.72 (s,

2H), 6.42 (s, 1H), 6.72 (d, 1H), 6.79-6.82 (m, 1H), 6.93-6.97 (m, 1H), 7.11 (d, 1H), 7.18-7.22 (m, 1H), 7.46-7.53 (m, 3H), 7.57 (d, 1H), 7.77 (d, 1H), 7.85 (d, 1H), 8.07-8.10 (m, 2H).

Example 32-(44)

2-(3-{[4-methyl-1-(tetrahydro-2H-pyran-2-ylmethyl)-1H-indol-3-yl]methyl}imidazo[1,2-a]pyridin-2-yl)-1-naphthoic acid TLC: Rf 0.61 (chloroform:methanol:aqueous ammonia=79:20:1);
$^1$H-NMR (DMSO-D$_6$): δ 1.26-1.33 (m, 6H), 2.64 (s, 3H), 3.09-3.16 (m, 1H), 3.34-3.38 (m, 1H), 3.65-3.90 (m, 3H), 4.72 (s, 2H), 6.37 (s, 1H), 6.71 (d, 1H), 6.80-6.83 (m, 1H), 6.92-6.96 (m, 1H), 7.14 (d, 1H), 7.21-7.25 (m, 1H), 7.50-7.60 (m, 4H), 7.86-7.92 (m, 2H), 8.04 (d, 1H), 8.09 (d, 1H).

Example 32-(45)

2-[3-({4-methyl-1-[3-(pyridin-3-yl)propyl]-1H-indol-3-yl}methyl)imidazo[1,2-a]pyridin-2-yl]-1-naphthoic acid TLC: Rf 0.62 (chloroform:methanol:aqueous ammonia=79:20:1);
$^1$H-NMR (DMSO-D$_6$): δ 1.80-1.88 (m, 2H), 2.36 (t, 2H), 2.65 (s, 3H), 3.90 (t, 2H), 4.71 (s, 2H), 6.42 (s, 1H), 6.73 (d, 1H), 6.80-6.84 (m, 1H), 6.94-6.98 (m, 1H), 7.09 (d, 1H), 7.14-7.17 (m, 1H), 7.21-7.25 (m, 1H), 7.33 (d, 1H), 7.49-7.60 (m, 4H), 7.86-7.90 (m, 2H), 8.02 (d, 1H), 8.14 (d, 1H), 8.21 (s, 1H), 8.32 (d, 1H).

Example 32-(46)

2-[3-({4-methyl-1-[3-(pyridin-4-yl)propyl]-1H-indol-3-yl}methyl)imidazo[1,2-a]pyridin-2-yl]-1-naphthoic acid TLC: Rf 0.62 (chloroform:methanol:aqueous ammonia=79:20:1);
$^1$H-NMR (DMSO-D$_6$): δ 1.81-1.88 (m, 2H), 2.34 (t, 2H), 2.66 (s, 3H), 3.89 (t, 2H), 4.72 (s, 2H), 6.41 (s, 1H), 6.73 (d, 1H), 6.81-6.84 (m, 1H), 6.93-6.98 (m, 3H), 7.10 (d, 1H), 7.22-7.25 (m, 1H), 7.49-7.61 (m, 4H), 7.86-7.90 (m, 2H), 8.02 (d, 1H), 8.13 (d, 1H), 8.32 (d, 2H).

Example 32-(47)

2-[3-({1-[3-(1H-imidazol-1-yl)propyl]-4-methyl-1H-indol-3-yl}methyl)imidazo[1,2-a]pyridin-2-yl]-1-naphthoic acid TLC: Rf 0.52 (chloroform:methanol:aqueous ammonia=79:20:1);
$^1$H-NMR (DMSO-D$_6$): δ 1.95-2.02 (m, 2H), 2.65 (s, 3H), 3.74 (t, 2H), 3.86 (t, 2H), 4.71 (s, 2H), 6.39 (s, 1H), 6.74 (d, 1H), 6.81-6.85 (m, 2H), 6.92 (s, 1H), 6.95-6.99 (m, 1H), 7.06 (d, 1H), 7.22-7.26 (m, 1H), 7.43 (s, 1H), 7.50-7.60 (m, 4H), 7.87-7.91 (m, 2H), 8.02 (d, 1H), 8.14 (d, 1H).

Example 33-(1)~(4)

By the same procedure as a series of reactions of Example 30→Example 7, using the corresponding epoxide derivatives instead of glycidol, the compounds of the present invention having the following physical data were obtained.

Example 33-(1)

2-(3-{[1-(2-hydroxypropyl)-4-methyl-1H-indol-3-yl]methyl}imidazo[1,2-a]pyridin-2-yl)-1-naphthoic acid TLC: Rf 0.49 (chloroform:methanol:aqueous ammonia=79:20:1);
$^1$H-NMR (DMSO-D$_6$): δ 0.86 (d, 3H), 2.63 (s, 3H), 3.73-3.81 (m, 3H), 4.70 (s, 2H), 6.47 (s, 1H), 6.68 (d, 1H), 6.76-6.79 (m, 1H), 6.90-6.93 (m, 1H), 7.13 (d, 1H), 7.16-7.20 (m, 1H), 7.43-7.50 (m, 3H), 7.55 (d, 1H), 7.73 (d, 1H), 7.82 (d, 1H), 8.06 (d, 1H), 8.11 (d, 1H).

Example 33-(2)

2-(3-{[1-(2-hydroxy-3-methoxypropyl)-4-methyl-1H-indol-3-yl]methyl}imidazo[1,2-a]pyridin-2-yl)-1-naphthoic acid TLC: Rf 0.51 (chloroform:methanol:aqueous ammonia=79:20:1);
$^1$H-NMR (DMSO-D$_6$): δ 2.64 (s, 3H), 3.06-3.09 (m, 5H), 3.72-3.82 (m, 2H), 3.91-3.96 (m, 1H), 4.69 (s, 2H), 6.43 (s, 1H), 6.70 (d, 1H), 6.78-6.81 (m, 1H), 6.92-6.95 (m, 1H), 7.13 (d, 1H), 7.18-7.22 (m, 1H), 7.45-7.58 (m, 4H), 7.78 (d, 1H), 7.85 (d, 1H), 8.06-8.10 (m, 2H).

Example 33-(3)

2-(3-{[1-(2-hydroxy-2-methylpropyl)-4-methyl-1H-indol-3-yl]methyl}imidazo[1,2-a]pyridin-2-yl)-1-naphthoic acid TLC: Rf 0.49 (chloroform:methanol:aqueous ammonia=79:20:1);
$^1$H-NMR (DMSO-D$_6$): δ 0.93 (s, 6H), 2.64 (s, 3H), 3.78 (s, 2H), 4.70 (s, 2H), 6.43 (s, 1H), 6.70 (d, 1H), 6.80-6.83 (m, 1H), 6.92-6.95 (m, 1H), 7.21-7.25 (m, 2H), 7.51-7.61 (m, 4H), 7.88-7.93 (m, 2H), 8.02 (d, 1H), 8.11 (d, 1H).

Example 33-(4)

2-(3-{[1-(2-hydroxy-3-phenoxypropyl)-4-methyl-1H-indol-3-yl]methyl}imidazo[1,2-a]pyridin-2-yl)-1-naphthoic acid TLC: Rf 0.59 (chloroform:methanol:aqueous ammonia=79:20:1);
$^1$H-NMR (CDCl$_3$): δ 2.68 (s, 3H), 3.51-3.67 (m, 2H), 3.73-3.90 (m, 1H), 3.95-4.09 (m, 2H), 4.58 (s, 2H), 6.46 (s, 1H), 6.61-6.70 (m, 4H), 6.77-7.17 (m, 8H), 7.33-8.03 (m, 6H).

Pharmacological Experiment Examples

Pharmacological Experiment Example 1

Measurement of Human Chymase Enzyme Inhibitory Activity

Human Chymase Pure (hereunder called chymase; East Coast Biologics) was stored in a freezer at −20° C., and diluted with distilled water immediately prior to use. N-Succinyl-Ala-Ala-Pro-Phe-p-nitroanilide (hereunder called the peptide substrate; Sigma Aldrich) was prepared with dimethylsulfoxide (hereunder called DMSO) as a 50 mmol/L solution, and stored in a freezer at −20° C. The compound of the present invention and the comparative compounds were prepared with DMSO as 10 mmol/L solutions, and stored in a freezer at −20° C. On the day of measurement, the solutions of the compound of the present invention and the comparative compound were diluted in stages with 50% DMSO to 10 times concentration of the final target concentration, and the solution were prepared. 10 μL solutions of the compounds of the present invention and the comparative compounds, and 80 μL solution of a peptide substrate (final concentration 2.5 mmol/L) diluted with assay buffer (50 mmol/L Tris-HCl, 150 mmol/L NaCl, 50 units/mL heparin (pH 7.6)) were added to a 96-well microplate, incubated for 10 minutes at 37° C. 10 μL of chymase was added to a final concentration of 0.1 μg/L to initiate enzyme activity. Absorbance at 405 nm was monitored for 5 minutes at 30-second intervals, and the reaction speed (Δm O.D./minute) was measured. 10 μL of 50% DMSO was added to the control well and blank well in place of the solutions of the compound of the present invention and the comparative compound. Moreover, 10 μL of distilled water was added to the blank well in place of chymase. Given 100% as the value of the control well reaction speed minus the blank well reaction speed, the reaction speeds of the wells containing the compound of the present invention and the comparative compounds were calculated as percentages. The concentration of the compound of the present invention and the concentration of the comparative compound at which 50% and 90% of enzyme activity was inhibited were shown as the $IC_{50}$ value and $IC_{90}$ value.

As a result, as shown in Table 1, the compound of the present invention was shown to have extremely strong human chymase inhibitory activity in comparison with the human chymase inhibitory activity of the compound of Example 2 described in Patent Document 1
(4-[3-(4-methyl-benzo[b]thiophen-3-ylmethyl)-imidazo[1,2-a]pyridin-2-ylsulfanyl]butanoic acid (Comparative Compound 2)), Compound No. 18
(2-{[1-(1-naphthylmethyl)-1H-benzimidazol-2-yl]thio}benzoic acid (Comparative Compound 3)) and Compound No. 26
(2-([1-[(1,4-dimethyl-1H-indol-3-yl)methyl]-1H-benzimidazol-2-yl]thio)benzoic acid (Comparative Compound 4)) described in Patent Document 2, and the Compound of Table 1 described in Patent Document 3
(4-(1-((4-methylbenzothiophen-3-yl)methyl)benzimidazol-2-ylthio)butanoic acid (Comparative Compound 1).

TABLE 1

| | Human chymase inhibitory activity | |
|---|---|---|
| | $IC_{50}(\mu M)$ | $IC_{90}(\mu M)$ |
| Example 7 | 0.001 | 0.063 |
| Example 11 | 0.023 | 0.27 |
| Example 13 | 0.028 | 0.20 |
| Example 15 | 0.030 | 0.24 |
| Example 16 | 0.001 | 0.006 |
| Example 19 | 0.011 | 0.12 |
| Example 23-(4) | 0.002 | 0.008 |
| Comparative Compound 1 | 0.11 | 0.84 |
| Comparative Compound 2 | 0.34 | 2.8 |
| Comparative Compound 3 | 0.13 | 1.6 |
| Comparative Compound 4 | 0.075 | 0.79 |

Pharmacological Experiment Example 2

Measurement of Cell Toxicity Using HepG2 Human Liver Cancer Cell Lines

HepG2 cells were seeded on a collagen coated 96-well plate to a cell density of 15,000 cells/well, and cultured overnight at 37° C. in a culture vessel with 5% $CO_2$, 95% air. The cells were then exposed to the compound of the present invention and the comparative compounds for 24 hours. The compound of the present invention and the comparative compounds were dissolved with DMSO, and then diluted 100 times with culture liquid comprising L-glutamine, non-essential amino acids and 1% bovine fetal serum which were added to minimum essential medium (MEM). The treatment concentrations of the compound of the prevent invention and the comparative compounds were 0, 6.25, 12.5, 25, 50 and 100 μmol/L. After 24 hours of exposure, the ATP concentration in the cells was measured with a Celltiter Glo Luminescent Assay Kit (Promega), and the cell toxicity effects of the compound of the prevent invention and the comparative compounds were evaluated. The cells were dissolved with the assay buffer in the measurement kit, and the ATP concentration released from the cells was measured based on luciferin-luciferase enzyme activity. Light emission was measured with a SpectraMax plate reader (Molecular Device). The cell toxicity effects of the compound of the prevent invention and the comparative compounds are represented as the concentrations ($IC_{10}$ and $IC_{50}$) that suppressed 10% and 50% of light emission. That is, the $IC_{10}$ value was calculated as the concentration that produced toxicity in 10% of HepG2 cells, and the $IC_{50}$ value was calculated as the concentration that produced toxicity in 50% of cells.

As a result, as shown in Table 2, the ratio of HepG2 cell toxicity (shown in Table 2) to human chymase inhibitory activity (shown in Table 1) using the compound of the present invention ($IC_{50}$ (HepG2 cell toxicity)/$IC_{50}$ (human chymase inhibitory activity), $IC_{10}$ (HepG2 cell toxicity)/($IC_{90}$ (human chymase inhibitory activity)) was much greater than using the comparative compounds. Thus, the compound of the present invention can be a drug that greatly reduces the risk of hepatotoxicity when used as an agent for preventing and/or treating chymase-mediated diseases.

TABLE 2

| | Cell toxicity in HepG2 human liver cancer cell lines | | Ratio of HepG2 cell toxicity (Table 2) to human chymase inhibitory activity (Table 1) | |
|---|---|---|---|---|
| | $IC_{50} (\mu M)$ | $IC_{10} (\mu M)$ | $IC_{50}$ (cell toxicity data)/ $IC_{50}$ (chymase inhibitory activity data) | $IC_{10}$ (cell toxicity data)/ $IC_{90}$ (chymase inhibitory activity data) |
| Example 7 | 132 | 58 | 132000 | 921 |
| Example 11 | >400 | 248 | 17391 | 919 |
| Example 13 | 424 | 135 | 15143 | 675 |

TABLE 2-continued

| | Cell toxicity in HepG2 human liver cancer cell lines | | Ratio of HepG2 cell toxicity (Table 2) to human chymase inhibitory activity (Table 1) | |
|---|---|---|---|---|
| | $IC_{50}$ (μM) | $IC_{10}$ (μM) | $IC_{50}$ (cell toxicity data)/ $IC_{50}$ (chymase inhibitory activity data) | $IC_{10}$ (cell toxicity data)/ $IC_{90}$ (chymase inhibitory activity data) |
| Example 15 | 267 | 115 | 8900 | 479 |
| Example 16 | 131 | 29 | 131000 | 4833 |
| Example 19 | 247 | 70 | 22455 | 583 |
| Example 23-(4) | 173 | 79 | 86500 | 9875 |
| Comparative Compound 1 | 81 | 45 | 736 | 54 |
| Comparative Compound 2 | 219 | 66 | 644 | 24 |
| Comparative Compound 3 | 40 | 29 | 308 | 18 |
| Comparative Compound 4 | 84 | 53 | 1120 | 67 |

Pharmacological Experiment Example 3

Stability Experiment Using Human Liver Microsomes

5 μL of the compound of the present invention and each comparative compound (10 mmol/L DMSO solution) was diluted with 195 μL of 50% acetonitrile aqueous solution to prepare 250 μmol/L solutions of the compound of the present invention and comparative compound. 245 μL of 0.5 mg/mL human liver microsomes (0.1 mol/L pH 7.4 phosphate buffer solution) containing NADPH Co factor (NADPH Regenerating System Solution A (BD Bioscience) and NADPH Regenerating System Solution B (BD Bioscience), each diluted 10 times and 50 times with 0.1 mol/L pH 7.4 phosphate buffer (NADP+2.6 mmol/L)) were added to a reaction container that had been warmed in advance to 37° C. in a water bath, and pre-incubated for 5 minutes, after which 5 μL solution of the compound of the present invention and the comparative compound was added to initiate a reaction (final concentration 5 μmol/L). Immediately after initiation 20 μL was collected, and 20 μL was added to 180 μL of acetonitrile containing I.S. (internal standard (warfarin)) to terminate the reaction. 180 μL of 50% acetonitrile aqueous solution was added to this 20 μL on a plate with a protein exclusion filter, stirred and filtered by suction. The filtrate was used as a standard sample. After incubating the reaction solution for 15 minutes, 20 μL of a liver microsome solution was collected, and added to 180 μL of acetonitrile containing I.S. (internal standard (warfarin)) in order to terminate the reaction. 180 μL of 50% acetonitrile aqueous solution was added to this 20 μL on a plate with a protein exclusion filter, stirred and filtered by suction. The filtrate was used as a reaction sample. The survival ratio (%) was calculated by injecting 5 μL of sample solution into a LC-MS/MS (Thermo Scientific Discovery Max), dividing the peak area ratio of the reaction sample (the compound of the present invention and the comparative compound/I.S.) by the peak area ratio of the standard sample, and multiplying by 100.

As a result, as shown in Table 3, the compound of the present invention had uniformly high stability with respect to human liver microsomes, indicating extremely high metabolic stability.

TABLE 3

| | Human liver Ms stability (%) |
|---|---|
| Example 7 | 93 |
| Example 11 | 86 |
| Example 13 | 93 |
| Example 15 | 87 |
| Example 16 | 88 |
| Example 19 | 100 |
| Example 23-(4) | 100 |

Formulation Example

Formulation Example 1

The following components were admixed in a conventional method and punched out to obtain 10,000 tablets each containing 10 mg of the active ingredient.

| | |
|---|---|
| 2-{3-[(4-methyl-1H-indol-3-yl)methyl]imidazo[1,2-a]pyridin-2-yl}-1-naphthoic acid | 100 g |
| Carboxymethyl cellulose calcium (disintegrating agent) | 20 g |
| Magnesium stearate (lubricant agent) | 10 g |
| Microcrystalline cellulose | 870 g |

Formulation Example 2

The following components were admixed in a conventional method, followed by filtration with a dust-removing filter. The resultant filtrate in an amount of 5 mL was loaded into an ampule, and the resultant mixture was sterilized by heat with an autoclave to obtain 10,000 ampules containing 20 mg of active ingredient per ampule.

| | |
|---|---|
| 2-{3-[(4-methyl-1H-indol-3-yl)methyl]imidazo[1,2-a]pyridin-2-yl}-1-naphthoic acid | 200 g |
| Mannitol | 20 g |
| Distilled water | 50 L |

INDUSTRIAL APPLICABILITY

The compound of the present invention has chymase inhibitory activity, and is effective for preventing and/or treating chymase-mediated diseases, such as skin diseases, circulatory diseases, digestive system diseases, respiratory diseases, liver diseases, ocular diseases or the like.

The invention claimed is:
1. A compound represented by the formula (I)

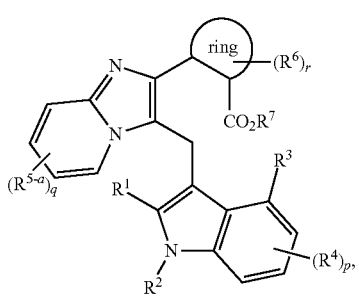

(I)

wherein

represents a benzene ring or a naphthalene ring or a 6- to 10-membered monocyclic or bicyclic aromatic heterocycle;
$R^1$ represents a hydrogen atom, methyl group, trifluoromethyl group, difluoromethyl group, fluorine atom or chlorine atom;
$R^2$ represents a hydrogen atom, $C_{1-10}$ alkyl group optionally substituted with 1 to 6 of $R^{11}$, $C_{2-10}$ alkenyl optionally substituted with 1 to 6 of $R^{11}$, or $C_{2-10}$ alkynyl optionally substituted with 1 to 6 of $R^{11}$;
$R^{11}$ represents
(i) a halogen atom,
(ii) $OR^8$,
where $R^8$ is (1) a hydrogen atom, (2) $C_{1-3}$ alkyl group, (3) $C_{1-3}$ haloalkyl group, (4) a $C_{5-6}$ carbocycle, (5) a 5- to 6-membered heterocycle containing 1 to 2 nitrogen atoms, 1 oxygen atom and/or 1 optionally oxidized sulfur atom, or (6) $C_{1-3}$ alkyl group substituted with a hydroxyl group, $C_{1-3}$ alkoxy group or $NR^9R^{10}$, where $R^9$ and $R^{10}$ each independently represent a hydrogen atom, $C_{1-3}$ alkyl group or phenyl group,
(iii) $NR^9R^{10}$, where $R^9$ and $R^{10}$ each independently represent a hydrogen atom, $C_{1-3}$ alkyl group or phenyl group,
(iv) a $C_{5-6}$ carbocycle optionally substituted with at least one selected from a halogen atom, oxo group and methyl group, or
(v) a 3- to 10-membered heterocycle containing 1 to 4 nitrogen atoms, 1 to 2 oxygen atoms and/or 1 to 2 optionally oxidized sulfur atoms, optionally substituted with at least one group selected from a halogen atom, an oxo group and a methyl group;
$R^3$ represents a hydrogen atom, methyl group, or fluorine atom;
$R^4$ represents a hydrogen atom, $C_{1-2}$ alkyl group, $C_{1-2}$ haloalkyl group, or halogen atom;
$R^5$ represents a hydrogen atom, $C_{1-3}$ alkyl group, $C_{1-3}$ haloalkyl group, or halogen atom;
$R^6$ represents a hydrogen atom, $C_{1-3}$ alkyl group, $C_{1-3}$ haloalkyl group or halogen atom;
$R^7$ represents a hydrogen atom, $C_{1-4}$ alkyl group, allyl group, trichloroethyl group, benzyl group, phenacyl group, p-methoxybenzyl group, trityl group, or 2-chlorotrityl group;
p is an integer of 1 to 3;
q is an integer of 1 to 4; and
r is an integer of 1 to 6;
and wherein:
when p represents 2 or more, each $R^4$ may independently be the same or different,
when q represents 2 or more, each $R^5$ may independently be the same or different, and
when r represents 2 or more, each $R^6$ may independently be the same or different, or a salt thereof, an N-oxide thereof, or a prodrug thereof.
2. The compound described in claim 1, represented by the formula (I-a)

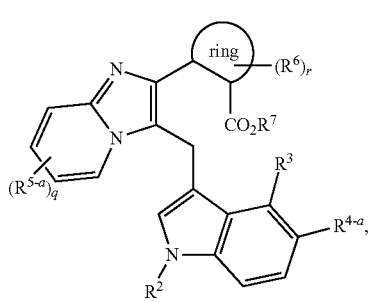

(I-a)

wherein $R^{4-a}$ represents a hydrogen atom, methyl group, fluorine atom or chlorine atom, $R^{5-a}$ represents a hydrogen atom, methyl group or fluorine atom, and

represents a benzene ring or a naphthalene ring or a 6- to 10-membered monocyclic or bicyclic aromatic heterocycle;
$R^2$ represents a hydrogen atom, $C_{1-10}$ alkyl group optionally substituted with 1 to 6 of $R^{11}$, $C_{2-10}$ alkenyl optionally substituted with 1 to 6 of $R^{11}$, or $C_{2-10}$ alkynyl optionally substituted with 1 to 6 of $R^{11}$;
$R^{11}$ represents
(i) a halogen atom,
(ii) $OR^8$,
where $R^8$ is (1) a hydrogen atom, (2) $C_{1-3}$ alkyl group, (3) $C_{1-3}$ haloalkyl group, (4) a $C_{5-6}$ carbocycle, (5) a 5- to 6-membered heterocycle containing 1 to 2 nitrogen atoms, 1 oxygen atom and/or 1 optionally oxidized sulfur atom, or (6) $C_{1-3}$ alkyl group substituted with a hydroxyl group, $C_{1-3}$ alkoxy group or $NR^9R^{10}$, where $R^9$ and $R^{10}$ each independently represent a hydrogen atom, $C_{1-3}$ alkyl group or phenyl group,
(iii) $NR^9R^{10}$, where $R^9$ and $R^{10}$ each independently represent a hydrogen atom, $C_{1-3}$ alkyl group or phenyl group,
(iv) a $C_{5-6}$ carbocycle optionally substituted with at least one selected from a halogen atom, oxo group and methyl group, or
(v) a 3- to 10-membered heterocycle containing 1 to 4 nitrogen atoms, 1 to 2 oxygen atoms and/or 1 to 2 optionally oxidized sulfur atoms, optionally substituted with at least one group selected from a halogen atom, an oxo group and a methyl group;

$R^3$ represents a hydrogen atom, methyl group, or fluorine atom;

$R^6$ represents a hydrogen atom, $C_{1-3}$ alkyl group, $C_{1-3}$ haloalkyl group or halogen atom;

$R^7$ represents a hydrogen atom, $C_{1-4}$ alkyl group, allyl group, trichloroethyl group, benzyl group, phenacyl group, p-methoxybenzyl group, trityl group, or 2-chlorotrityl group;

q is an integer of 1 to 4; and r is an integer of 1 to 6;

and wherein:

when q represents 2 or more, each $R^{5-a}$ may independently be the same or different, and when r represents 2 or more, each $R^6$ may independently be the same or different, or a salt thereof, an N-oxide thereof, or a prodrug thereof.

3. The compound described in claim 2, represented by the formula (I-b) or (I-c)

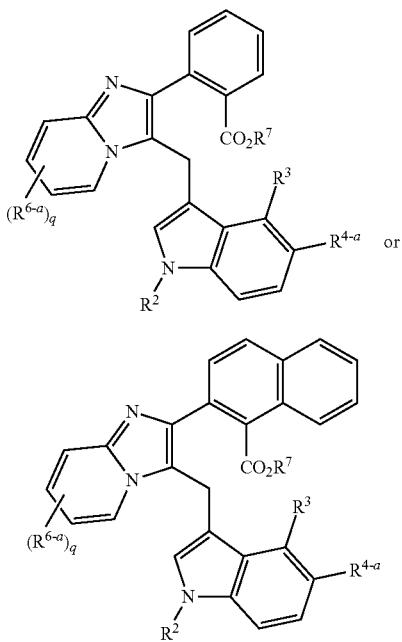

wherein all symbols have the same meaning as in claim 2, or a salt thereof, an N-oxide thereof, or a prodrug thereof.

4. The compound described in claim 3, wherein $R^2$ represents a hydrogen atom, $C_{1-10}$ alkyl group optionally substituted with 1 to 6 of $R^{12}$, $C_{2-10}$ alkenyl optionally substituted with 1 to 6 of $R^{12}$ or $C_{2-10}$ alkynyl optionally substituted with 1 to 6 of $R^{12}$; and $R^{12}$ represents a halogen atom, hydroxyl group, dimethylamino group, pyrrolidinyl group, N-methylpyrrolidinyl group, piperidinyl group, phenoxy group, phenyl group optionally substituted with halogen atoms, tetrahydropyranyl group, 2,3-dihydrobenzofuranyl group, thiophenyl group, diisopropylamino group, methyl(phenyl)amino group, piperadinyl group, 2-oxo-1-pyrrolidinyl group, morpholinyl group, 1,1-dioxothiomorpholinyl group, imidazolyl group, pyridyl group, 2-methoxyethylenoxy group, dimethylaminoethylenoxy group, diethylaminoethylenoxy group, 1,2,3,4-tetrahydroisoquinolinyl group, azepanyl group, pyrazolyl group, 2-oxoimidazolidinyl group, diethylamino group, methoxy group or N-methylpyrazolyl group.

5. The compound described in claim 3, wherein $R^2$ represents $C_{1-6}$ alkyl group substituted with 1 to 6 of $R^{12}$, $C_{2-6}$ alkenyl group optionally substituted with 1 to 6 of $R^{12}$, or $C_{2-6}$ alkynyl group optionally substituted with 1 to 6 of $R^{12}$, and $R^{12}$ represents a halogen atom, hydroxyl group, dimethylamino group, pyrrolidinyl group, N-methylpyrrolidinyl group, piperidinyl group, phenoxy group, phenyl group optionally substituted with halogen atoms, tetrahydropyranyl group, 2,3-dihydrobenzofuranyl group, thiophenyl group, diisopropylamino group, methyl(phenyl)amino group, piperadinyl group, 2-oxo-1-pyrrolidinyl group, morpholinyl group, 1,1-dioxothiomorpholinyl group, imidazolyl group, pyridyl group, 2-methoxyethylenoxy group, dimethylaminoethylenoxy group, diethylaminoethylenoxy group, 1,2,3,4-tetrahydroisoquinolinyl group, azepanyl group, pyrazolyl group, 2-oxoimidazolidinyl group, diethylamino group, methoxy group or N-methylpyrazolyl group.

6. The compound described in claim 4, wherein $R^7$ is a hydrogen atom.

7. The compound described in claim 6, wherein the compound represented by the formula (I) is selected from the group consisting of (1) 2-{3-[(4-methyl-1H-indol-3-yl)methyl]imidazo[1,2-a]pyridin-2-yl}-1-naphthoic acid, (2) 2-{3-[(1,4-dimethyl-1H-indol-3-yl)methyl]-6-methylimidazo[1,2-a]pyridin-2-yl}benzoic acid, (3) 2-{3-[(1,4-dimethyl-1H-indol-3-yl)methyl]imidazo[1,2-a]pyridin-2-yl}benzoic acid, (4) 2-{3-[(1-ethyl-4-methyl-1H-indol-3-yl)methyl]imidazo[1,2-a]pyridin-2-yl}benzoic acid, (5) 2-{6-fluoro-3-[(4-methyl-1H-indol-3-yl)methyl]imidazo[1,2-a]pyridin-2-yl}-1-naphthoic acid, (6) 2-{3-[(5-fluoro-4-methyl-1H-indol-3-yl)methyl]imidazo[1,2-a]pyridin-2-yl}benzoic acid, (7) 2-[3-({4-methyl-1-[2-(4-morpholinyl)ethyl]-1H-indol-3-yl}methyl)imidazo[1,2-a]pyridin-2-yl]-1-naphthoic acid, (8) 2-(3-{[4-methyl-1-(2-propanyl)-1H-indol-3-yl]methyl}imidazo[1,2-a]pyridin-2-yl)-1-naphthoic acid, (9) 2-{3-[(4-methyl-1-propyl-1H-indol-3-yl)methyl]imidazo[1,2-a]pyridin-2-yl}-1-naphthoic acid,

(10) 2-{3-[(1-ethyl-4-methyl-1H-indol-3-yl)methyl]imidazo[1,2-a]pyridin-2-yl}-1-naphthoic acid,

(11) 2-{3-[(5-fluoro-4-methyl-1H-indol-3-yl)methyl]imidazo[1,2-a]pyridin-2-yl}-1-naphthoic acid,

(12) 2-(3-{[1-(2-hydroxyethyl)-4-methyl-1H-indol-3-yl]methyl}imidazo[1,2-a]pyridin-2-yl)-1-naphthoic acid,

(13) 2-[3-({1-[3-(dimethylamino)-2-hydroxypropyl]-4-methyl-1H-indol-3-yl}methyl)imidazo[1,2-a]pyridin-2-yl]-1-naphthoic acid,

(14) 2-(3-{[1-(2,3-dihydroxypropyl)-4-methyl-1H-indol-3-yl]methyl}imidazo[1,2-a]pyridin-2-yl)-1-naphthoic acid,

(15) 2-[3-({1-[2-(dimethylamino)ethyl]-4-methyl-1H-indol-3-yl}methyl)imidazo[1,2-a]pyridin-2-yl]-1-naphthoic acid,

(16) 2-[3-({1-[3-(dimethylamino)propyl]-4-methyl-1H-indol-3-yl}methyl)imidazo[1,2-a]pyridin-2-yl]-1-naphthoic acid,

(17) 2-[3-({4-methyl-1-[2-(pyrrolidin-1-yl)ethyl]-1H-indol-3-yl}methyl)imidazo[1,2-a]pyridin-2-yl]-1-naphthoic acid,

(18) 2-[3-({4-methyl-1-[2-(1-methylpyrrolidin-2-yl)ethyl]-1H-indol-3-yl}methyl)imidazo[1,2-a]pyridin-2-yl]-1-naphthoic acid,

(19) 2-[3-({4-methyl-1-[2-(piperidin-1-yl)ethyl]-1H-indol-3-yl}methyl)imidazo[1,2-a]pyridin-2-yl]-1-naphthoic acid,
(20) 2-(3-{[4-methyl-1-(2-phenoxyethyl)-1H-indol-3-yl]methyl}imidazo[1,2-a]pyridin-2-yl)-1-naphthoic acid,
(21) 2-[3-({1-[(3R)-3-hydroxy-3-phenylpropyl]-4-methyl-1H-indol-3-yl}methyl)imidazo[1,2-a]pyridin-2-yl]-1-naphthoic acid,
(22) 2-[3-({1-[(3S)-3-hydroxy-3-phenylpropyl]-4-methyl-1H-indol-3-yl}methyl)imidazo[1,2-a]pyridin-2-yl]-1-naphthoic acid,
(23) 2-[3-({1-[2-(4-fluorophenyl)ethyl]-4-methyl-1H-indol-3-yl}methyl)imidazo[1,2-a]pyridin-2-yl]-1-naphthoic acid,
(24) 2-[3-({4-methyl-1-[2-(tetrahydro-2H-pyran-4-yl)ethyl]-1H-indol-3-yl}methyl)imidazo[1,2-a]pyridin-2-yl]-1-naphthoic acid,
(25) 2-[3-({1-[2-(2,3-dihydro-1-benzofuran-5-yl)ethyl]-4-methyl-1H-indol-3-yl}methyl)imidazo[1,2-a]pyridin-2-yl]-1-naphthoic acid,
(26) 2-(3-{[4-methyl-1-(3-phenylpropyl)-1H-indol-3-yl]methyl}imidazo[1,2-a]pyridin-2-yl)-1-naphthoic acid,
(27) 2-(3-{[4-methyl-1-(piperidin-4-ylmethyl)-1H-indol-3-yl]methyl}imidazo[1,2-a]pyridin-2-yl)-1-naphthoic acid,
(28) 2-(3-{[1-(3-hydroxypropyl)-4-methyl-1H-indol-3-yl]methyl}imidazo[1,2-a]pyridin-2-yl)-1-naphthoic acid,
(29) 2-[3-({1-[2-(dipropan-2-ylamino)ethyl]-4-methyl-1H-indol-3-yl}methyl)imidazo[1,2-a]pyridin-2-yl]-1-naphthoic acid,
(30) 2-[3-({4-methyl-1-[2-(piperazin-1-yl)ethyl]-1H-indol-3-yl}methyl)imidazo[1,2-a]pyridin-2-yl]-1-naphthoic acid,
(31) 2-[3-({4-methyl-1-[2-(2-oxopyrrolidin-1-yl)ethyl]-1H-indol-3-yl}methyl)imidazo[1,2-a]pyridin-2-yl]-1-naphthoic acid,
(32) 2-[3-({1-[2-(1,1-dioxidethiomorpholin-4-yl)ethyl]-4-methyl-1H-indol-3-yl}methyl)imidazo[1,2-a]pyridin-2-yl]-1-naphthoic acid,
(33) 2-[3-({1-[2-(3,4-dihydroisoquinolin-2(1H)-yl)ethyl]-4-methyl-1H-indol-3-yl}methyl)imidazo[1,2-a]pyridin-2-yl]-1-naphthoic acid,
(34) 2-{3-[(1-{2-[2-(diethylamino)ethoxy]ethyl}-4-methyl-1H-indol-3-yl)methyl]imidazo[1,2-a]pyridin-2-yl}-1-naphthoic acid,
(35) 2-[3-({4-methyl-1-[2-(1-methyl-1H-pyrazol-4-yl)ethyl]-1H-indol-3-yl}methyl)imidazo[1,2-a]pyridin-2-yl]-1-naphthoic acid,
(36) 2-{3-[(1-{2-[2-(dimethylamino)ethoxy]ethyl}-4-methyl-1H-indol-3-yl)methyl]imidazo[1,2-a]pyridin-2-yl}-1-naphthoic acid,
(37) 2-(3-{[4-methyl-1-(4-methylpent-3-en-1-yl)-1H-indol-3-yl]methyl}imidazo[1,2-a]pyridin-2-yl)-1-naphthoic acid,
(38) 2-[3-({1-[2-(3-fluorophenyl)ethyl]-4-methyl-1H-indol-3-yl}methyl)imidazo[1,2-a]pyridin-2-yl]-1-naphthoic acid,
(39) 2-[3-({4-methyl-1-[2-(1H-pyrazol-1-yl)ethyl]-1H-indol-3-yl}methyl)imidazo[1,2-a]pyridin-2-yl]-1-naphthoic acid,
(40) 2-[3-({1-[2-(azepan-1-yl)ethyl]-4-methyl-1H-indol-3-yl}methyl)imidazo[1,2-a]pyridin-2-yl]-1-naphthoic acid,
(41) 2-{3-[(4-methyl-1-{2-[methyl(phenyl)amino]ethyl}-1H-indol-3-yl)methyl]imidazo[1,2-a]pyridin-2-yl}-1-naphthoic acid,
(42) 2-[3-({1-[2-(1H-imidazol-1-yl)ethyl]-4-methyl-1H-indol-3-yl}methyl)imidazo[1,2-a]pyridin-2-yl]-1-naphthoic acid,
(43) 2-[3-({4-methyl-1-[2-(pyridin-4-yl)ethyl]-1H-indol-3-yl}methyl)imidazo[1,2-a]pyridin-2-yl]-1-naphthoic acid,
(44) 2-[3-({1-[2-(2-methoxyethoxy)ethyl]-4-methyl-1H-indol-3-yl}methyl)imidazo[1,2-a]pyridin-2-yl]-1-naphthoic acid,
(45) 2-[3-({4-methyl-1-[2-(thiophen-3-yl)ethyl]-1H-indol-3-yl}methyl)imidazo[1,2-a]pyridin-2-yl]-1-naphthoic acid,
(46) 2-[3-({4-methyl-1-[2-(thiophen-2-yl)ethyl]-1H-indol-3-yl}methyl)imidazo[1,2-a]pyridin-2-yl]-1-naphthoic acid,
(47) 2-(3-{[4-methyl-1-(3-methylbut-3-en-1-yl)-1H-indol-3-yl]methyl}imidazo[1,2-a]pyridin-2-yl)-1-naphthoic acid,
(48) 2-[3-({4-methyl-1-[2-(2-oxoimidazolidin-1-yl)ethyl]-1H-indol-3-yl}methyl)imidazo[1,2-a]pyridin-2-yl]-1-naphthoic acid,
(49) 2-(3-{[1-(but-3-en-1-yl)-4-methyl-1H-indol-3-yl]methyl}imidazo[1,2-a]pyridin-2-yl)-1-naphthoic acid,
(50) 2-[3-({4-methyl-1-[(3Z)-pent-3-en-1-yl]-1H-indol-3-yl}methyl)imidazo[1,2-a]pyridin-2-yl]-1-naphthoic acid,
(51) 2-[3-({4-methyl-1-[3-(pyridin-2-yl)propyl]-1H-indol-3-yl}methyl)imidazo[1,2-a]pyridin-2-yl]-1-naphthoic acid,
(52) 2-(3-{[1-(3,4-dihydroxybutyl)-4-methyl-1H-indol-3-yl]methyl}imidazo[1,2-a]pyridin-2-yl)-1-naphthoic acid,
(53) 2-[3-({1-[2-(diethylamino)ethyl]-4-methyl-1H-indol-3-yl}methyl)imidazo[1,2-a]pyridin-2-yl]-1-naphthoic acid,
(54) 2-(3-{[1-(4-fluorobutyl)-4-methyl-1H-indol-3-yl]methyl}imidazo[1,2-a]pyridin-2-yl)-1-naphthoic acid,
(55) 2-(3-{[4-methyl-1-(4,4,4-trifluorobutyl)-1H-indol-3-yl]methyl}imidazo[1,2-a]pyridin-2-yl)-1-naphthoic acid,
(56) 2-(3-{[1-(4-hydroxybutyl)-4-methyl-1H-indol-3-yl]methyl}imidazo[1,2-a]pyridin-2-yl)-1-naphthoic acid,
(57) 2-(3-{[1-(3-fluoropropyl)-4-methyl-1H-indol-3-yl]methyl}imidazo[1,2-a]pyridin-2-yl)-1-naphthoic acid,
(58) 2-(3-{[4-methyl-1-(tetrahydro-2H-pyran-2-ylmethyl)-1H-indol-3-yl]methyl}imidazo[1,2-a]pyridin-2-yl)-1-naphthoic acid,
(59) 2-[3-({4-methyl-1-[3-(pyridin-3-yl)propyl]-1H-indol-3-yl}methyl)imidazo[1,2-a]pyridin-2-yl]-1-naphthoic acid,
(60) 2-[3-({4-methyl-1-[3-(pyridin-4-yl)propyl]-1H-indol-3-yl}methyl)imidazo[1,2-a]pyridin-2-yl]-1-naphthoic acid,
(61) 2-[3-({1-[3-(1H-imidazol-1-yl)propyl]-4-methyl-1H-indol-3-yl}methyl)imidazo[1,2-a]pyridin-2-yl]-1-naphthoic acid,
(62) 2-(3-{[1-(2-hydroxypropyl)-4-methyl-1H-indol-3-yl]methyl}imidazo[1,2-a]pyridin-2-yl)-1-naphthoic acid,
(63) 2-(3-{[1-(2-hydroxy-3-methoxypropyl)-4-methyl-1H-indol-3-yl]methyl}imidazo[1,2-a]pyridin-2-yl)-1-naphthoic acid,
(64) 2-(3-{[1-(2-hydroxy-2-methylpropyl)-4-methyl-1H-indol-3-yl]methyl}imidazo[1,2-a]pyridin-2-yl)-1-naphthoic acid, and

(65) 2-(3-{[1-(2-hydroxy-3-phenoxypropyl)-4-methyl-1H-indol-3-yl]methyl}imidazo[1,2-a]pyridin-2-yl)-1-naphthoic acid.

8. A pharmaceutical composition containing the compound represented by the formula (I) described in claim 1, a salt thereof, an N-oxide thereof, or a prodrug thereof as an active ingredient.

9. A pharmaceutical composition comprising the compound represented by the formula (I) described in claim 1, a salt thereof, an N-oxide thereof, or a prodrug thereof in combination with at least one kind selected from non-steroidal anti-inflammatory drugs, steroid drugs, immune suppressors, prostaglandins, anti-allergic drugs, mediator release inhibitors, leukotriene receptor antagonists, antihistamines, opioid agonists, phosphodiesterase inhibitors, forskolin preparations, nitric oxide synthase inhibitors, cannabinoid-2 receptor stimulants, decoy preparations, aminosalicylic acid preparations, diuretics, angiotensin converting enzyme inhibitors, angiotensin II receptor antagonists, anti-arrhythmic drugs, digitalis preparations, chymase inhibitors, renin inhibitors, calcium antagonists, beta blockers, nitrate drugs, anti-aldosterone drugs, cardiac stimulants, antiplatelet drugs, anticoagulants, antifibrotic drugs, antihyperglycemic drugs, antihypertensive drugs, lipid improvers, anti-obesity drugs, liver supporting drugs and antioxidants.

10. A method for the treatment of a chymase-mediated disease, comprising administering to a patient an effective amount of the compound represented by the formula (I) described in claim 1, a salt thereof, an N-oxide thereof, or a prodrug thereof, wherein the chymase-mediated disease is at least one member selected from the group consisting of atopic dermatitis, ulcerative colitis, heart failure, pulmonary fibrosis, aneurysm, non-alcoholic steatohepatitis, peptic ulcer, and allergic conjunctivitis.

* * * * *